US012644103B2

(12) United States Patent
Neumayer et al.

(10) Patent No.: US 12,644,103 B2
(45) Date of Patent: Jun. 2, 2026

(54) POLYPEPTIDES CAPABLE OF CONVERTING SUBSTRATE 3-KETO-DEOXYNIVALENOL INTO 3-EPI-DEOXYNIVALENOL

(71) Applicant: DSM Austria GmbH, Getzersdorf (AT)

(72) Inventors: Bernhard Neumayer, Vienna (AT); Elisabeth Streit, Vienna (AT); Barbara Weber, Vienna (AT); Gudrun Vogtentanz, Krems (AT)

(73) Assignee: DSM AUSTRIA GMBH, Getzersdorf (AT)

( * ) Notice: Subject to any disclaimer, the term of this patent is extended or adjusted under 35 U.S.C. 154(b) by 577 days.

(21) Appl. No.: 18/008,939

(22) PCT Filed: Jun. 8, 2021

(86) PCT No.: PCT/EP2021/065238
§ 371 (c)(1),
(2) Date: Dec. 7, 2022

(87) PCT Pub. No.: WO2021/249980
PCT Pub. Date: Dec. 16, 2021

(65) Prior Publication Data
US 2023/0235297 A1 Jul. 27, 2023

(30) Foreign Application Priority Data
Jun. 8, 2020 (EP) .................................... 20178702

(51) Int. Cl.
*C12N 9/02* (2006.01)
*A23K 20/189* (2016.01)
*A23L 29/00* (2016.01)

(52) U.S. Cl.
CPC .......... *C12N 9/0008* (2013.01); *A23K 20/189* (2016.05); *A23L 29/06* (2016.08); *C12Y 197/00* (2013.01)

(58) Field of Classification Search
CPC ................................ C12N 9/0008; C12N 9/02
See application file for complete search history.

(56) References Cited

U.S. PATENT DOCUMENTS

| | | | |
|---|---|---|---|
| 6,794,175 | B1 | 9/2004 | Binder et al. |
| 10,526,585 | B2 | 1/2020 | Binder et al. |

FOREIGN PATENT DOCUMENTS

| | | | |
|---|---|---|---|
| WO | 99/35240 | A1 | 7/1999 |
| WO | 2016/154640 | A1 | 10/2016 |
| WO | 2019046954 | A1 | 3/2019 |

OTHER PUBLICATIONS

Wei-Jie et al. A quinone-dependent dehydrogenase and two NADPH-dependent aldo/keto reductases detoxify deoxynivalenol in wheat via epimerization in a Devosia strain, Available on line—Mar. 27, 2020, Food Chemistry 321 (2020) 126703 (Year: 2020).*

Altschul, S.F. (1993) "A Protein Alignment Scoring System Sensitive at All Evolutionary Distances," Journal of Molecular Evolution, 36:290-300.

Altschul, S.F., et al. (1990) "Basic Local Alignment Search Tool," Journal of Molecular Biology, 215:403-410.

Altschul, S.F., et al.(1997) "Gapped BLAST and PSI-BLAST: a new generation of protein database search programs," Nucleic Acids Research, 25:3389-3402.

Brutlag, D.L., et al. (1990) "Improved sensitivity of biological sequence database searches," Bioinformatics, 6:237-245.

Creighton, T.E., (1993) "Proteins—Structure and Molecular Properties," 2nd Ed., W.H. Freeman and Company, New York; copyright, pp. 91-93.

Hassan, Y.I., et al., (2017) "The enzymatic epimerization of deoxynivalenol by Devosia mutans proceeds through the formation of 3-keto-DON intermediate," Scientific Reports, 7:6929 (11 pages).

He, J.W., et al. (2015) "Toxicology of 3-epi-deoxynivalenol, a deoxynivalenol-transformation product by Devosia mutans 17-2-E-8," Food and Chemical Toxicology, 84:250-259.

Henikoff, S., and Henikoff, J.G. (1992) "Amino acid substitution matrices from protein blocks," P.N.A.S. USA, 89:10915-10919.

Kurtzman, C.P. (2009) "Biotechnological strains of Komagataella (pichia) pastoris and Komagataella phaffil as determined from multigene sequence analysis," Journal of Industrial Microbiology and Biotechnology, 36:1435-1438.

Payros, D., et al. (2016) "Toxicology of deoxynivalenol and its acetylated and modified forms," Archives of Toxicology, 90:2931-2957.

Pierron, A., et al. (2016) "Microbial biotransformation of DON: molecular basis for reduced toxicity," Scientific Reports, 6:29105 (13 pages).

(Continued)

*Primary Examiner* — Tekchand Saidha
(74) *Attorney, Agent, or Firm* — Mueting Raasch Group

(57) ABSTRACT

The present invention relates to a method of converting 3-keto-DON into 3-epi-DON, reducing the content of DON in a composition comprising DON or of reducing the toxicity of a composition comprising DON as well as a method for converting a trichothecene comprising a 3-oxo group into a trichothecene comprising a 3-hydroxy group using one or more polypeptide(s) comprising or consisting of SEQ ID NO. 1 or a sequence having a sequence identity of at least 72.0% to SEQ ID NO. 1. Also envisioned are feed or food additives or feed or food as well as pharmaceutical compositions comprising one or more polypeptide(s) comprising or consisting of a sequence of SEQ ID NO. 1 or a sequence having a sequence identity of at least 72.0% to SEQ ID NO. 1 as well as the manufacture thereof. Encompassed are further polypeptide(s) comprising or consisting of a sequence of SEQ ID NO. 1 or a sequence having a sequence identity of at least 88.5% to SEQ ID NO. 1. Also envisioned are host cells or plants.

18 Claims, 8 Drawing Sheets

Specification includes a Sequence Listing.

(56) References Cited

OTHER PUBLICATIONS

Rattan, S.I.S., et al. (1992) "Protein Synthesis, Posttranslational Modifications, and Aging," Annals of the New York Academy of Sciences, 663:48-62.
Schatzmayr, G., and Streit, E. (2013) "Global occurrence of mycotoxins in the food and feed chain: facts and figures," World Mycotoxin Journal, 6:213-222.
Seifter, S., and Englard, S. (1990) "Analysis for Protein Modifications and Nonprotein Cofactors," in Methods in Enzymology, 182:626-646.
Stenhagen, E., and Teorell, T. (1938) Electrophoretic Behaviour in Nucleic Acid-Protein Mixtures, Nature, 141:415.
Teorell, T., and Stenhagen, E. (1938) "Ein Universalpuffer für den pH-Bereich 2,0 bis 12,0," Biochemische Zeitschrift 299:416-419.
Thompson, J.D., et al. (1994) "Clustal W: improving the sensitivity of progressive multiple sequence alignment through sequence weighting, position-specific gap penalties and weight matrix choice," Nucleic Acids Research, 22:4673-4680.
Wold, F. (1983) "Posttranslational Protein Modifications: Perspectives and Prospectives," from Posttranslational Covalent Modifications of Proteins, B.C. Johnson Ed., Academic Press, New York , 1-17.
Yamada, Y., et al. (1995) "The Phylogenetic Relationships of Methanol-assimilating Yeasts Based on the Partial Sequences of 18S and 25S Ribosomal RNAS: The Proposal of Komagataella Gen. Nov. (*Saccharomycesceae*)," Bioscience, Biotechnology, and Biochemistry, 59:439-444.
Zdarta, J., et al. (2018) "A General Overview of Support Materials for Enzyme Immobilization: Characteristics, Properties, Practical Utility," Catalysts, 8:92 (27 pages).
Carere, J., et al. (2018) "The Identification of DepB: An Enzyme Responsible for the Final Detoxification Step in the Deoxynivalenol Epimerization Pathway in Devosia mutans 17-2-E-8", Frontiers in Microbiology, 9:1-9.
UniProt Accession No. A0A085FLV3: Aldo/keto reductase, 343AA, Oct. 29, 2014, 1 page.
He, W.-J., et al. (2020) "A quinone-dependent dehydrogenase and two NADPH-dependent aldo/keto reductases detoxify deoxynivalenol in wheat via epimerization in a Devosia strain", Food Chemistry, 321:1-10.

* cited by examiner

FIGURE 1

```
SEQ1     MDYRKLGNSGAVVSHLCLGTMTFGKEADEATSHLLLDDYVAAGGNFIDTADVYSTGVSET   60
SEQ2     MEYRKLGNSGTIVTSYCLGTMTFGAEADETTSHLILDDYVEAGGNFIDTANVYSLGVSEE   60
SEQ3     MDYRKLGNSGAVVSNLCLGTMTFGDEADEATSFVLMDQYVEAGGNFLDTADVYSAGLSEE   60
SEQ4     MDYRKLGNSGAVVSHLCLGTMTFGSEADEATSFKLLDDYVAAGGNFIDTADVYSAGVSEE   60
SEQ5     MKYRKLGNSGAVVSAYCLGTMTFGAESDEATSFRLMDDYVAAGGNFLDTANVYSAGVSEE   60
SEQ6     MQYRKLGNSGAVVSTQTLGTMTFGAEADEATSFQLMDDYVAAGGNFLDTADVYSAGTSEE   60
SEQ7     MEYRKLGNSGAIVTNYCLGTMTFGKESDEATSFRLMDDYVAAGGNFIDTANVYSDGLSEQ   60
SEQ8     MDYRKLGNSGAVVSSYCLGTMTFGAEADEATSHLLLDDYVEAGGNFIDTANVYSLGVSEE   60
SEQ9     MEYRKLGNSGTIVTSYCLGTMTFGAEADETTSHLILDDYVEAGGNFIDTANVYSLGVSEE   60
SEQ10    MEYRKLGNSGTIVTSYCLGTMTFGAEADETTSHLLLDDYVEAGGNFIDTANVYSLGVSEE   60
SEQ11    MEYRKLGNSGTIVSSYCLGTMTFGAEADEATSHLILDDYVEAGGNFIDTANVYSLGVSEE   60
SEQ12    MEYRKLGNSGTIVTSYCLGTMTFGAEADETTSHLILDDYVEAGGNFIDTANVYSLGVSEE   60
SEQ13    MDYRKLGNSGTVVTSYCLGTMTFGAEADEATSHLILDDYVEAGGNFIDTANVYSLGVSEE   60
SEQ14    MEYRKLGNSGAIVTSYCLGTMTFGAEADETTSHLLLDDYVEAGGNFIDTANVYSLGVSEE   60
SEQ15    MDYRKLGNSGAVVSSYCLGTMTFGAEADEATSHLLLDDYVEAGGNFIDTANVYSLGVSEE   60
SEQ16    MEYRKLGNSGTIVTSYCLGTMTFGAEADETTSHLILDDYVEAGGNFIDTANVYSLGVSEE   60
SEQ17    MDYRKLGNSGTIVTSYCLGTMTFGAEADEATSHLLLDDYVEAGGNFIDTANVYSLGVSEE   60
SEQ18    MEYRKLGNSGTIVTSYCLGTMTFGAEADEATSHLLLDDYVEAGGNFIDTANVYSLGLSEQ   60
SEQ19    MDYRKLGNSGAVVSNLCLGTMTFGDEADEATSFLLMDQYVEAGGNFLDTADVYSTGVSEE   60
SEQ20    MDYRKLGNSGAVVSNLCLGTMTFGDEADEATSFVLMDQYVEAGGNFLDTADVYSAGLSEE   60
SEQ21    MDYRKLGNSGAVVSNLCLGTMTFGDEADEATSFLLMDQYVEAGGNFLDTADVYSTGVSEE   60
SEQ22    MDYRKLGNSGAVVSNLCLGTMTFGDEADEATSFVLMDQYVEAGGNFLDTADVYSAGLSEE   60
SEQ23    MDYRKLGNSGAVVSNLCLGTMTFGDEADEATSFLLMDQYVEAGGNFLDTADVYSAGVSEE   60
SEQ24    MDYRKLGNSGAVVSNLCLGTMTFGDEADEATSFVLMDQYVEAGGNFLDTADVYSTGLSEE   60
SEQ25    MDYRKLGNSGAVVSNLCLGTMTFGDEADEATSFLLMDQYVEAGGNFLDTADVYSAGLSEE   60
SEQ26    MDYRKLGNSGAVVSNLCLGTMTFGDEADEATSFLLMDQYVEAGGNFLDTADVYSTGVSEE   60
SEQ27    MDYRKLGNSGAVVSNLCLGTMTFGDEADEATSFLLMDQYVEAGGNFLDTADVYSTGLSEE   60
SEQ28    MDYRKLGNSGAVVSNLCLGTMTFGDEADEATSFVLMDQYVEAGGNFLDTADVYSTGVSEE   60
```

FIGURE 1 CONT'D

| | | |
|---|---|---|
| SEQ1 | IIGNWLKAKPGRELNLVIASKGRFPMGNGPNDLGLSRKHLGAALDASLKRLGVERIDLYQ | 120 |
| SEQ2 | IVGRWLKARPEAASQVVLATKGRFPMGAGPNDIGLSRKHLNRALEDSLRRLGVEQIDLYQ | 120 |
| SEQ3 | IVGRWLKGKK--LRDLVIATKGRFPMGQGPNHLGLSRKHLGEALDASLQRLGVEQIDLYQ | 118 |
| SEQ4 | IIGRWLKDKPGRAQNLVIATKGRFPMGQGPNDLGLSRKHLGAALDASLKRLGVEQIDLYQ | 120 |
| SEQ5 | IVGRWLKTKPTGLRDLVITTKGRFPMGDGPNHLGLSRKNLREALDASLKRLGVEHIDLYQ | 120 |
| SEQ6 | IVGRWLKARPEAARQVLITTKARFPMGSGPNDLGLSRRHLNQALDASLGRLGVEHIDLYQ | 120 |
| SEQ7 | IIGGWLKSKPGILRDLVITTKGRFPMGDGPNHLGLSRKNLSEALDASLKRLGVEHIDLYQ | 120 |
| SEQ8 | IIGRWLKAKPEAASNLVIASKGRFPMGAGPNDLGLSRKHLNRALDDSLKRLGVEQIDLYQ | 120 |
| SEQ9 | IVGRWLKARPEAASQVVLASKGRFPMGAGPNDLGLSRKHLNRALDDSLKRLGVEQIDLYQ | 120 |
| SEQ10 | IIGRWLKAKPEAASQVVIASKGRFPMGAGPNDLGLSRKHLNRALDDSLRRLGVEQIDLYQ | 120 |
| SEQ11 | IIGRWLKARPEAASNVVLASKGRFPMGAGPNDLGLSRKHLNRALEDSLKRLGVEQIDLYQ | 120 |
| SEQ12 | IIGRWLKAKPEAASNLVIASKGRFPMGAGPNDLGLSRKHLNRALDDSLKRLGVEQIDLYQ | 120 |
| SEQ13 | IIGRWLKARPEAASNVVIATKGRFPMGAGPNDLGLSRKHLNRALEDSLKRLGVEQIDLYQ | 120 |
| SEQ14 | IIGRWLKARPEAASNVVLATKGRFPMGAGPNDLGLSRKHLNRALEDSLKRLGVEQIDLYQ | 120 |
| SEQ15 | IVGRWLKARPEAASQVVLATKGRFPMGAGPNDIGLSRKHLNRALEDSLRRLGVEQIDLYQ | 120 |
| SEQ16 | IIGRWLKAKPEAASNLVIASKGRFPMGAGPNDLGLSRKHLNRALDDSLKRLGVEQIDLYQ | 120 |
| SEQ17 | IIGRWLKAKPEAASNLVIASKGRFPMGAGPNDLGLSRKHLNRALDDSLKRLGVEQIDLYQ | 120 |
| SEQ18 | IIGRWLKAKPEAASQVVIASKGRFPMGAGPNDLGLSRKHLNRALDDSLKRLGVEQIDLYQ | 120 |
| SEQ19 | IIGRWLKAKR--LRNLVIASKGRFPMGNGPNHLGLSRKHLGEALDASLQRLGVEQIDLYQ | 118 |
| SEQ20 | IVGRWLKGKK--LRDLVIATKGRFPMGNGPNHLGLSRKHLGEALDASLQRLGVEQIDLYQ | 118 |
| SEQ21 | IIGRWLKGKK--LRDLVIATKGRFPMGQGPNHLGLSRKHLGEALDASLQRLGVEQIDLYQ | 118 |
| SEQ22 | IIGRWLKAKR--LRNLVIASKGRFPMGNGPNHLGLSRKHLGEALDASLQRLGVEQIDLYQ | 118 |
| SEQ23 | IVGRWLKAKK--LRNLVIATKGRFPMGNGPNHLGLSRKHLGEALDASLQRLGVEQIDLYQ | 118 |
| SEQ24 | IIGRWLKGKR--LRDLVIASKGRFPMGQGPNHLGLSRKHLGEALDASLQRLGVEQIDLYQ | 118 |
| SEQ25 | IIGRWLKAKR--LRDLVIATKGRFPMGNGPNHLGLSRKHLGEALDASLQRLGVEQIDLYQ | 118 |
| SEQ26 | IVGRWLKGKK--LRDLVIATKGRFPMGQGPNHLGLSRKHLGEALDASLQRLGVEQIDLYQ | 118 |
| SEQ27 | IIGRWLKAKK--LRDLVIASKGRFPMGNGPNHLGLSRKHLGEALDASLQRLGVEQIDLYQ | 118 |
| SEQ28 | INGRWLKGKK--LRDLVIATKGRFPMGNGPNHLGLSRKHLGEALDASLQRLGVEQIDLYQ | 118 |

| | | |
|---|---|---|
| SEQ1 | MHAFDALTPMDETLRFLDDSIRNGKIAYYGFSNFTGWQLTKAVYLAKLNGYQPPVTLQPQ | 180 |
| SEQ2 | MHAWDALTPIEETLRFLDDAVGAGKIAYYGFSNYLGWQVTKAVHVAKANHWSAPVTLQPQ | 180 |
| SEQ3 | MHAWDALTPLEETLRFLDDAVRSGKIAYYGFSNFLGWHITKAVWMARAQGYAAPVTLQPQ | 178 |
| SEQ4 | MHAFDVLTPLEETLRFLDDSIRNGKIAYYGFSNFTGWQLTKAVWLAKLNGYQPPVTLQPQ | 180 |
| SEQ5 | MHAFDALTPLEETLRFLDDSIRNGKIAYYGFSNFLGWQLTKAVWIARANGYQPPVTLQPQ | 180 |
| SEQ6 | MHAFDALTPLEETLRFLDDAIRNGKIGYYGFSNFIGWQLTKATWIAKAGGLAPPITLQPH | 180 |
| SEQ7 | LHAFDALTPIEETLRFLDDSIRNGKIAYYGFSNFLGWQMTKAVWIAKAGNFQPPVTLQPQ | 180 |
| SEQ8 | MHAWDALTPIEETLRFLDDSIGAGKIAYYGFSNYLGWQVTKAVHVAKANHWSAPVTLQPQ | 180 |
| SEQ9 | MHAWDALTPIEETLRFLDDSIGAGKIAYYGFSNYLGWQLTKAVHLAKLNHWSAPVTLQPQ | 180 |
| SEQ10 | MHAWDALTPIEETLRFLDDSIGAGKIAYYGFSNYLGWQLTKAVHLAKLNHWSAPVTLQPQ | 180 |
| SEQ11 | MHAWDALTPIEETLRFLDDAVGAGKIAYYGFSNYLGWQLTKAVHLAKANHWSAPVTLQPQ | 180 |
| SEQ12 | MHAWDALTPIEETLRFLDDAVGAGKIAYYGFSNYLGWQLTKAVHLAKLNHWSAPVTLQPQ | 180 |
| SEQ13 | MHAWDALTPIEETLRFLDDAIGAGKIAYYGFSNYLGWQVTKAVHLAKANHWSAPVTLQPQ | 180 |
| SEQ14 | MHAWDALTPIEETLRFLDDSVGAGKIAYYGFSNYLGWQVTKAVHLAKANHWSAPVTLQPQ | 180 |
| SEQ15 | MHAWDALTPIEETLRFLDDSIGAGKIAYYGFSNYLGWQLTKAVHLAKLNHWSAPVTLQPQ | 180 |
| SEQ16 | MHAWDALTPIEETLRFLDDAVGAGKIAYYGFSNYLGWQVTKAVHVAKANHWSAPVTLQPQ | 180 |
| SEQ17 | MHAWDALTPIEETLRFLDDAVGAGKIAYYGFSNYLGWQVTKAVHVAKANHWSAPVTLQPQ | 180 |
| SEQ18 | MHAWDALTPIEETLRFLDDAVGAGKIAYYGFSNYLGWQLTKAVHVAKANHWSAPVTLQPQ | 180 |
| SEQ19 | MHAWDALTPLEETLRFLDDSIRSGKIAYYGFSNFLGWHLTKAVWMAKLNGYAAPVTLQPQ | 178 |
| SEQ20 | MHAWDALTPLEETLRFLDDSIRSGKIAYYGFSNFLGWHLTKAVWMAKLNGYAAPVTLQPQ | 178 |
| SEQ21 | MHAWDALTPLEETLRFLDDSIRSGKIAYYGFSNFLGWHLTKAVWMAKLNGYAAPVTLQPQ | 178 |
| SEQ22 | MHAWDALTPLEETLRFLDDAIRSGKIAYYGFSNFLGWHITKAVWMARAQGYAAPVTLQPQ | 178 |
| SEQ23 | MHAWDALTPLEETLRFLDDAIRSGKIAYYGFSNFLGWHITKAVWMAKANGYAAPVTLQPQ | 178 |
| SEQ24 | MHAWDALTPLEETLRFLDDSVRSGKIAYYGFSNFLGWHLTKAVWMARLQGYAAPVTLQPQ | 178 |
| SEQ25 | MHAWDALTPLEETLRFLDDAVRSGKIAYYGFSNFLGWHLTKAVWMAKAQGYAAPVTLQPQ | 178 |
| SEQ26 | MHAWDALTPLEETLRFLDDAVRSGKIAYYGFSNFLGWHLTKAVWMAKLNGYAAPVTLQPQ | 178 |
| SEQ27 | MHAWDALTPLEETLRFLDDSIRSGKIAYYGFSNFLGWHLTKAVWMARANGYAAPVTLQPQ | 178 |
| SEQ28 | MHAWDALTPLEETLRFLDDSIRSGKIAYYGFSNFLGWHLTKAVWMAKLNGYAAPVTLQPQ | 178 |

FIGURE 1 CONT'D

```
SEQ1    YNLLVRDIEHEIVPASLDAQIGLLPWSPLGGGWLSGKYKRDQAPSGATRLGENPKRGMEA   240
SEQ2    YNLLVRDIEHEIVPACLDAGMGLLPWSPLGGGWLAGKYQRDVMPSGATRLGENPNRGMES   240
SEQ3    YNLLVRDIEHEVVPACEDAGMGLLPWSPLGGGWLSGKYKRDQMPEGATRLGENPKRGMEA   238
SEQ4    YSLLVRDIEHEIVPASLDAGIGLLPWSPLGGGWLSGKYKRDQMPTGATRLGENPKRGMEA   240
SEQ5    YNLLVRDIEHEIVPASLDAGIGLLPWSPLGGGWLSGKYRRDEMPTGATRLGENPKRGGEA   240
SEQ6    YNLLVRDIEHEIVPAALDADIGLLPWSPLGGGWLTGKYKRDQLPTGATRLGENPNRGQES   240
SEQ7    YNLLARDIEHEVVPAALDAGIGLLPWSPLGGGWLSGKYKRDQMPSGATRLGENPKRGLEA   240
SEQ8    YNLLVRDIEHEIVPACLDAGMGLLPWSPLGGGWLAGKYQRDVMPSGATRLGENPNRGMES   240
SEQ9    YNLLVRDIEHEIVPACLDAGMGLLPWSPLGGGWLAGKYQRDVMPSGATRLGENPNRGMES   240
SEQ10   YNLLVRDIEHEIVPACLDAGMGLLPWSPLGGGWLSGKYQRDVMPSGATRLGENPNRGMES   240
SEQ11   YNLLVRDIEHEIVPACLDAGMGLLPWSPLGGGWLAGKYQRDVMPSGATRLGENPNRGMEA   240
SEQ12   YNLLVRDIEHEIVPACLDAGMGLLPWSPLGGGWLAGKYQRDVMPSGATRLGENPNRGMES   240
SEQ13   YNLLVRDIEHEIVPACLDAGMGLLPWSPLGGGWLSGKYQRDVMPSGATRLGENPNRGMEA   240
SEQ14   YNLLVRDIEHEIVPACLDAGMGLLPWSPLGGGWLSGKYQRDVMPSGATRLGENPNRGMEA   240
SEQ15   YNLLVRDIEHEIVPACLDAGMGLLPWSPLGGGWLSGKYQRDVMPSGATRLGENPNRGMES   240
SEQ16   YNLLVRDIEHEIVPACLDAGMGLLPWSPLGGGWLAGKYQRDVMPSGATRLGENPNRGMEA   240
SEQ17   YNLLVRDIEHEIVPACLDAGMGLLPWSPLGGGWLSGKYQRDVMPSGATRLGENPNRGMES   240
SEQ18   YNLLARDIEHEIVPACLDAGMGLLPWSPLGGGWLAGKYQRDVMPTGATRLGENPNRGMEA   240
SEQ19   YNLLVRDIEHEVVPACEDAGMGLLPWSPLGGGWLSGKYKRDQMPEGATRLGENPKRGMEA   238
SEQ20   YNLLVRDIEHEVVPACEDAGMGLLPWSPLGGGWLSGKYKRDQMPEGATRLGENPKRGMEA   238
SEQ21   YNLLVRDIEHEVVPACEDAGMGLLPWSPLGGGWLSGKYKRDQMPEGATRLGENPKRGMEA   238
SEQ22   YNLLVRDIEHEVVPACEDAGMGLLPWSPLGGGWLSGKYKRDQMPEGATRLGENPKRGMEA   238
SEQ23   YNLLVRDIEHEVVPACEDAGMGLLPWSPLGGGWLSGKYKRDQMPEGATRLGENPKRGMEA   238
SEQ24   YNLLVRDIEHEVVPACEDAGMGLLPWSPLGGGWLSGKYKRDQMPEGATRLGENPKRGMEA   238
SEQ25   YNLLVRDIEHEVVPACEDAGMGLLPWSPLGGGWLSGKYKRDQMPEGATRLGENPKRGMEA   238
SEQ26   YNLLVRDIEHEVVPACEDAGMGLLPWSPLGGGWLSGKYKRDQMPEGATRLGENPKRGMEA   238
SEQ27   YNLLVRDIEHEVVPACEDAGMGLLPWSPLGGGWLSGKYKRDQMPEGATRLGENPKRGMEA   238
SEQ28   YNLLVRDIEHEVVPACEDAGMGLLPWSPLGGGWLSGKYKRDQMPEGATRLGENPKRGMEA   238

SEQ1    FEARNAKDATWSIIGAVEDIAKAHNVSMAQVALAWVVAQPAVTSVILGARTREQLADNLK   300
SEQ2    FGPRNAQERTWQIIDAVAEIAKDRGASAAQVALAWVEARPAVTSVILGARTREQLADNLG   300
SEQ3    YEGRNAQERTWAIIGAVEDIAKAQDVTMAQVALAWTAARPAVTSVILGARTAEQLKDNLG   298
SEQ4    FEARNAKDSTWAVIGAVEDIAKARGVSMAQVALAWVAAQPAVASVILGARTQEQLADNLK   300
SEQ5    YERRNAKSATWDIIGVVEDVAKTRGVSMAQVALAWVAQRPAVTSVILGARTTEQLKDNLG   300
SEQ6    YGPRNEQERTWRIIAAVEAVAKALGVSMAQVALAWLADRPAVTSVILGARTREQLADNLA   300
SEQ7    FEKRNANPATWQVIGALEDIAKARGASMAQVALAWLVKRPAVTSVILGARTAEQLADNLG   300
SEQ8    FGPRNAQERTWQIIDAVAEIAKDRGASAAQVALAWVEARPAVTSVILGARTREQLADNLG   300
SEQ9    FGPRNAQDRTWQIIDAVADIAKDRGVSAAQVALAWVEARPAVTSVILGARTREQLADNLG   300
SEQ10   FGPRNAQERTWQIIDAVAEIAKDRGASAAQVALAWVEARPAVTSVILGARTREQLADNLG   300
SEQ11   FGPRNAQDRTWQIIDAVADIAKDRGVSAAQVALAWVEARPAVTSVILGARTREQLADNLG   300
SEQ12   FGPRNAQDRTWQIIDAVADIAKDRGVSAAQVALAWVEARPAVTSVILGARTREQLADNLG   300
SEQ13   FGPRNAQDRTWQIIDAVAEIAKDRGVSAAQVALAWVEARPAVTSVILGARTREQLADNLG   300
SEQ14   FGPRNAQDRTWQIIDAVAEIAKDRGVSAAQVALAWVEARPAVTSVILGARTREQLADNLG   300
SEQ15   FGPRNAQERTWQIIDAVAEIAKDRGASAAQVALAWVEARPAVTSVILGARTREQLADNLG   300
SEQ16   FGPRNAQDRTWQIIDAVADIAKDRGVSAAQVALAWVEARPAVTSVILGARTREQLADNLG   300
SEQ17   FGPRNAQDRTWQIIDAVAEIAKDRGVSAAQVALAWVEARPAVTSVILGARTREQLADNLG   300
SEQ18   FGPRNAQERTWQIIDAVAEIAKDRGASAAQVALAWVEARPAVTSVILGARTREQLADNLG   300
SEQ19   YEGRNAQDRTWSIIGAVEDIAKAQDVTMAQVALAWTAARPAVTSVILGARTAEQLKDNLG   298
SEQ20   YEGRNAQDRTWSIIGAVEDIAKAQNVSMAQVALAWTVARPAVTSVILGARTAEQLKDNLG   298
SEQ21   YEGRNAQDRTWSIIGAVEDIAKAQDVTMAQVALAWTAARPAVTSVILGARTAEQLKDNLG   298
SEQ22   YEGRNAQDRTWSIIGAVEDIAKAQNVSMAQVALAWTAARPAVTSVILGARTAEQLKDNLG   298
SEQ23   YEGRNAQERTWSIIGAVEDIAKAQDVSMAQVALAWTAARPAVTSVILGARTAEQLKDNLG   298
SEQ24   YEGRNAQDRTWAIIGAVEDIAKAQNVTMAQVALAWTVARPAVTSVILGARTAEQLKDNLG   298
SEQ25   YEGRNAQDRTWAIIGAVEDIAKAQDVSMAQVALAWTVARPAVTSVILGARTAEQLKDNLG   298
SEQ26   YEGRNAQERTWAIIGAVEDIAKAQDVTMAQVALAWTVARPAVTSVILGARTAEQLKDNLG   298
SEQ27   YEGRNAQDRTWSIIGAVEDIAKAQDVTMAQVALAWTVARPAVTSVILGARTAEQLKDNLG   298
SEQ28   YEGRNAQERTWAIIGAVEDIAKAQDVTMAQVALAWTAARPAVTSVILGARTAEQLKDNLG   298
```

FIGURE 1 CONT'D

```
SEQ1    SVSLKLSAADLATLSEASKPAMSDYPYGAGGINQRHRKLEGGR  343
SEQ2    SSKVKLSAEETDKLTRISMPQMSDYPYGERGVSQRFRKMEGGR  343
SEQ3    AADLVLSEADMERLNAVSAPQMADYPYGTGGIGQRNRKIEGGR  341
SEQ4    SAALKLSAGDLQTLGDVSKPVMADYPYGTGGINQRNRNIEGGR  343
SEQ5    AIDLALSTEEIEKLNAASKPAVGDYPYGAGGINQRNRKIEGGR  343
SEQ6    AADLRLDAEHAQQLTDASAPEVADYPYGKGGVNQRHRKIAGGR  343
SEQ7    AADVTLSDDEMRTLTEMSAPQVADYPYGEGGNRQRNRRMEGGR  343
SEQ8    SSKVKLSAEETDKLTRISMPQMSDYPYGERGVSQRFRKMEGGR  343
SEQ9    SSKLKLSAEDTDKLSRASMPQMSDYPYGERGISQRFRKMEGGR  343
SEQ10   SSKVKLSAEETDKLTRISMPQMSDYPYGERGVSQRFRKMEGGR  343
SEQ11   SSKLKLSAEDTDKLSRISMPQMSDYPYGERGISQRFRKMEGGR  343
SEQ12   SSKVKLSAEETDKLTRISMPQMSDYPYGERGVSQRFRKMEGGR  343
SEQ13   SSKVKLSAEDTDKLTRASMPQMSDYPYGERGVSQRFRKMEGGR  343
SEQ14   SSKVKLSAEDTDKLTRASMPQMSDYPYGERGVSQRFRKMEGGR  343
SEQ15   SSKSKLSAEDTDKLTRISMPQMSDYPYGERGISQRFRKMEGGR  343
SEQ16   SSKVKLSAEETDKLTRISMPQMSDYPYGERGVSQRFRKMEGGR  343
SEQ17   SSKLKLSAEETDKLTRISMPQMSDYPYGERGVSQRFRKMEGGR  343
SEQ18   SVKVKLSAEETDKLTRISMPQMSDYPYGERGVSQRFRRMEGGR  343
SEQ19   AADLVLSEADMERLNAVSAPQMADYPYGTGGIGQRNRKIEGGR  341
SEQ20   SVDLVLSEADMERLNAASAPQMSDYPYGTGGIGQRNRKLEGGR  341
SEQ21   SVDLVLSEADMERLNAASAPQMSDYPYGTGGIGQRNRKLEGGR  341
SEQ22   SVDLVLSEADMERLNAASAPQMSDYPYGTGGIGQRNRKLEGGR  341
SEQ23   SADLVLSEADMERLNAASAPQMADYPYGTGGIGQRNRKLEGGR  341
SEQ24   AVDLVLSEADMERLNAVSAPQMSDYPYGTGGIGQRNRKIEGGR  341
SEQ25   SADLVLSEADMERLNAVSAPQMSDYPYGTGGIGQRNRKLEGGR  341
SEQ26   SVDLVLSEADMERLNAASAPQMADYPYGTGGIGQRNRKIEGGR  341
SEQ27   AADLVLSEADMERLNAVSAPQMADYPYGTGGIGQRNRKIEGGR  341
SEQ28   AVDLVLSEADMERLNAASAPQMSDYPYGTGGIGQRNRKIEGGR  341
```

FIGURE 2

| | SEQ1 | SEQ2 | SEQ3 | SEQ4 | SEQ5 | SEQ6 | SEQ7 | SEQ8 | SEQ9 | SEQ10 |
|---|---|---|---|---|---|---|---|---|---|---|
| **SEQ1** | 100.0 | 72.6 | 76.5 | 88.1 | 79.0 | 73.5 | 76.7 | 77.6 | 77.6 | 76.4 |
| **SEQ2** | 72.6 | 100.0 | 72.7 | 72.3 | 71.4 | 72.3 | 72.3 | 95.0 | 95.0 | 96.2 |
| **SEQ3** | 76.5 | 72.7 | 100.0 | 80.7 | 81.2 | 75.4 | 77.7 | 74.8 | 73.3 | 73.0 |
| **SEQ4** | 88.1 | 72.3 | 80.7 | 100.0 | 81.1 | 75.8 | 77.8 | 76.7 | 76.1 | 75.5 |
| **SEQ5** | 79.0 | 71.4 | 81.2 | 81.1 | 100.0 | 77.6 | 81.3 | 74.6 | 73.8 | 73.2 |
| **SEQ6** | 73.5 | 72.3 | 75.4 | 75.8 | 77.6 | 100.0 | 73.5 | 73.2 | 72.6 | 72.6 |
| **SEQ7** | 76.7 | 72.3 | 77.7 | 77.8 | 81.3 | 73.5 | 100.0 | 74.6 | 72.3 | 74.3 |
| **SEQ8** | 77.6 | 95.0 | 74.8 | 76.7 | 74.6 | 73.2 | 74.6 | 100.0 | 93.6 | 96.5 |
| **SEQ9** | 77.6 | 95.0 | 73.3 | 76.1 | 73.8 | 72.6 | 72.3 | 93.6 | 100.0 | 95.9 |
| **SEQ10** | 76.4 | 96.2 | 73.0 | 75.5 | 73.2 | 72.6 | 74.3 | 96.5 | 95.9 | 100.0 |
| **SEQ11** | 77.6 | 95.0 | 74.5 | 76.4 | 73.5 | 72.0 | 72.3 | 94.2 | 97.1 | 94.2 |
| **SEQ12** | 77.0 | 95.6 | 73.6 | 76.1 | 73.2 | 71.7 | 73.8 | 95.9 | 96.5 | 97.1 |
| **SEQ13** | 77.3 | 95.3 | 74.5 | 76.7 | 73.8 | 73.2 | 73.5 | 95.6 | 95.0 | 95.0 |
| **SEQ14** | 76.7 | 95.9 | 73.9 | 76.1 | 73.5 | 72.3 | 74.1 | 95.0 | 95.6 | 95.6 |
| **SEQ15** | 76.7 | 95.6 | 74.5 | 76.4 | 73.8 | 73.5 | 72.3 | 95.3 | 95.0 | 95.9 |
| **SEQ16** | 76.4 | 96.2 | 74.2 | 75.5 | 73.5 | 71.4 | 74.3 | 96.5 | 95.3 | 95.9 |
| **SEQ17** | 77.3 | 95.3 | 75.1 | 76.4 | 74.1 | 72.6 | 74.1 | 97.4 | 94.5 | 96.2 |
| **SEQ18** | 74.9 | 95.0 | 73.6 | 74.3 | 72.6 | 72.3 | 75.5 | 95.3 | 93.0 | 95.9 |
| **SEQ19** | 81.2 | 72.4 | 95.0 | 82.4 | 80.9 | 74.8 | 77.7 | 77.1 | 76.3 | 76.0 |
| **SEQ20** | 81.5 | 73.0 | 95.0 | 81.2 | 81.5 | 74.5 | 78.0 | 76.3 | 76.5 | 75.4 |
| **SEQ21** | 81.5 | 73.0 | 95.0 | 81.8 | 81.2 | 73.9 | 77.4 | 76.8 | 76.5 | 76.0 |
| **SEQ22** | 80.9 | 72.7 | 95.3 | 80.4 | 80.7 | 74.5 | 77.1 | 76.8 | 75.4 | 74.8 |
| **SEQ23** | 80.4 | 74.5 | 96.2 | 81.5 | 81.5 | 76.3 | 77.7 | 77.4 | 76.0 | 75.4 |
| **SEQ24** | 79.8 | 71.6 | 96.5 | 80.7 | 80.4 | 73.0 | 77.4 | 75.4 | 74.8 | 74.5 |
| **SEQ25** | 80.1 | 73.9 | 96.2 | 81.2 | 80.4 | 74.8 | 78.3 | 76.5 | 75.4 | 75.1 |
| **SEQ26** | 79.8 | 73.9 | 96.8 | 81.2 | 80.9 | 74.8 | 77.1 | 76.0 | 75.7 | 75.1 |
| **SEQ27** | 80.4 | 72.1 | 96.2 | 80.9 | 81.2 | 74.5 | 78.6 | 76.5 | 75.4 | 75.1 |
| **SEQ28** | 80.1 | 72.7 | 96.2 | 81.2 | 81.8 | 74.8 | 77.4 | 76.3 | 75.7 | 75.4 |

FIGURE 2 CONT'D

| | SEQ11 | SEQ12 | SEQ13 | SEQ14 | SEQ15 | SEQ16 | SEQ17 | SEQ18 | SEQ19 | SEQ20 |
|---|---|---|---|---|---|---|---|---|---|---|
| SEQ1 | 77.6 | 77.0 | 77.3 | 76.7 | 76.7 | 76.4 | 77.3 | 74.9 | 81.2 | 81.5 |
| SEQ2 | 95.0 | 95.6 | 95.3 | 95.9 | 95.6 | 96.2 | 95.3 | 95.0 | 72.4 | 73.0 |
| SEQ3 | 74.5 | 73.6 | 74.5 | 73.9 | 74.5 | 74.2 | 75.1 | 73.6 | 95.0 | 95.0 |
| SEQ4 | 76.4 | 76.1 | 76.7 | 76.1 | 76.4 | 75.5 | 76.4 | 74.3 | 82.4 | 81.2 |
| SEQ5 | 73.5 | 73.2 | 73.8 | 73.5 | 73.8 | 73.5 | 74.1 | 72.6 | 80.9 | 81.5 |
| SEQ6 | 72.0 | 71.7 | 73.2 | 72.3 | 73.5 | 71.4 | 72.6 | 72.3 | 74.8 | 74.5 |
| SEQ7 | 72.3 | 73.8 | 73.5 | 74.1 | 72.3 | 74.3 | 74.1 | 75.5 | 77.7 | 78.0 |
| SEQ8 | 94.2 | 95.9 | 95.6 | 95.0 | 95.3 | 96.5 | 97.4 | 95.3 | 77.1 | 76.3 |
| SEQ9 | 97.1 | 96.5 | 95.0 | 95.6 | 95.0 | 95.3 | 94.5 | 93.0 | 76.3 | 76.5 |
| SEQ10 | 94.2 | 97.1 | 95.0 | 95.6 | 95.9 | 95.9 | 96.2 | 95.9 | 76.0 | 75.4 |
| SEQ11 | 100.0 | 96.5 | 96.2 | 96.2 | 94.5 | 96.5 | 95.6 | 94.2 | 76.5 | 75.7 |
| SEQ12 | 96.5 | 100.0 | 95.6 | 95.6 | 93.0 | 98.8 | 97.4 | 95.3 | 76.3 | 75.4 |
| SEQ13 | 96.2 | 95.6 | 100.0 | 97.7 | 95.0 | 96.2 | 96.5 | 93.9 | 76.3 | 76.3 |
| SEQ14 | 96.2 | 95.6 | 97.7 | 100.0 | 95.0 | 96.2 | 95.9 | 93.9 | 75.7 | 75.7 |
| SEQ15 | 94.5 | 93.0 | 95.0 | 95.0 | 100.0 | 91.8 | 93.6 | 92.4 | 76.3 | 76.8 |
| SEQ16 | 96.5 | 98.8 | 96.2 | 96.2 | 91.8 | 100.0 | 98.0 | 95.9 | 76.0 | 75.1 |
| SEQ17 | 95.6 | 97.4 | 96.5 | 95.9 | 93.6 | 98.0 | 100.0 | 95.6 | 76.8 | 76.0 |
| SEQ18 | 94.2 | 95.3 | 93.9 | 93.9 | 92.4 | 95.9 | 95.6 | 100.0 | 74.2 | 74.5 |
| SEQ19 | 76.5 | 76.3 | 76.3 | 75.7 | 76.3 | 76.0 | 76.8 | 74.2 | 100.0 | 95.3 |
| SEQ20 | 75.7 | 75.4 | 76.3 | 75.7 | 76.8 | 75.1 | 76.0 | 74.5 | 95.3 | 100.0 |
| SEQ21 | 76.3 | 76.0 | 76.8 | 76.3 | 76.8 | 75.7 | 76.5 | 74.5 | 97.1 | 97.7 |
| SEQ22 | 76.5 | 75.7 | 76.8 | 75.7 | 75.1 | 76.3 | 77.1 | 75.1 | 95.6 | 96.8 |
| SEQ23 | 76.5 | 75.7 | 77.4 | 76.3 | 76.8 | 76.3 | 77.1 | 74.8 | 96.5 | 96.5 |
| SEQ24 | 75.4 | 75.1 | 74.5 | 74.5 | 74.8 | 74.8 | 75.7 | 74.2 | 96.2 | 96.2 |
| SEQ25 | 77.1 | 76.3 | 76.8 | 76.3 | 76.0 | 76.5 | 77.4 | 75.7 | 95.9 | 96.5 |
| SEQ26 | 76.0 | 75.7 | 76.0 | 75.4 | 76.5 | 75.4 | 76.3 | 74.8 | 95.9 | 96.5 |
| SEQ27 | 76.0 | 75.1 | 75.7 | 75.1 | 75.4 | 75.4 | 76.3 | 74.5 | 98.2 | 95.9 |
| SEQ28 | 75.1 | 74.8 | 75.7 | 75.1 | 76.5 | 74.5 | 75.4 | 73.9 | 96.8 | 97.1 |

FIGURE 2 CONT'D

| | SEQ21 | SEQ22 | SEQ23 | SEQ24 | SEQ25 | SEQ26 | SEQ27 | SEQ28 |
|---|---|---|---|---|---|---|---|---|
| SEQ1 | 81.5 | 80.9 | 80.4 | 79.8 | 80.1 | 79.8 | 80.4 | 80.1 |
| SEQ2 | 73.0 | 72.7 | 74.5 | 71.6 | 73.9 | 73.9 | 72.1 | 72.7 |
| SEQ3 | 95.0 | 95.3 | 96.2 | 96.5 | 96.2 | 96.8 | 96.2 | 96.2 |
| SEQ4 | 81.8 | 80.4 | 81.5 | 80.7 | 81.2 | 81.2 | 80.9 | 81.2 |
| SEQ5 | 81.2 | 80.7 | 81.5 | 80.4 | 80.4 | 80.9 | 81.2 | 81.8 |
| SEQ6 | 73.9 | 74.5 | 76.3 | 73.0 | 74.8 | 74.8 | 74.5 | 74.8 |
| SEQ7 | 77.4 | 77.1 | 77.7 | 77.4 | 78.3 | 77.1 | 78.6 | 77.4 |
| SEQ8 | 76.8 | 76.8 | 77.4 | 75.4 | 76.5 | 76.0 | 76.5 | 76.3 |
| SEQ9 | 76.5 | 75.4 | 76.0 | 74.8 | 75.4 | 75.7 | 75.4 | 75.7 |
| SEQ10 | 76.0 | 74.8 | 75.4 | 74.5 | 75.1 | 75.1 | 75.1 | 75.4 |
| SEQ11 | 76.3 | 76.5 | 76.5 | 75.4 | 77.1 | 76.0 | 76.0 | 75.1 |
| SEQ12 | 76.0 | 75.7 | 75.7 | 75.1 | 76.3 | 75.7 | 75.1 | 74.8 |
| SEQ13 | 76.8 | 76.8 | 77.4 | 74.5 | 76.8 | 76.0 | 75.7 | 75.7 |
| SEQ14 | 76.3 | 75.7 | 76.3 | 74.5 | 76.3 | 75.4 | 75.1 | 75.1 |
| SEQ15 | 76.8 | 75.1 | 76.8 | 74.8 | 76.0 | 76.5 | 75.4 | 76.5 |
| SEQ16 | 75.7 | 76.3 | 76.3 | 74.8 | 76.5 | 75.4 | 75.4 | 74.5 |
| SEQ17 | 76.5 | 77.1 | 77.1 | 75.7 | 77.4 | 76.3 | 76.3 | 75.4 |
| SEQ18 | 74.5 | 75.1 | 74.8 | 74.2 | 75.7 | 74.8 | 74.5 | 73.9 |
| SEQ19 | 97.1 | 95.6 | 96.5 | 96.2 | 95.9 | 95.9 | 98.2 | 96.8 |
| SEQ20 | 97.7 | 96.8 | 96.5 | 96.2 | 96.5 | 96.5 | 95.9 | 97.1 |
| SEQ21 | 100.0 | 95.6 | 96.5 | 96.2 | 95.9 | 97.7 | 96.5 | 98.0 |
| SEQ22 | 95.6 | 100.0 | 96.8 | 95.9 | 96.8 | 93.8 | 95.6 | 94.7 |
| SEQ23 | 96.5 | 96.8 | 100.0 | 92.7 | 96.5 | 96.5 | 95.9 | 95.9 |
| SEQ24 | 96.2 | 95.9 | 92.7 | 100.0 | 96.2 | 96.2 | 96.8 | 96.5 |
| SEQ25 | 95.9 | 96.8 | 96.5 | 96.2 | 100.0 | 95.9 | 96.5 | 95.0 |
| SEQ26 | 97.7 | 93.8 | 96.5 | 96.2 | 95.9 | 100.0 | 95.9 | 97.7 |
| SEQ27 | 96.5 | 95.6 | 95.9 | 96.8 | 96.5 | 95.9 | 100.0 | 96.2 |
| SEQ28 | 98.0 | 94.7 | 95.9 | 96.5 | 95.0 | 97.7 | 96.2 | 100.0 |

FIGURE 3

| Enzyme | (specific) activity µmol product/1 min/1 mg of polypeptide | | activity ratio | % stereoselectivity | | Stereo-selectivity ratio |
|---|---|---|---|---|---|---|
| | 3ED | DON | DON:3ED | 3ED | DON | 3ED:DON |
| DmDepB | 0.0236 | 0.000939 | 0.0398 | 96.17 | 3.83 | 25.1:1 |
| RlDepB | 0.0485 | 0.013437 | 0.2769 | 78.31 | 21.69 | 3.61:1 |
| SEQ ID NO: 1 | 0.1159 | 0.020527 | 0.1772 | 84.95 | 15.05 | 5.64:1 |
| SEQ ID NO: 2 | 0.4833 | 0.035157 | 0.0727 | 93.22 | 6.78 | 13.75:1 |
| SEQ ID NO: 3 | 1.1589 | 0.155317 | 0.1340 | 88.18 | 11.82 | 7.46:1 |
| SEQ ID NO: 4 | 0.1776 | 0.027424 | 0.1544 | 86.62 | 13.38 | 6.47:1 |
| SEQ ID NO: 5 | 0.0739 | 0.016833 | 0.2279 | 81.44 | 18.56 | 4.39:1 |
| SEQ ID NO: 6 | 0.0761 | 0.015625 | 0.2054 | 82.96 | 17.04 | 4.87:1 |
| SEQ ID NO: 7 | 0.1838 | 0.016844 | 0.0916 | 91.60 | 8.40 | 10.90:1 |
| SEQ ID NO: 8 | 0.4520 | 0.031902 | 0.0706 | 93.41 | 6.59 | 14.17:1 |
| SEQ ID NO: 9 | 0.5473 | 0.038958 | 0.0595 | 94.38 | 5.62 | 16.79:1 |
| SEQ ID NO: 10 | 0.4264 | 0.031448 | 0.0887 | 91.85 | 8.15 | 11.23:1 |
| SEQ ID NO: 11 | 0.5181 | 0.030460 | 0.0758 | 92.95 | 7.05 | 13.18:1 |
| SEQ ID NO: 12 | 0.4251 | 0.031174 | 0.0950 | 91.32 | 8.68 | 10.52:1 |
| SEQ ID NO: 13 | 0.4170 | 0.030309 | 0.0922 | 91.56 | 8.44 | 10.85:1 |
| SEQ ID NO: 14 | 0.4382 | 0.032886 | 0.0719 | 93.29 | 6.71 | 13.90:1 |
| SEQ ID NO: 15 | 0.4206 | 0.032998 | 0.0941 | 91.40 | 8.60 | 10.63:1 |
| SEQ ID NO: 16 | 0.4322 | 0.033332 | 0.0698 | 93.48 | 6.52 | 14.34:1 |
| SEQ ID NO: 17 | 0.5338 | 0.031726 | 0.0608 | 94.27 | 5.73 | 16.45:1 |
| SEQ ID NO: 18 | 0.5559 | 0.030130 | 0.0585 | 94.47 | 5.53 | 17.08:1 |
| SEQ ID NO: 19 | 1.2956 | 0.144243 | 0.1302 | 88.48 | 11.52 | 7.68:1 |
| SEQ ID NO: 20 | 1.2973 | 0.167308 | 0.1321 | 88.33 | 11.67 | 7.57:1 |
| SEQ ID NO: 21 | 1.3032 | 0.172619 | 0.1319 | 88.35 | 11.65 | 7.58:1 |
| SEQ ID NO: 22 | 1.0712 | 0.132113 | 0.1258 | 88.83 | 11.17 | 7.95:1 |
| SEQ ID NO: 23 | 1.3332 | 0.133231 | 0.1255 | 88.85 | 11.15 | 7.97:1 |
| SEQ ID NO: 24 | 1.2519 | 0.178382 | 0.1116 | 89.96 | 10.04 | 8.96:1 |
| SEQ ID NO: 25 | 1.3197 | 0.143296 | 0.1096 | 90.12 | 9.88 | 9.12:1 |
| SEQ ID NO: 26 | 1.3282 | 0.143032 | 0.1332 | 88.25 | 11.75 | 7.51:1 |
| SEQ ID NO: 27 | 1.0758 | 0.143606 | 0.1644 | 85.88 | 14.12 | 6.08:1 |
| SEQ ID NO: 28 | 1.2775 | 0.163471 | 0.1075 | 90.29 | 9.71 | 9.23:1 |

POLYPEPTIDES CAPABLE OF CONVERTING SUBSTRATE 3-KETO-DEOXYNIVALENOL INTO 3-EPI-DEOXYNIVALENOL

PRIORITY CLAIM

This application claims priority to International Application No. PCT/EP2021/065238, filed Jun. 8, 2021, which claims priority to European Application No. 20178702.5, filed Jun. 8, 2020, wherein the contents of said applications are incorporated herein by reference in their entireties.

REFERENCE TO SEQUENCE LISTING

This application contains a Sequence Listing submitted via EFS-Web. The entire contents of the ASCII text file entitled "IPM0142US_Sequence_Listing.txt" created on Dec. 5, 2022, and having a size of 102 kilobytes, is incorporated herein by reference.

TECHNICAL FIELD OF THE INVENTION

The present invention relates to a method of converting 3-keto-DON into 3-epi-DON, a method for reducing the content of DON in a composition comprising DON or of reducing the toxicity of a composition comprising DON as well as a method for converting a trichothecene comprising a 3-oxo group into a trichothecene comprising a 3-hydroxy group using one or more polypeptide(s) comprising or consisting of SEQ ID NO. 1 or a sequence having a sequence identity of at least 72.0% to SEQ ID NO. 1. Also envisioned are feed or food additives or feed or food as well as pharmaceutical compositions comprising one or more polypeptide(s) comprising or consisting of a sequence of SEQ ID NO. 1 or a sequence having a sequence identity of at least 72.0% to SEQ ID NO. 1 as well as the manufacture thereof. Encompassed are further polypeptide(s) comprising or consisting of a sequence of SEQ ID NO. 1 or a sequence having a sequence identity of at least 88.5% to SEQ ID NO. 1. Also envisioned are host cells or plants.

DESCRIPTION

Mycotoxins are secondary metabolites produced by filamentous fungi. One representative of mycotoxins is deoxynivalenol (DON), or vomitoxin a type-B trichotecene, which is produced by a variety of *Fusarium* fungi and can be found throughout the world. These fungi infest cultivated plants, among others, such as various types of grain, wherein the fungal infestation usually occurs before the harvest when the growth of the fungi and/or the mycotoxin production may take place before storage or may even take place after harvest, either prior to storage or under improper storage conditions. In an international study spanning 8 years, a total of 19,757 samples was analyzed from January 2004 to December 2011; 72% of them testing positive for at least one mycotoxin, 39% were found to be co-contaminated, and 56% testing positive for DON (Schatzmayr and Streit (2013)). Trichothecenes and thus also DON have been found in all regions of the world and in all types of grain and feed crops tested, such as corn, soy flour, wheat, wheat bran, DDGS (dried distillers grains with solubles) as well as in finished animal feed mixtures with an incidence of up to 100%.

The primary strategy for reducing trichothecene contamination of foods and animal feed products is to restrict the growth of fungi, for example by maintaining "good agricultural practice". This includes, among other things, ensuring that the seed is free of pests and fungal infestation or that agricultural waste products are removed from the field promptly. In addition, fungal growth in the field can be reduced by the use of fungicides. After the harvest, the harvested material should be stored at a residual moisture level of less than 15% and at a low temperature to prevent the growth of fungi. Likewise, material contaminated by fungal infestation should be removed before further processing. Despite this long list of preventive measures, even in regions with the highest agricultural standards such as North America and Central Europe, up to 68% of the tested samples were found contaminated with DON as a representative of trichothecenes in the years 2004 to 2011 (Schatzmayr and Streit (2013)).

It is known that toxicity of trichothecenes is (at least) partly due to hydroxyl (—OH) group present at the C-3 atom. One of the most abundant trichothecenes having such a 3-hydroxy group is deoxynivalenol (DON).

Yet, the hydroxyl group of DON and other trichothecenes can be present in two isomeric states, namely in S conformation (DON) or the R conformation (3-epi-DON), as discussed in several publications, e.g. He et al. (2015), Payros et al. (2016) and Pierron et al. (2016).

Hassan et al. (2017) claims that the epimerization of DON to 3-epi-DON proceeds via a two-step process through the formation of 3-keto DON. 3-keto DON comprises a 3-oxo group instead of a 3-hydroxy group as present in the isomers. Finally, Carere et al. (2018) identified an enzyme, namely DmDepB from *D. mutans* 17-2-E-8 that performs the reduction from 3-keto-DON into 3-epi-DON and DON. WO2019/046954 describes this very same enzyme as Hassan et al. (2017) and a further DepB enzyme obtained from *Rhizobium leguminosarum* (RlDepB). He et al. (2020) describe similar enzymes, with the difference of having two homologs to DepB, instead of only one (He et al. (2020) "A quinone-dependent dehydrogenase and two NADPH-dependent aldo/keto reductases detoxify deoxynivalenol in wheat via epimerization in a *Devosia* strain." Food Chemistry, 321:126703).

However, there is still a need to provide enzymes which have a better efficiency in converting 3-keto-DON into the non-toxic isomer 3-epi-DON or to convert trichothecenes comprising a 3-oxo group into trichothecenes comprising a 3-hydroxy group in S configuration.

The solution of the present invention is described in the following, exemplified in the examples, illustrated in the Figures and reflected in the claims.

The present invention relates to a method of converting 3-keto-DON into 3-epi-DON, the method comprising contacting one or more polypeptide(s) comprising or consisting of SEQ ID NO. 1 or a sequence having a sequence identity of at least 72.0% (e.g., at least 88.5%, 89%, 90%, 91%, 92%, 93%, 94%, 95%, 96%, 97%, 98% or 99%, preferably at least 88.5%) to SEQ ID NO. 1 with 3-keto DON.

The present invention relates to a method of converting 3-keto-DON into 3-epi-DON, the method comprising contacting one or more polypeptide(s) comprising or consisting of SEQ ID NO. 2 or 3 or a sequence having a sequence identity of at least 88.5% to SEQ ID NO. 2 or 3 with 3-keto DON, respectively.

The present invention also relates to feed or food additives or feed or food comprising one or more polypeptide(s) comprising or consisting of a sequence of SEQ ID NO. 1 or a sequence having a sequence identity of at least 72.0% (e.g., at least 88.5%, 89%, 90%, 91%, 92%, 93%, 94%, 95%, 96%, 97%, 98% or 99%, preferably at least 88.5%) to SEQ ID NO. 1.

The present invention also relates to feed or food additives or feed or food comprising one or more polypeptide(s) comprising or consisting of a sequence of SEQ ID NO. 2 or 3 or a sequence having a sequence identity of at least 88.5% to SEQ ID NO. 2 or 3, respectively.

The present invention further relates to polypeptide(s) comprising or consisting of a sequence of SEQ ID NO. 1, 2 or 3 or a sequence having a sequence identity of at least 88.5% to SEQ ID NO. 1, 2 or 3 wherein the polypeptide is capable of converting the substrate 3-keto-DON into the product 3-epi-DON and optionally into the product DON, respectively.

In addition, the present invention relates to a method of reducing the content of DON in a composition comprising DON or of reducing the toxicity of a composition comprising DON by converting DON into 3-epi-DON, the method comprising a) contacting the composition with an enzyme capable of converting DON into 3-keto DON; and b) subsequently or concurrently contacting the composition with one or more polypeptide(s) comprising or consisting of SEQ ID NO. 1 or a sequence having a sequence identity of at least 72.0% to SEQ ID NO. 1 or subsequently or concurrently contacting the composition with one or more polypeptide(s) comprising or consisting of SEQ ID NO. 2 or 3 or a sequence having a sequence identity of at least 88.5% to SEQ ID NO. 2 or 3, respectively.

Also, the present invention relates to a use of one or more polypeptide(s) as disclosed herein for converting 3-keto-DON into 3-epi-DON and/or into DON.

Further, the present invention relates to a use of one or more polypeptide(s) as disclosed herein in the manufacture of a feed additive or feed composition, a pharmaceutical composition.

The present invention concerns a use of one or more polypeptide(s) as disclosed herein in the manufacture of biogas, bioethanol, or sugar, preferably from sugar cane or sugar beets.

Further, the present invention relates to an additive for use in agrarian compositions comprising 3-keto-DON or DON, the additive comprising one or more polypeptide(s) as disclosed herein.

Also encompassed by the present invention is a method of converting a trichothecene comprising a 3-oxo group into a trichothecene comprising a 3-hydroxy group, the method comprising contacting one or more polypeptide(s) as disclosed herein with a trichothecene comprising a 3-oxo group.

Further, the present invention concerns a host cell comprising one or more polypeptide(s) as disclosed herein.

Also encompassed by the present invention is a plant genetically modified to express one or more polypeptide(s) as disclosed herein.

The present invention also relates to a seed of a plant as disclosed herein.

Further, the present invention relates to a preparation comprising one or more polypeptide(s) as disclosed herein.

In addition, the present invention relates to one or more polypeptide(s) as disclosed herein for use in the prevention and/or treatment of mycotoxicosis. In addition, the present invention relates to one or more polypeptide(s) as disclosed herein for use as a medicament and/or for use in a method of prevention and/or treatment of mycotoxicosis.

Further, the present invention relates to a pharmaceutical composition comprising one or more polypeptides as disclosed herein (e.g., comprising or consisting of a sequence of SEQ ID NO. 1 or a sequence having a sequence identity of at least 88.5% to SEQ ID NO. 1).

The Figures show:

FIG. 1 ClustalO sequence alignment of SEQ ID NO. 1-28.

FIG. 2 ClustalO sequence identities of SEQ ID NO. 1-28.

FIG. 3 shows data for different enzymes of SEQ ID NO. 1-28 as well as prior art enzymes with regard to the enzyme activity as well as stereoselectivity.

It was surprisingly found that reductases of any one of SEQ ID NO. 1-28 convert 3-keto-DON into 3-epi-DON with a higher activity than prior art enzymes. In this conversion a 3-oxo group of trichothecenes (e.g. DON) is converted into a 3-hydroxy group more efficiently compared to prior art enzymes SEQ ID NO. 29 (DmDepB) and SEQ ID NO. 30 (RIDepB). This better activity is shown in the examples. Since most of the trichothecenes share the feature that they comprise a 3-oxo group at position 3 (as will also be discussed later herein) this group can be converted into a 3-hydroxy group, similarly to the reaction seen for DON. The enzymes of any one of SEQ ID NO. 1-28 are thus capable to convert any trichothecenes comprising a 3-oxo group into trichothecenes comprising a hydroxyl group.

Notably, the enzymes of the present invention are also capable of a highly stereoselective conversion. This means that the 3-oxo group is converted into a 3-hydroxy group of a specific isomer with higher efficiency than the other 3-hydroxy isomer. Specifically, as shown in the examples the polypeptides used in the invention can convert the 3-oxo group with higher efficiency into the hydroxyl group in S conformation (e.g. 3-epi-DON) than into the hydroxyl group in R conformation (e.g. DON).

It was further found that the enzymes of any one of SEQ ID NO. 1-28 share sequence identities in specific motifs as shown in the sequence table herein.

The present invention relates to a method of converting 3-keto-DON into 3-epi-DON, the method comprising contacting one or more polypeptide(s) comprising or consisting of SEQ ID NO. 1 or a sequence having a sequence identity of at least 72.0% (e.g., at least 88.5%, 89%, 90%, 91%, 92%, 93%, 94%, 95%, 96%, 97%, 98% or 99%, preferably at least 88.5%) to SEQ ID NO. 1 with 3-keto DON. The present invention relates to a method of converting 3-keto-DON into 3-epi-DON, the method comprising contacting one or more polypeptide(s) comprising or consisting of SEQ ID NO. 2 or 3 or a sequence having a sequence identity of at least 88.5% to SEQ ID NO. 2 or 3 with 3-keto DON, respectively.

The polypeptides of the present invention or used in the present invention are capable of converting or convert the substrate 3-keto-DON into the products 3-epi-deoxynivalenol (abbreviated as 3-epi-DON herein) and deoxynivalenol (abbreviated as DON herein). The reaction described herein is depicted in the reaction scheme below obtained from Hassan et al. (2017) "The enzymatic epimerization of DON by *Devosia mutans* proceeds through the formation of 3-keto-DON intermediate." Scientific Reports 7, article number 6929.

Reaction scheme: Conversion of 3-keto DON into two isomers 3-epi-DON and DON adapted from Hassan et al. (2017)

3-keto DON

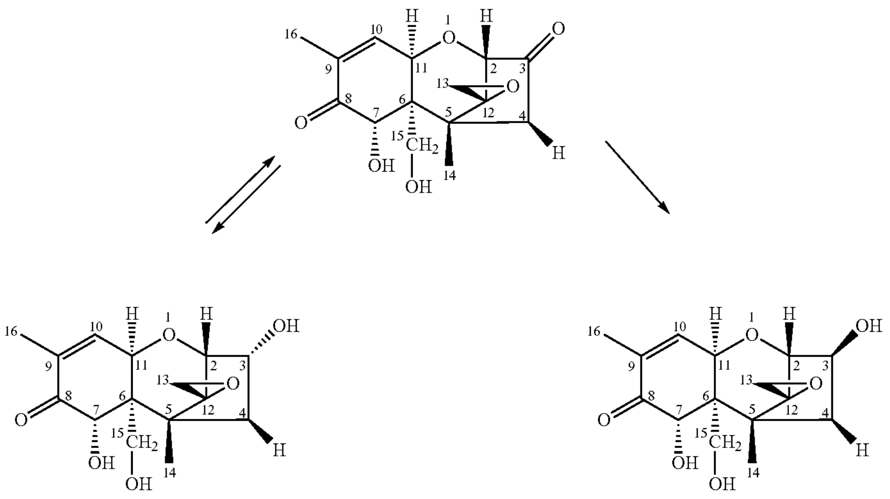

DON 3-epi DON

Reaction scheme: Conversion of 3-keto DON into two isomers 3-epi-DON and DON adapted from Hassan et al. (2017).

As can be seen from the above reaction scheme 3-keto DON can be converted into two isomers, namely DON (R configuration) and 3-epi-DON (S configuration).

The term "polypeptide" when used herein means a peptide, a protein, or a polypeptide, which is used interchangeably and which encompasses amino acid chains of a given length, wherein the amino acid residues are linked by covalent peptide bonds. Also encompassed by the invention are amino acids other than the 20 proteinogenic amino acids of the standard genetic code known to a person skilled in the art, such as selenocysteine. Such polypeptides include any one of SEQ ID NO. 1-28.

The term polypeptide also refers to, and does not exclude, modifications of the polypeptide. Modifications include glycosylation, acetylation, acylation, phosphorylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formulation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination; see, for instance, PROTEINS—STRUCTURE AND MOLECULAR PROPERTIES, 2nd Ed., T. E. Creighton, W. H. Freeman and Company, New York (1993); POST-TRANSLATIONAL COVALENT MODIFICATION OF PROTEINS, B. C. Johnson, Ed., Academic Press, New York (1983), pgs. 1-12; Seifter, Meth. Enzymol. 182 (1990); 626-646, Rattan, Ann. NY Acad. Sci. 663 (1992); 48-62.

It is envisioned that the one or more polypeptide(s) described herein comprise or consist of a sequence having a sequence identity of at least 75.0%, at least 80.0%, at least 83.0%, at least 85.0%, at least 87.0%, at least 88.5%, at least 89.0%, at least 90.0%, at least 91.0%, at least 92.0%, at least 93.0%, at least 94.0%, at least 95.0%, at least 96.0%, at least 97.0%, at least 98.0%, at least 99.0% or more sequence identity to SEQ ID NO. 1.

It is further envisioned that the one or more polypeptide(s) described herein comprise or consist of a sequence having a sequence identity of at least 95.0%, 96.0%, 97.0%, 98.0%, 99.0% or more to any one of SEQ ID NO. 2-28.

Additionally, or alternatively the one or more polypeptide(s) described herein comprise or consist of a sequence having a sequence identity of at least 95.0%, 96.0%, 97.0%, 98.0%, 99.0% or more to any one of SEQ ID NO. 2-7.

Additionally, or alternatively the one or more polypeptide(s) described herein comprise or consist of a sequence having a sequence identity of at least 95.0%, 96.0%, 97.0%, 98.0%, 99.0% or more to any one of SEQ ID NO. 2 or 3, respectively.

It is also contemplated that the one or more polypeptide(s) described herein comprise or consist of a sequence of any one of SEQ ID NO. 1-28.

As described herein the one or more polypeptides may have a certain sequence identity to any one of SEQ ID NO. 1-28. This implicates that these polypeptides can also be fragments and thus comprise amino acid deletions with regard to any one of SEQ ID NO. 1-28.

In accordance with the present invention, the term "identical" or "percent identity" in the context of two or more polypeptide sequences such as SEQ ID NO. 1-28 refers to two or more sequences or subsequences that are the same, or that have a specified percentage of nucleotides that are the same (e.g., at least 85.0%, 88.5%, 89.0%, 90.0%, 91.0%, 92.0%, 93.0%, 94.0%, 95.0%, 96.0%, 97.0%, 98.0% or 99.0% identity), when compared and aligned for maximum correspondence over a window of comparison, or over a designated region as measured using a sequence comparison algorithm as known in the art, or by manual alignment and visual inspection. Sequences having, for example, 80.0% to 95.0% or greater sequence identity are considered to be substantially identical. Such a definition also applies to the complement of a test sequence. Those having skill in the art will know how to determine percent identity between/among sequences using, for example, algorithms such as those based on CLUSTALW computer program (Thompson Nucl. Acids Res. 2 (1994), 4673-4680) or FASTDB (Brutlag Comp. App. Biosci. 6 (1990), 237-245), as known in the art.

Also available to those having skills in this art are the BLAST and BLAST 2.6 algorithms (Altschul Nucl. Acids Res. 25 (1977), 3389-3402). The BLASTP program for amino acid sequences uses as defaults a word size (W) of 6, an expect threshold of 10, and a comparison of both strands. Furthermore, the BLOSUM62 scoring matrix (Henikoff Proc. Natl. Acad. Sci., USA, 89, (1989), 10915; Henikoff and Henikoff (1992) 'Amino acid substitution matrices from protein blocks.' Proc Natl Acad Sci USA. 1992 Nov. 15; 89(22):10915-9) can be used.

For example, BLAST2.6, which stands for Basic Local Alignment Search Tool (Altschul, Nucl. Acids Res. 25 (1997), 3389-3402; Altschul, J. Mol. Evol. 36 (1993), 290-300; Altschul, J. Mol. Biol. 215 (1990), 403-410), can be used to search for local sequence alignments.

It is also contemplated that the one or more polypeptide(s) described herein can be a reductase. For example, the polypeptide(s) can be an aldo-keto red uctase.

It is further envisioned that the one or more polypeptide(s) described herein comprises one or more of the following polypeptide sequences:

(i)
(SEQ ID NO. 31)
YRKLGNSG;

(ii)
(SEQ ID NO. 32)
LGTMTFG;

(iii)
(SEQ ID NO. 33)
AGGNF$X_1$DTA$X_2$VYS, wherein $X_1$ is I or L and $X_2$ is N or D;

(iv)
(SEQ ID NO. 34)
ETLRFLDD;

-continued (v)
(SEQ ID NO. 35)
GKI$X_3$YYGFSN, wherein $X_3$ is A or G;

(vi)
(SEQ ID NO. 36)
RDIEHE$X_4$VPA, wherein $X_4$ is I or V;

(vii)
(SEQ ID NO. 37)
GLLPWSPLGGGWL;

(viii)
(SEQ ID NO. 38)
GATRLGENP;

(ix)
(SEQ ID NO. 39)
AQVALAW;
and/or (x)
(SEQ ID NO. 40)
PAV$X_5$SVILGART, wherein $X_5$ is T or A.

It is contemplated that the one or more polypeptide(s) described herein comprises 1, 2, 3, 4, 5, 6, 7, 8, 9 or 10 of the peptide sequences shown in (i)-(x). Preferably, the polypeptide(s) comprise all of the peptide sequences shown in (i)-(x).

It is further envisioned that the one or more polypeptide(s) comprising a sequence having a sequence identity of at least 72.0% (e.g., at least 88.5%, 89%, 90%, 91%, 92%, 93%, 94%, 95%, 96%, 97%, 98% or 99%, preferably at least 88.5%) to SEQ ID NO. 1 comprises one or more amino acid substitutions compared to a sequence of SEQ ID NO. 1.

It is further envisioned that the one or more polypeptide(s) comprising a sequence having a sequence identity of at least 88.5% to SEQ ID NO. 2 or 3 comprises one or more amino acid substitutions compared to a sequence of SEQ ID NO. 2 or 3, respectively.

It is also contemplated that the one or more amino acid substitutions comprise or consist of conservative amino acid substitutions, preferably a highly conservative amino acid substitution.

As used herein, "conservative" substitutions mean substitutions as listed as "Exemplary Substitutions" in Table 1 below. "Highly conservative" substitutions as used herein mean substitutions as shown under the heading "Preferred Substitutions" in Table 1 below.

TABLE 1

Conservative amino acid substitutions.

| Original | Exemplary substitution(s) - conservative | Preferred substitution(s) - conservative |
|---|---|---|
| Ala (A)<br>(neutral and small) | Val (V)<br>(non-polar and small)<br>Leu (L)<br>(nonpolar and relatively small)<br>Ile (I)<br>(nonpolar and relatively small)<br>Gly (G)<br>(neutral and small) | Val (V)<br>(nonpolar relatively small)<br>Gly (G)<br>(neutral and small) |
| Arg (R)<br>(polar and relatively large) | Lys (K)<br>(polar and relatively large)<br>Gln (Q)<br>(polar and relatively small)<br>Asn (N)<br>(polar and relatively small) | Lys (K)<br>(polar and relatively large) |
| Asn (N)<br>(polar and relatively small) | Gln (Q)<br>(polar and relatively small)<br>His (H)<br>(polar and relatively large) | Gln (Q)<br>(polar and relatively small) |

TABLE 1-continued

| Conservative amino acid substitutions. | | |
|---|---|---|
| Original | Exemplary substitution(s) - conservative | Preferred substitution(s) - conservative |
| | Asp (D)<br>(polar and relatively small)<br>Lys (K)<br>(polar and relatively large)<br>Arg (R)<br>(polar and relatively large) | |
| Asp (D)<br>(negative charged side chain) | Glu (E)<br>(polar and relatively small)<br>Asn (N)<br>(polar and relatively small) | Glu (E)<br>(polar and relatively small) |
| Cys (C)<br>(special) | Ser (S)<br>(neutral and small)<br>Ala (A)<br>(neutral and small) | Ser (S)<br>(neutral and small) |
| Gln (Q)<br>(polar and relatively small) | Asn (N)<br>(polar and relatively small)<br>Glu (E)<br>(polar and relatively small) | Asn (N)<br>(polar and relatively small) |
| Glu (E)<br>(polar and relatively small) | Asp (D)<br>(polar and relatively small)<br>Gln (Q)<br>(polar and relatively small) | Asp (D)<br>(polar and relatively small) |
| Gly (G)<br>(neutral and small) | Ala (A)<br>(neutral and small) | Ala (A)<br>(neutral and small) |
| His (H)<br>(polar and relatively large) | Asn (N)<br>(polar and relatively small)<br>Gln (Q)<br>(polar and relatively small)<br>Lys (K)<br>(polar and relatively large)<br>Arg (R)<br>(polar and relatively large) | Arg (R)<br>(polar and relatively large) |
| Ile (I)<br>(nonpolar relatively small) | Leu (L)<br>(nonpolar relatively small)<br>Val (V)<br>(nonpolar relatively small)<br>Met (M)<br>(nonpolar relatively small)<br>Ala (A)<br>(neutral and small)<br>Phe (F)<br>(nonpolar and relatively large) | Leu (L)<br>(nonpolar relatively small) |
| Leu (L)<br>(nonpolar and relatively small) | Norl<br>Ile (I)<br>(nonpolar relatively small)<br>Val (V)<br>(nonpolar relatively small)<br>Met (M)<br>(nonpolar relatively small)<br>Ala (A)<br>(neutral and small) | Ile (I)<br>(nonpolar relatively small) |
| Lys (K)<br>(polar and relatively large) | Arg (R)<br>(polar and relatively large)<br>Gln (Q)<br>(polar and relatively small)<br>Asn (N)<br>(polar and relatively small) | Arg (R)<br>(polar and relatively large) |
| Met (M)<br>(nonpolar and relatively small) | Leu (L)<br>(nonpolar and relatively small)<br>Phe (F)<br>(nonpolar and relatively large)<br>Ile (I)<br>(nonpolar relatively small) | Leu (L)<br>(nonpolar and relatively small) |
| Phe (F)<br>(nonpolar and relatively large) | Leu (L)<br>(nonpolar and relatively small)<br>Val (V)<br>(nonpolar relatively small)<br>Ile (I)<br>(nonpolar relatively small)<br>Ala (A)<br>(neutral and small)<br>Tyr (Y)<br>(nonpolar and relatively large) | Tyr (Y)<br>(nonpolar and relatively large) |
| Pro (P)<br>(neutral and small) | Ala (A)<br>(neutral and small) | Ala (A)<br>(neutral and small) |

TABLE 1-continued

| Conservative amino acid substitutions. | | |
|---|---|---|
| Original | Exemplary substitution(s) - conservative | Preferred substitution(s) - conservative |
| Ser (S)<br>(neutral and small) | Thr (T)<br>(neutral and small) | Thr (T)<br>(neutral and small) |
| Thr (T)<br>(neutral and small) | Ser (S)<br>(neutral and small) | Ser (S)<br>(neutral and small) |
| Trp (W)<br>(nonpolar and relatively large) | Tyr (Y)<br>(nonpolar and relatively large)<br>Phe (F)<br>(nonpolar and relatively large) | Tyr (Y)<br>(nonpolar and relatively large) |
| Tyr (Y)<br>(nonpolar and relatively large) | Trp (W)<br>(nonpolar and relatively large)<br>Phe (F)<br>(nonpolar and relatively large)<br>Thr (T)<br>(neutral and small)<br>Ser (S)<br>(neutral and small) | Phe (F)<br>(nonpolar and relatively large) |
| Val (V)<br>(non-polar and small) | Ile (I)<br>(nonpolar relatively small)<br>Leu (L)<br>(nonpolar and relatively small)<br>Met (M)<br>(nonpolar relatively small)<br>Phe (F)<br>(nonpolar and relatively large)<br>Ala (A)<br>(neutral and small) | Leu (L)<br>(nonpolar and relatively small) |

It is also encompassed by the present invention that the one or more polypeptide(s) of or used in the present invention comprise or consist of more than 280, 290, 300, 310, 320, 330 or more than 340 amino acids. It is further envisioned that the polypeptide(s) comprise or consist of 320, 321, 322, 323, 324, 325, 326, 327, 328, 329, 330, 331, 332, 333, 334, 335, 336, 337, 338, 339, 340, 341, 342, 343, 344, 345, 346, 347, 348 or more amino acids. The polypeptide(s) can comprise or consist of 341, 342 or 343 amino acids.

Notably, the polypeptides of any one of SEQ ID NO. 1-28 are highly efficient in converting 3-keto-DON into 3-epi-DON. This can also be seen by the fact that only a small amount of polypeptide is necessary to produce 1 μmol 3-epi-DON per minute (see also FIG. 3). This measurement indicates that the polypeptides described herein have a high activity.

It is thus further envisioned that the polypeptide(s) as described herein is/are capable of converting the substrate 3-keto-DON into the product 3-epi-DON with an activity of at least 0.06 μmol 3-epi-DON per minute per 1 mg of polypeptide.

The "activity" as used herein relates to the "specific activity", namely the product formation rate per enzyme. The specific activity is the amount of product in μmol, which is formed in 1 minute by 1 mg of polypeptide (enzyme) (μmol/min/mg). One way of how the specific activity can be measured is disclosed in the examples.

It is also encompassed that the polypeptide is capable of converting the substrate 3-keto-DON into the product 3-epi-DON with an activity of at least 0.07, 0.08, 0.09, 0.10, 0.15, 0.20, 0.25, 0.30, 0.35, 0.40, 0.45, 0.50, 0.55, 0.60, 0.65, 0.70, 0.75, 0.80, 0.85, 0.90, 1.00, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 2.00 or more μmol 3-epi-DON per minute per 1 mg of polypeptide.

On the other hand, the activity of the polypeptides described herein for converting 3-keto-DON into DON is lower than for the conversion into 3-epi-DON.

It is thus envisioned that the polypeptide as described herein is capable of converting the substrate 3-keto-DON into the product DON with an (specific) activity of at most 0.20, 0.19, 0.18, 0.17, 0.16, 0.15, 0.14, 0.13, 0.12, 0.11, 0.10, 0.09, 0.08, 0.07, 0.06, 0.05, 0.04, 0.03, 0.02, 0.01 or less μmol DON per minute per 1 mg of polypeptide. It is further contemplated that the polypeptide is capable of converting the substrate 3-keto-DON into the product DON with a specific activity of at least 0.015, 0.02, 0.03 or more μmol DON per minute per 1 mg of polypeptide.

It is further possible to calculate the activity ratio of a polypeptide from the activity seen for the formation of 3-epi-DON and for DON. The ratio is calculated by dividing the activity of a given polypeptide for DON by the activity of the very same polypeptide for 3-epi-DON. Preferably, these activities are determined in the very same experiment using 3-keto-DON as substrate. An exemplary method to do so is described in the examples.

It is thus envisioned that the polypeptide as described herein is capable of converting the substrate 3-keto-DON into the product 3-epi-DON and into the product DON with an activity ratio of DON over 3-epi-DON (DON:3-epi-DON) between 0.045 and 0.26. It is also contemplated that the polypeptide is capable of converting the substrate 3-keto-DON into the product 3-epi-DON and into the product DON with an activity ratio of DON to 3-epi-DON (DON:3-epi-DON) between 0.05 and 0.25, 0.05 and 0.23, 0.06 and 0.24, 0.07 and 0.23, 0.08 and 0.22, 0.09 and 0.21, 0.10 and 0.20, 0.11 and 0.19, 0.12 and 0.18, or 0.13 and 0.17.

The activity for DON formation can be measured with the same method as the activity for 3-epi-DON formation. One way to measure whether a certain polypeptide is capable of converting or converts the substrate 3-keto-DON into the products 3-epi-DON and DON with a DON:3-epi-DON ratio between 0.045 and 0.26 is explained in detail in the examples.

For example, the (specific) activity can be calculated by (a) contacting 200 nM of polypeptide with (aa) 3-keto DON at a concentration of 30 ppm;

(ab) buffer comprising of 10.255 mM phosphoric acid, 7.287 mM citric acid, 11.45 mM boric acid and 68.6 mM sodium hydroxide, at a pH of 7.0, wherein the pH is adjusted with HCl; to provide a solution (according to Teorell & Stenhagen, 1938);

(b) taking a 20 μl sample from the solution of step (a); and (ba) contacting the sample with 20 μl of 100% methanol (bb) storing the sample at 4° C. until the end of incubation;

(c) contacting the solution of step (a) with NADPH at a final concentration of 1 mM, to provide for an incubation sample;

(d) incubating the incubation sample at 30° C. for 120 minutes;

(da) taking 20 μl samples after 5 minutes, 10 minutes, 20 minutes, 30 minutes 60 minutes and 120 minutes of the incubation sample; and (db) after taking each sample, contacting each sample with 20 μl of 100% methanol; and (dc) storing each sample at 4° C. until the end of incubation;

(e) contacting the sample taken at 0 minutes in step (b) and the samples taken at 5 minutes, 10 minutes, 20 minutes, 30 minutes 60 minutes and 120 minutes in step (d) with 40% methanol in ultrapure $H_2O$ to provide a concentration of 0.3 ppm 3-keto-DON or less in the sample;

(f) analyzing each sample by LC-MS/MS;

(g) determining the amounts of 3-epi-DON and DON in each sample;

(h) calculating the 3-epi-DON and/or DON formation rate per minute per 1 mg of polypeptide present in the linear phase of the reaction for each sample.

The LC-MS/MS analysis of step may be performed by (fa) separating DON, 3-keto-DON and 3-epi-DON on a 150 mm×2.1 Biphenyl column with a particle size of 2.6 μm;

(fb) wherein the mobile phase consists of a mixture of methanol and water having a maximal conductivity of 0.055 μS/cm with 0.1% (v/v) acetic acid;

(fc) wherein ions are generated by electro spray ionization (ESI) in negative ionization mode, (fd) wherein the LC-MS/MS quantification is performed by a triple quadrupole mass spectrometer.

It is further contemplated that the incubating of step (d) is performed in a thermocycler.

It is also envisioned that the method of the present invention is performed by using a final concentration of 30 ppm 3-keto-DON as substrate. Additionally, or alternatively, the method can be performed by using the polypeptide as disclosed herein in a concentration of 200 nM. Additionally, or alternatively, the method can be performed at a pH of 4.5 to 10.0, preferably at a pH of 5.0 to 7.0, more preferably at a pH of 6.5. Additionally, or alternatively, the method can be performed at a temperature between 14.9° C. to 55.7° C., preferably at a temperature between 25.0° C. and 50.0° C., more preferably at a temperature between 38° C. and 45° C.

Thus, the present invention also relates to a method of converting 3-keto-DON into 3-epi-DON, the method comprising contacting one or more polypeptide(s) comprising or consisting of SEQ ID NO. 1 or a sequence having a sequence identity of at least 72.0% to SEQ ID NO. 1 with 3-keto DON, wherein the method is performed at a pH of 4.5 to 10.0 and/or at a temperature between 14.9° C. to 55.7° C., preferably at a temperature between 25.0° C. and 50.0° C., more preferably at a temperature between 38° C. and 45° C.

It is further envisioned that the polypeptide(s) as disclosed herein is/are capable of converting the substrate 3-keto-DON into the product 3-epi-DON and optionally additionally into the product DON amounting to 100.0% of total product, wherein at least 80.0%, 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0% 97.0% or more of the total product is 3-epi-DON.

As can be seen from the above reaction scheme, 3-keto DON can be converted into two isomers, namely 3-epi-DON and DON. These two isomers thus represent the total product. The total product per definition equals 100%. Since the polypeptides of the present invention are highly stereoselective, one isomer (here 3-epi-DON) is obtained with higher efficiency (or in a higher amount) than the other (here DON). How the amount of DON and/or 3-epi-DON obtained from the substrate 3-keto-DON can be measured is disclosed herein e.g. in the examples. Specifically, of the total product obtained (equaling 100%) at least 80% is 3-epi-DON.

It is further contemplated that the polypeptide as described herein is capable of converting the substrate 3-keto-DON into the product 3-epi-DON and optionally additionally into the product DON amounting to 100.0% of total product, wherein at most 97.0%, 96.0%, 95.0%, 94.0%, 93.0%, 92.0%, 91.0%, 90.0%, 89.0%, 88.0%, 87.0%, 86.0%, 85.0%, 84.0%, 83.0%, 82.0%, 81.0%, 80.0% or less of the total product is 3-epi-DON.

It is further contemplated that the polypeptide as described herein is capable of converting the substrate 3-keto-DON into the product 3-epi-DON and optionally additionally into the product DON amounting to 100.0% of total product, wherein between 79.0% and 96.0%, between 80.0% and 95.0%, between 81.0% and 94.0% of the total product is 3-epi-DON.

Additionally, or alternatively, the polypeptide can be capable of converting the substrate 3-keto-DON into the product 3-epi-DON and additionally into the product DON amounting to 100% of total product, wherein at least 3.0%, 4.5%, 5.0%, 6.0%, 7.0%, 8.0%, 9.0% 10.0% 11.0% 12.0% 13.0% 14.0% 15.0% 16.0% 17.0% 18.0% 19.0% 20.0%, 21.0%, 22.0% or more of the total product is DON.

Likewise, it may be that the polypeptide as disclosed herein is capable of converting the substrate 3-keto-DON into the product 3-epi-DON and additionally into the product DON amounting to 100% of total product, wherein at most 21.5%, 21.0%, 20.0%, 19.0%, 18.0%, 17.0%, 16.0%, 15.0% 14.0% 13.0% 12.0% 11.0% 10.0% 9.0% 8.0% 7.0% 6.0%, 5.0%, 4.0% or less of the total product is DON.

For example, the polypeptide as disclosed herein may be capable of converting the substrate 3-keto-DON into the product 3-epi-DON and additionally into the product DON amounting to 100% of total product, wherein between 3.9% and 21.5%, between 4.0% and 21.0%, or between 5.0% and 19.0% of the total product is DON.

It is further envisioned that the polypeptide(s) as disclosed herein is/are capable of converting the substrate 3-keto-DON into the products 3-epi-DON and DON with a ratio of at least 3.7:1 (3-epi-DON:DON).

For the calculation of this ratio the percentage of the product 3-epi-DON is divided by the percentage of the product DON that is obtained when converting the substrate 3-keto-DON using a specific polypeptide as disclosed herein. It is clear that the ratio is not calculable in the case that no DON and only 3-epi-DON or vice versa is obtained.

This is because mathematically a division trough the number 0 is not possible. Yet, the present invention also relates to polypeptides that are 100% stereo selective for 3-epi-DON. Thus, in case the division is a division through the number 0, such a polypeptide is still embraced by the present invention. Yet, if the division is 0, because only DON is obtained, such polypeptides are not encompassed by the present invention.

It is thus also envisioned that the polypeptide(s) as disclosed herein can be capable of converting the substrate 3-keto-DON into the products 3-epi-DON and DON with a ratio (3-epi-DON:DON) of at least 3.8:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1 or higher. The polypeptide(s) may additionally or alternatively be capable of converting the substrate 3-keto-DON into the products 3-epi-DON and DON with a ratio (3-epi-DON:DON) of at most 25.0:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, or less. Thus, the polypeptide(s) may be capable of converting the substrate 3-keto-DON into the products 3-epi-DON and DON with a ratio of between 24.5:1 to 3.7:1, 24:1 to 4:1, 20:1 to 4:1, 18:1 to 4:1, 19:1 to 5:1, or 18:1 to 6:1.

The present invention also relates to feed or food additives or feed or food comprising one or more polypeptide(s) comprising or consisting of a sequence of SEQ ID NO. 1 or a sequence having a sequence identity of at least 72.0% (e.g., at least 88.5%, 89%, 90%, 91%, 92%, 93%, 94%, 95%, 96%, 97%, 98% or 99%, preferably at least 88.5%) to SEQ ID NO. 1 as disclosed herein.

The feed or food additives or feed or food described herein may be any suitable feed or food additives or feed or food.

The feed or food additives or feed or food described herein but also the pharmaceutical compositions as described herein may comprise a carrier. The carrier can be any suitable carrier. The feed or food additives or feed or food may comprise 1, 2, 3, 4, 5, 6, or more carriers.

The carrier may be a liquid, preferably $H_2O$, or a solid, preferably a nutraceutical and/or a pharmaceutical. For example, the carrier can be a solid or a liquid. Exemplary solids include food/feed supplement(s), dietary supplements, nutraceutical(s) and/or a pharmaceutical(s). Exemplary feed/food supplements inter alia include feed/food additives, vitamins, minerals, amino acids, essential fatty acids, fibre, trace elements, minerals, antioxidants, plant extracts and herbal extracts.

The carrier can also be a carrier for an enzyme. Carriers for enzymes can be both of inorganic and organic origin. Potential inorganic materials used for the immobilization of enzymes are silica (sol-gel silica, fumed silica, colloidal silica nanoparticles and silica gels) and different oxides such as titanium oxide, aluminium oxide and zirconium oxide.

Furthermore, clay materials such as bentonite, halloysite, kaolinite, montmorillonite, sepiolite and calcium apatite are applied. Additionally, carbon-based materials such as activated carbons and charcoal are known as effective enzyme immobilizers. Organic enzyme carriers can be biopolymers but also synthetic polymers. The biopolymers include carbohydrates and proteins. Typical examples are maltodextrin, trehalose, inulin, collagen, cellulose, keratins, carragenaan, chitin, chitosan and alginate. As examples for synthetic polymers polyaniline, polyamides, polystyrene, polyurethane, polypropylene, polyvinyl alcohol and ion exchange resins can be mentioned. An enzyme carrier can also be a carrier as described in Zdarta et al. (2018).

The carrier can also be a liquid. Exemplary liquids include H2O, aqueous solutions, salt solutions (e.g. buffers), gels, viscous preparations, fats or oils. Preferable aqueous solutions containing $H_2O$ and further substances like buffer substances and/or polyalcohols like polyalkylene oxides (PAO), poly-vinyl alcohols (PVA), polyethylene-co-maleic acid anhydrides, polystyrene-co-malic acid anhydrides, dextrans, celluloses, hydrolyzates of chitosan, starches, glycogen, sorbitol, agarose and derivatives thereof, guar gum, pullulan, inulin, xanthan gum, carrageenan, pectin, alginic acid hydrolyzates, bio-polymers, sorbitol, glycerol, cellobiose, and mono propylene glycol (MPG).

The carrier may additionally or alternatively be an eatable component, preferably a non-toxic component and/or a component providing for a texture.

The inventive feed/food additive or feed/food compositions but also the pharmaceutical compositions as described herein can further comprise an enzyme capable of converting or converting DON into 3-keto-DON and/or trichothecenes comprising a 3-R-hydroxy group (such as DON) into trichothecenes comprising a 3-oxo group (such as 3-keto DON) as described herein.

Methods to prepare such feed/food additives or feed/food compositions are known to the skilled person and are inter alia described in WO 99/35240.

The feed/food additive or feed/food compositions or pharmaceutical composition as disclosed herein can be a feed/food additive or feed/food or pharmaceutical composition for reducing the amount of DON. In such cases the feed/food additive or feed/food or pharmaceutical composition further comprises an enzyme capable of converting DON into 3-keto-DON.

The compositions as disclosed herein can also be a composition for reducing the amount of trichothecenes comprising a 3-R-hydroxy group. In such cases these compositions further comprise an enzyme capable of converting trichothecenes comprising a 3-R-hydroxy group into trichothecenes comprising a 3-oxo group.

The compositions (e.g. feed/food additive, feed/food compositions, pharmaceutical composition) described herein can thus further comprise one or more enzyme(s) capable of converting or converting DON into 3-keto-DON and/or trichothecenes comprising a 3-R-hydroxy group into trichothecenes comprising a 3-oxo group. Exemplary enzymes, which can be used in the composition, are inter alia described in WO2016/154640 or WO2019/046954. Thus, the enzymes converting DON into 3-keto DON may comprise or consist of a sequence as disclosed in SEQ ID NO. 1 of WO2016/154640 (SEQ ID NO: 41 herein or SEQ ID NO. 7 of WO2019/046954 (SEQ ID NO. 42 herein). Thus, the composition(s) as described herein (e.g. feed/food additive, feed/food compositions, pharmaceutical composition) may further comprise an enzyme comprising or consisting of SEQ ID NO. 41 and/or 42.

The compositions as disclosed herein (e.g. feed/food additive, feed/food compositions, pharmaceutical composition) can additionally comprise one or more enzymes capable of converting or converting DON into 3-keto-DON and/or trichothecenes comprising a 3-R-hydroxy group into trichothecenes comprising a 3-oxo group as described herein.

The present invention also relates to polypeptide(s) comprising or consisting of a sequence of SEQ ID NO. 1, 2 or 3 or a sequence having a sequence identity of at least 88.5% to SEQ ID NO. 1, 2 or 3, respectively, wherein the polypeptide is capable of converting the substrate 3-keto-DON into the product 3-epi-DON and optionally into the product DON. As also elsewhere disclosed herein it is also envisioned that the one or more polypeptide(s) described herein comprise or consist of a sequence having a sequence identity of at least 89%, at least 90.0%, at least 91.0%, at least 92.0%, at least 93.0%, at least 94.0%, at least 95.0%, at least 96.0%, at least 97.0%, at least 98.0%, at least 99.0% or 100.0% sequence identity to SEQ ID NO. 1.

The present invention also relates to a method of reducing the content of DON in a composition comprising DON or of reducing the toxicity of a composition comprising DON by converting DON into 3-epi-DON, the method comprising a) contacting the composition with an enzyme capable of converting DON into 3-keto DON; and
b) subsequently or concurrently contacting the composition with one or more polypeptide(s) comprising or consisting of SEQ ID NO. 1 or a sequence having a sequence identity of at least 72.0% (e.g., at least 88.5%, 89%, 90%, 91%, 92%, 93%, 94%, 95%, 96%, 97%, 98% or 99%, preferably at least 88.5.0%) to SEQ ID NO. 1.

The present invention also relates to a method of reducing the content of DON in a composition comprising DON or of reducing the toxicity of a composition comprising DON by converting DON into 3-epi-DON, the method comprising a) contacting the composition with an enzyme capable of converting DON into 3-keto DON; and
b) subsequently or concurrently contacting the composition with one or more polypeptide(s) comprising or consisting of SEQ ID NO. 2 or 3 or a sequence having a sequence identity of at least 88.5% to SEQ ID NO. 2 or 3 respectively.

This method may further include the step of contacting the composition with at least one quinone cofactor and/or at least one metal ion and/or at least one redox cofactor. The quinone cofactor may be selected from the group of PQQ (pyrroloquinoline quinone (CAS No. 72909-34-3), tryptophan tryptophylquinone (TTQ, CAS No. 134645-25-3), topaquinone (TPQ, CAS No. 64192-68-3), lysine tyrosylquinone (LTQ, CAS No. 178989-72-5) and cysteine tryptophylquinone (CTQ, CAS No. 400616-72-0). The metal ion, enabling a fast and complete binding of the quinone cofactor to the enzyme capable of converting DON into 3-keto DON, may preferably be the alcohol dehydrogenase SEQ ID NO. 1-3 described in WO2016/154640, can be selected from the group of $Li^+$, $Na^+$, $K^+$, $Mg^{2+}$, $Ca^{2+}$, $Zn^{2+}$, $Zn^{3+}$, $Mn^{2+}$, $Mn^{3+}$, $Fe^{2+}$, $Fe^{3+}$, $Cu^{2+}$, $Cu^{3+}$, $Co^{2+}$ and $Co^3$, preferably $Ca^{2+}$ and $Mg^{2+}$. The at least one redox cofactor can be selected from the group of NAD+, NADP+, the phenazine methosulphate group (PMS, CAS No. 299-11-6), PMS derivatives, potassium hexacyanoferrate (III), sodium hexacyanoferrate (III), cytochrome C, coenzyme Q1, coenzyme Q10, methylene blue and N,N,N',N'-tetramethyl-p-phenylenediamine (TMPD).

Examples of PMS derivatives are: 1-hydroxyphenazine, 2-(pentaprenyl oxy)dihydrophenazine, 5,10-dihydro-9-dimethylallylphenazine-1-carboxylic acid, 5,10-dihydrophenazine-1-carboxylic acid, 5-methylphenazinium methyl sulfate, 6-acetophenazine-1-carboxylic acid, benthophoenin, clofazimine, dihydromethanophenazine, esmeraldic acid, esmeraldin B, izumiphenazine A-C, Janus Green B cation, methanophenazine pelagiomicin A, phenazine, phenazine-1,6-dicarboxylic acid, phenazine-1-carboxamide, phenazine-1-carboxylic acid, phenosafranine, pyocyanin, saphenamycin, or saphenic acid methyl ester.

The present invention also relates to a use of one or more polypeptide(s) as disclosed herein for converting 3-keto-DON into 3-epi-DON and/or into DON.

The present invention also relates to a use of one or more polypeptide(s) as disclosed herein in the manufacture of a feed additive or feed composition or a pharmaceutical composition.

Also, the present invention concerns a use of one or more polypeptide(s) as disclosed herein in the manufacture of biogas, bioethanol, or sugar, preferably from sugar cane or sugar beets. In such uses the compositions or polypeptides of the present invention can be added to compositions comprising trichothecenes such as DON.

The present invention also relates to an additive for use in agrarian compositions comprising 3-keto-DON or DON, the additive comprising one or more polypeptide(s) as disclosed herein.

An "agrarian composition" can be any composition comprising a plant or parts of a plant such as seed or wood. Such agrarian compositions can comprise 3-keto-DON and/or DON. The additive according to the present invention may further comprise one or more enzymes capable of converting or converting DON into 3-keto-DON and/or trichothecenes comprising a 3-R-hydroxy group into trichothecenes comprising a 3-oxo group as described herein. The agrarian composition can also be a composition comprising trichothecenes comprising a R-hydroxy group such as DON.

The present invention also relates to a method of converting a trichothecene comprising a 3-oxo group into a trichothecene comprising a 3-hydroxy group, preferably a 3-S-hydroxy group, the method comprising contacting one or more polypeptide(s) as disclosed herein with trichothecene comprising a 3-oxo group.

Trichothecenes have the following common structure:

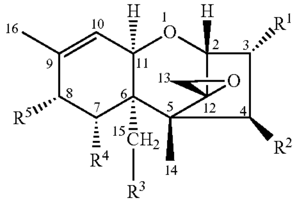

The 3-oxo group of $R^1$ (on C3=3-oxo group) can be converted into a hydroxyl group:

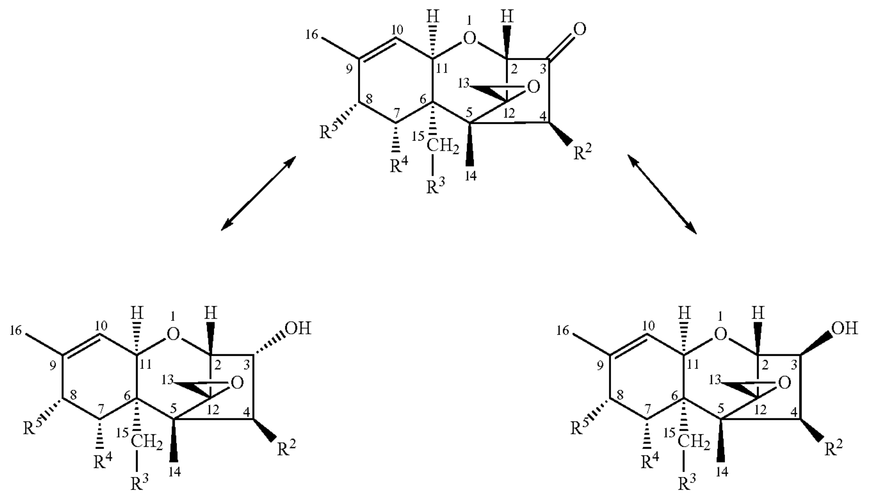

R configuration at carbon 3

S configuration at carbon 3

The skilled person knows which substitutions can be present at $R^1$, $R^2$, $R^3$, $R^4$ and $R^5$. It is known that toxicity of trichothecenes is (at least) partly due to hydroxyl (—OH) group present at the C-3 atom. Thus, in some trichothecenes the C-3 is connected to a hydroxyl group (R1=—OH/-hydroxy group).

Trichothecenes comprising a 3-hydroxy (3-OH) group (at position $R^1$ in the above formula) are known to the skilled person. Non-limiting examples of such trichothecenes include DON (CAS No. 51481-10-8), T-2 Toxin (CAS No. 21259-20-1), HT-2 Toxin (CAS No. 26934-87-2), Nivalenol (CAS No. 23282-20-4), Fuseranon X (CAS No. 23255-69-8), Scirpenetriol (CAS No. 2270-41-9), 15-Acetoxyscirpenol (CAS No. 2623-22-5), 4,15-Diacetoxyscirpenol (CAS No. 2270-40-8), Deacetylneosolaniol (CAS No. 74833-39-9), Neosolaniol (CAS No. 36519-25-2), Sporotrichiol (CAS No. 101401-89-2) and Sambucinol (CAS No. 90044-33-0). These trichothecenes comprising a 3-hydroxy (3-OH) group can be oxidized into trichothecenes comprising a 3-oxo (=O; at position $R^1$). Enzymes capable of such conversion are described herein. The polypeptides can then convert these trichothecenes comprising a 3-oxo group into preferably one of the two isomers of trichothecenes comprising a 3-hydroxy (3-OH) group, namely the R and the S configuration.

It is encompassed by the present invention that the trichothecene comprising a 3-hydroxy group is present in the S configuration.

The present invention also relates to a host cell comprising one or more polypeptide(s) as disclosed herein.

The term "host cell" refers to all cells containing either a nucleotide sequence to be expressed, or an expression vector, and which is able to produce an enzyme or a polypeptide according to the invention. In particular, this refers to prokaryotic and/or eukaryotic cells, preferably *Pichia pastoris, Escherichia coli, Bacillus subtilis, Streptomyces, Hansenula, Trichoderma, Lactobacillus, Aspergillus*, plant cells and/or spores of *Bacillus, Trichoderma* or *Aspergillus*. The name *P. pastoris* used herein is synonymous with the name *Komagataella pastoris, P. pastoris* being the older and *K. pastoris* the systematically newer name (Yamada et al. (1995)). Notably, species of *K. pastoris* have been recently reassigned to be *K. phaffii* (Kurtzman (2009)). *K. phaffii* as used herein can e.g. relate to strains *K. phaffii* CBS 7435, *K. phaffii* GS115 or *K. phaffii* JC308.

It is further encompassed that the host cell can further express a cofactor for the polypeptide(s) described herein. The co-factor may be any suitable co-factor. For example, the co-factor is NAD/H or NADP/H. It is also envisioned that the host cell is a recombinant cell.

The present invention also relates to a plant genetically modified to express one or more polypeptide(s) as disclosed herein. Exemplary plants include inter alia corn (maize), wheat, barley, rye and oat.

The present invention also relates to a seed of a plant as described herein.

The present invention also relates to a preparation comprising one or more polypeptide(s) as disclosed herein.

A "preparation" in accordance with the present invention is obtainable by using the polypeptide(s) described herein in a composition as described herein. In one embodiment, the preparation can therefore comprise the polypeptides or parts of the polypeptide(s) described herein as well as further components such as the carrier, agrarian extracts etc. The preparation can also comprise further molecules and/or proteins and/or substances e.g. a left over from a buffer used in the method of the present invention due to e.g. less efficient purification of the polypeptide(s) described herein.

The present invention also relates to one or more polypeptide(s) as disclosed herein for use in the prevention and/or treatment of mycotoxicosis. This use may comprise the step of administering to a subject at risk or in need thereof one or more polypeptide(s) as disclosed herein.

Similarly, the present invention also relates to a method of prevention or treatment of mycotoxicosis, the method comprising administering to a subject at risk or in need thereof one or more polypeptide(s) as disclosed herein.

Preferably, a therapeutically effective amount of the one or more polypeptide(s) as described herein are administered. The subject can be afflicted with mycotoxicosis. The subject can also be a subject at risk of developing mycotoxicosis.

The present invention also relates to a pharmaceutical composition comprising one or more polypeptides as disclosed herein. The pharmaceutical composition may further comprise a pharmaceutically acceptable carrier. Such carrier may be any carrier as disclosed herein.

The present invention also relates to polynucleotide(s) comprising or consisting of a sequence encoding for SEQ ID NO. 1 or a sequence having a sequence identity of at least 72.0% or 88.5% to SEQ ID NO. 1, wherein the polynucleotide is capable of converting the substrate 3-keto-DON into the product 3-epi-DON and optionally into the product DON.

The present invention also relates to polynucleotide(s) comprising or consisting of a sequence encoding for SEQ ID NO. 2 or 3 or a sequence having a sequence identity of at least 88.5% to SEQ ID NO. 2 or 3, respectively, wherein the polynucleotide is capable of converting the substrate 3-keto-DON into the product 3-epi-DON and optionally into the product DON.

The nucleic acid may be introduced or inserted into an expression vector. The term "expression vector" refers to a nucleic acid molecule construct that is able to express a gene in vivo or in vitro. In particular, it can encompass DNA constructs suitable for transferring the polypeptide-encoding nucleotide sequence into the host cell so as to be integrated in the genome or freely located in the extrachromosomal space, and to intracellularly express the polypeptide-encoding nucleotide sequence and, optionally, transport the polypeptide out of the cell.

It is noted that as used herein, the singular forms "a", "an", and "the", include plural references unless the context clearly indicates otherwise. Thus, for example, reference to "a polypeptide" includes one or more of such different polypeptides and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "less than" or in turn "more than" does not include the concrete number.

For example, less than 20 means less than the number indicated. Similarly, more than or greater than means more than or greater than the indicated number, e.g. more than 80% means more than or greater than the indicated number of 80%.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having". When used herein "consisting of" excludes any element, step, or ingredient not specified.

The term "including" means "including but not limited to". "Including" and "including but not limited to" are used interchangeably.

When used herein, the term "about" is understood to mean that there can be variation in the respective value or range (such as pH, concentration, percentage, molarity, number of amino acids, time etc.) that can be up to 5%, up to 10% of the given value. For example, if a formulation comprises about 5 mg/ml of a compound, this is understood to mean that a formulation can have between 4.5 and 5.5 mg/ml.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications cited throughout the text of this specification (including all patents, patent application, scientific publications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

The content of all documents and patent documents cited herein is incorporated by reference in their entirety.

A better understanding of the present invention and of its advantages will be had from the following examples, offered for illustrative purposes only. The examples are not intended to limit the scope of the present invention in any way.

The present invention is further characterized by the following items.

1. Method of converting 3-keto-DON into 3-epi-DON, the method comprising contacting one or more polypeptide (s) comprising or consisting of SEQ ID NO. 1 or a sequence having a sequence identity of at least 72.0% (e.g., at least 88.5%, 89%, 90%, 91%, 92%, 93%, 94%, 95%, 96%, 97%, 98% or 99%, preferably at least 88.5%) to SEQ ID NO. 1 with 3-keto DON.
2. Method of converting 3-keto-DON into 3-epi-DON, the method comprising contacting one or more polypeptide (s) comprising or consisting of SEQ ID NO. 2 or a sequence having a sequence identity of at least 88.5% to SEQ ID NO. 2 with 3-keto DON.
3. Method of converting 3-keto-DON into 3-epi-DON, the method comprising contacting one or more polypeptide (s) comprising or consisting of SEQ ID NO. 3 or a sequence having a sequence identity of at least 88.5% to SEQ ID NO. 3 with 3-keto DON.
4. Method of any one of the preceding items, wherein the polypeptide is a reductase.
5. Method of any one of the preceding items, wherein the polypeptide comprises one or more of the following polypeptide sequences:

(i)
YRKLGNSG;

(ii)
LGTMTFG;

(iii)
AGGNF$X_1$DTA$X_2$VYS, wherein $X_1$ is I or L and $X_2$ is N or D;

(iv)
ETLRFLDD;

(v)
GKI$X_3$YYGFSN, wherein $X_3$ is A or G;

(vi)
RDIEHE$X_4$VPA, wherein $X_4$ = I or V;

-continued (vii)
GLLPWSPLGGGWL;

(viii)
GATRLGENP;

(ix)
AQVALAW;
and/or (x)
PAV$X_5$SVILGART, wherein $X_5$ = T or A.

6. Method of any one of the preceding items, wherein the polypeptide comprises 1, 2, 3, 4, 5, 6, 7, 8, 9 or 10 of the peptide sequences shown in (i)-(x).
7. Method of any one of the preceding items, wherein the polypeptide has a sequence identity of at least 75.0%, at least 80.0%, at least 83.0%, at least 85.0%, at least 87.0%, at least 88.5%, at least 89%, at least 90.0%, at least 91.0%, at least 92.0%, at least 93.0%, at least 94.0%, at least 95.0%, at least 96.0%, at least 97.0%, at least 98.0%, at least 99.0% or more sequence identity to SEQ ID NO. 1.
8. Method of any one of the preceding items, wherein the polypeptide has a sequence identity of at least at least 89.0%, at least 90.0%, at least 91.0%, at least 92.0%, at least 93.0%, at least 94.0%, at least 95.0%, at least 96.0%, at least 97.0%, at least 98.0%, at least 99.0% or more sequence identity to SEQ ID NO. 1.
9. Method of any one of the preceding items, wherein the one or more polypeptide(s) comprising a sequence having a sequence identity of at least 72.0% to SEQ ID NO. 1 comprises one or more amino acid substitutions compared to a sequence of SEQ ID NO. 1.
10. Method of any one of the preceding items, wherein the one or more polypeptide(s) comprising a sequence having a sequence identity of at least 88.5% to SEQ ID NO. 2 comprises one or more amino acid substitutions compared to a sequence of SEQ ID NO. 2.
11. Method of any one of the preceding items, wherein the one or more polypeptide(s) comprising a sequence having a sequence identity of at least 88.5% to SEQ ID NO. 3 comprises one or more amino acid substitutions compared to a sequence of SEQ ID NO. 3.
12. Method of any one of the preceding items, wherein the one or more amino acid substitutions comprise or consist of conservative amino acid substitutions.
13. Method of any one of the preceding items, wherein the polypeptide comprises or consists of 341, 342 or 343 amino acids.
14. Method of any one of the preceding items, wherein the polypeptide(s) further has a sequence identity of at least 95.0%, 96.0%, 97.0%, 98.0%, 99.0% or more to any one of SEQ ID NO. 2-28.
15. Method of any one of the preceding items, wherein the polypeptide(s) further has a sequence identity of at least 95.0%, 96.0%, 97.0%, 98.0%, 99.0% or more to any one of SEQ ID NO. 2-7.
16. Method of any one of the preceding items, wherein the polypeptide(s) further has a sequence identity of at least 95.0%, 96.0%, 97.0%, 98.0%, 99.0% or more to any one of SEQ ID NO. 2 or 3.
17. Method of any one of the preceding items, wherein the polypeptide(s) comprises or consist of a sequence of any one of SEQ ID NO. 1-28.
18. Method of any one of the preceding items, wherein the polypeptide is capable of converting the substrate 3-keto-DON into the product 3-epi-DON and into the product DON with an activity ratio of DON to 3-epi-DON (DON:3-epi-DON) between 0.045 and 0.26.
19. Method of any one of the preceding items, wherein the polypeptide is capable of converting the substrate 3-keto-DON into the product 3-epi-DON and into the product DON with an activity ratio of DON to 3-epi-DON (DON:3-epi-DON) between 0.05 and 0.25, 0.05 and 0.23, 0.06 and 0.24, 0.07 and 0.23, 0.08 and 0.22, 0.09 and 0.21, 0.10 and 0.20, 0.11 and 0.19, 0.12 and 0.18, 0.13 and 0.17.
20. Method of any one of the preceding items, wherein the specific activity for DON is measured with the same method as the activity for 3-epi-DON.
21. Method of any one of the preceding items, wherein the polypeptide is capable of converting the substrate 3-keto-DON into the product 3-epi-DON with an activity of at least 0.06 μmol 3-epi-DON per minute per 1 mg of polypeptide.
22. Method of any one of the preceding items, wherein the polypeptide is capable of converting the substrate 3-keto-DON into the product 3-epi-DON with an activity of at least 0.07, 0.08, 0.09, 0.10, 0.15, 0.20, 0.25, 0.30, 0.35, 0.40, 0.45, 0.50, 0.55, 0.60, 0.65, 0.70, 0.75, 0.80, 0.85, 0.90, 1.00, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 2.00 or more μmol 3-epi-DON per minute per 1 mg of polypeptide.
23. Method of any one of the preceding items, wherein the polypeptide is capable of converting the substrate 3-keto-DON into the product DON with an activity of at most 0.20, 0.19, 0.18, 0.17, 0.16, 0.15, 0.14, 0.13, 0.12, 0.11, 0.10, 0.09, 0.08, 0.07, 0.06, 0.05, 0.04, 0.03, 0.02, 0.01 or less μmol DON per minute per 1 mg of polypeptide.
24. Method of any one of the preceding items, wherein the polypeptide is capable of converting the substrate 3-keto-DON into the product DON with an activity of at least 0.015, 0.02, 0.03 or more μmol DON per minute per 1 mg of polypeptide.
25. Method of any one of the preceding items, wherein the (specific) activity is calculated by (a) contacting 200 nM of polypeptide with
(aa) 3-keto DON at a concentration of 30 ppm;
(ab) buffer comprising of 10.255 mM phosphoric acid, 7.287 mM citric acid, 11.45 mM boric acid and 68.6 mM sodium hydroxide, at a pH of 7.0, wherein the pH is adjusted with HCl;

to provide a solution (b) taking a 20 μl sample from the solution of step (a); and
(ba) contacting the sample with 20 μl of 100% methanol
(bb) storing the sample at 4° C. until the end of incubation;
(c) contacting the solution of step (a) with NADPH at a final concentration of 1 mM, to provide for an incubation sample;
(d) incubating the incubation sample at 30° C. for 120 minutes;
(da) taking 20 μl samples after 5 minutes, 10 minutes, 20 minutes, 30 minutes 60 minutes and 120 minutes of the incubation sample; and
(db) after taking each sample, contacting each sample with 20 μl of 100% methanol; and
(dc) storing each sample at 4° C. until the end of incubation;

(e) contacting the sample taken at 0 minutes in step (b) and the samples taken at 5 minutes, 10 minutes, 20 minutes, 30 minutes 60 minutes and 120 minutes in step (d) with 40% methanol in ultrapure $H_2O$ to provide a concentration of 0.3 ppm 3-keto-DON or less in the sample;

(f) analyzing each sample by LC-MS/MS;

(g) determining the amounts of 3-epi-DON and DON in each sample;

(h) calculating the 3-epi-DON and/or DON formation rate per minute per 1 mg of polypeptide present in the linear phase of the reaction for each sample.

26. Method of any one of the preceding items, wherein the LC-MS/MS analysis of step (f) is performed by (fa) separating DON, 3-keto-DON and 3-epi-DON on a 150 mm×2.1 Biphenyl column with a particle size of 2.6 μm;

(fb) wherein the mobile phase consists of a mixture of methanol and water having a maximal conductivity of 0.055 μS/cm with 0.1% (v/v) acetic acid;

(fc) wherein ions are generated by electro spray ionization (ESI) in negative ionization mode, (fd) wherein the LC-MS/MS quantification is performed by a triple quadrupole mass spectrometer.

27. Method of any one of the preceding items, wherein the incubating of step (d) is performed in a thermocycler.

28. Method of any one of the preceding items, wherein the method is performed by using a final concentration of 30 ppm 3-keto-DON as substrate.

29. Method of any one of the preceding items, wherein the method is performed by using the polypeptide of any one of the preceding claims in a concentration of 200 nM.

30. Method of any one of the preceding items, wherein the method is performed at a pH of 4.5 to 10.0, preferably at a pH of 5.0 to 7.0, more preferably at a pH of 6.5.

31. Method of any one of the preceding items, wherein the method is performed at a temperature between 14.9° C. to 55.7° C., preferably at a temperature between 25.0° C. and 50.0° C., more preferably at a temperature between 38° C. and 45° C.

32. Method of any one of the preceding items, wherein the polypeptide is capable of converting the substrate 3-keto-DON into the product 3-epi-DON and optionally additionally into the product DON amounting to 100.0% of total product, wherein at least 80.0%, 81.0%, 82.0%, 83.0%, 84.0%, 85.0%, 86.0%, 87.0% 88.0%, 89.0%, 90.0%, 91.0%, 92.0%, 93.0%, 94.0%, 95.0%, 96.0% 97.0% or more of the total product is 3-epi-DON.

33. Method of any one of the preceding items, wherein the polypeptide is capable of converting the substrate 3-keto-DON into the product 3-epi-DON and optionally additionally into the product DON amounting to 100.0% of total product, wherein at most 97.0%, 96.0%, 95.0%, 94.0%, 93.0%, 92.0%, 91.0%, 90.0%, 89.0%, 88.0%, 87.0%, 86.0%, 85.0%, 84.0%, 83.0%, 82.0%, 81.0%, 80.0% or less of the total product is 3-epi-DON.

34. Method of any one of the preceding items, wherein the polypeptide is capable of converting the substrate 3-keto-DON into the product 3-epi-DON and optionally additionally into the product DON amounting to 100.0% of total product, wherein between 79.0% and 96.0%, between 80.0% and 95.0%, between 81.0% and 94.0% of the total product is 3-epi-DON.

35. Method of any one of the preceding items, wherein the polypeptide is capable of converting the substrate 3-keto-DON into the product 3-epi-DON and additionally into the product DON amounting to 100% of total product, wherein at least 4.5%, 5.0%, 6.0%, 7.0% 8.0% 9.0% 10.0% 11.0% 12.0% 13.0% 14.0% 15.0% 16.0% 17.0% 18.0%, 19.0%, 20.0%, 21.0%, 22.0% or more of the total product is DON.

36. Method of any one of the preceding items, wherein the polypeptide is capable of converting the substrate 3-keto-DON into the product 3-epi-DON and additionally into the product DON amounting to 100% of total product, wherein at most 21.5%, 21.0%, 20.0% 19.0% 18.0% 17.0% 16.0% 15.0% 14.0% 13.0% 12.0% 11.0% 10.0% 9.0%, 8.0%, 7.0%, 6.0%, 5.0%, 4.0% or less of the total product is DON.

37. Method of any one of the preceding items, wherein the polypeptide is capable of converting the substrate 3-keto-DON into the product 3-epi-DON and additionally into the product DON amounting to 100% of total product, wherein between 3.9% and 21.5%, between 4.0% and 21.0%, or between 5.0% and 19.0% of the total product is DON.

38. Method of any one of the preceding items, wherein the polypeptide is capable of converting the substrate 3-keto-DON into the products 3-epi-DON and DON with a ratio of at least 3.7:1 (3-epi-DON:DON).

39. Method of any one of the preceding items, wherein the polypeptide is capable of converting the substrate 3-keto-DON into the products 3-epi-DON and DON with a ratio of at least 3.8:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1 or higher.

40. Method of any one of the preceding items, wherein the polypeptide is capable of converting the substrate 3-keto-DON into the products 3-epi-DON and DON with a ratio of at most 25.0:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, or less.

41. Method of any one of the preceding items, wherein the polypeptide is capable of converting the substrate 3-keto-DON into the products 3-epi-DON and DON with a ratio of between 24.5:1 to 3.7:1, 24:1 to 4:1, 20:1 to 4:1, 18:1 to 4:1, 19:1 to 5:1, or 18:1 to 6:1.

42. Feed or food additives or feed or food comprising one or more polypeptide(s) comprising or consisting of a sequence of SEQ ID NO. 1 or a sequence having a sequence identity of at least 72.0% (e.g., at least 88.5%, 89%, 90%, 91%, 92%, 93%, 94%, 95%, 96%, 97%, 98% or 99%, preferably at least 88.5%) to SEQ ID NO. 1.

43. Feed or food additives or feed or food comprising one or more polypeptide(s) comprising or consisting of a sequence of SEQ ID NO. 2 or a sequence having a sequence identity of at least 88.5% to SEQ ID NO. 2.

44. Feed or food additives or feed or food comprising one or more polypeptide(s) comprising or consisting of a sequence of SEQ ID NO. 3 or a sequence having a sequence identity of at least 88.5% to SEQ ID NO. 3.

45. The feed or food additives or feed or food according to any one of the preceding items, wherein the food or feed additive further comprises a carrier.

46. The feed or food additives or feed or food according to any one of the preceding items, wherein the carrier is a liquid, preferably $H_2O$, or a solid, preferably a nutraceutical and/or a pharmaceutical.

47. The feed or food additives or feed or food according to any one of the preceding items, wherein the carrier is an eatable component, preferably a non-toxic component and/or a component providing for a texture.
48. Polypeptide(s) comprising or consisting of a sequence of SEQ ID NO. 1 or a sequence having a sequence identity of at least 88.5% to SEQ ID NO. 1, wherein the polypeptide is capable of converting the substrate 3-keto-DON into the product 3-epi-DON and optionally into the product DON.
49. Polypeptide(s) comprising or consisting of a sequence of SEQ ID NO. 2 or a sequence having a sequence identity of at least 88.5% to SEQ ID NO. 2, wherein the polypeptide is capable of converting the substrate 3-keto-DON into the product 3-epi-DON and optionally into the product DON.
50. Polypeptide(s) comprising or consisting of a sequence of SEQ ID NO. 3 or a sequence having a sequence identity of at least 88.5% to SEQ ID NO. 3, wherein the polypeptide is capable of converting the substrate 3-keto-DON into the product 3-epi-DON and optionally into the product DON.
51. Method of reducing the content of DON in a composition comprising DON or of reducing the toxicity of a composition comprising DON by converting DON into 3-epi-DON, the method comprising
a) contacting the composition with an enzyme capable of converting DON into 3-keto DON; and
b) subsequently or concurrently contacting the composition with one or more polypeptide(s) comprising or consisting of SEQ ID NO. 1 or a sequence having a sequence identity of at least 72.0% (e.g., at least 88.5%, 89%, 90%, 91%, 92%, 93%, 94%, 95%, 96%, 97%, 98% or 99%, preferably at least 88.5%) to SEQ ID NO. 1.
52. Method of reducing the content of DON in a composition comprising DON or of reducing the toxicity of a composition comprising DON by converting DON into 3-epi-DON, the method comprising
a) contacting the composition with an enzyme capable of converting DON into 3-keto DON; and
b) subsequently or concurrently contacting the composition with one or more polypeptide(s) comprising or consisting of SEQ ID NO. 2 or a sequence having a sequence identity of at least 88.5% to SEQ ID NO. 2.
53. Method of reducing the content of DON in a composition comprising DON or of reducing the toxicity of a composition comprising DON by converting DON into 3-epi-DON, the method comprising
a) contacting the composition with an enzyme capable of converting DON into 3-keto DON; and
b) subsequently or concurrently contacting the composition with one or more polypeptide(s) comprising or consisting of SEQ ID NO. 3 or a sequence having a sequence identity of at least 88.5% to SEQ ID NO. 3.
54. Use of one or more polypeptide(s) as defined in any one of the preceding items (e.g., comprising or consisting of SEQ ID NO. 1 or a sequence having a sequence identity of at least 88.5% to SEQ ID NO. 1) for converting 3-keto-DON into 3-epi-DON and/or into DON.
55. Use of one or more polypeptide(s) as defined in any one of the preceding items (e.g., comprising or consisting of SEQ ID NO. 1 or a sequence having a sequence identity of at least 88.5% to SEQ ID NO. 1) in the manufacture of a feed additive or feed composition or a pharmaceutical composition.
56. Use of one or more polypeptide(s) as defined in any one of the preceding items (e.g., comprising or consisting of SEQ ID NO. 1 or a sequence having a sequence identity of at least 88.5% to SEQ ID NO. 1) in the manufacture of biogas, bioethanol, or sugar, preferably from sugar cane or sugar beets.
57. Additive for use in agrarian compositions comprising 3-keto-DON or DON, the additive comprising one or more polypeptide(s) as defined in any one of the preceding items (e.g., comprising or consisting of SEQ ID NO. 1 or a sequence having a sequence identity of at least 88.5% to SEQ ID NO. 1).
58. Method of converting a trichothecene comprising a 3-oxo group into a trichothecene comprising a 3-hydroxy group, the method comprising contacting one or more polypeptide(s) as defined in any one of the preceding items (e.g., comprising or consisting of SEQ ID NO. 1 or a sequence having a sequence identity of at least 88.5% to SEQ ID NO. 1) with trichothecene comprising a 3-oxo group.
59. The method of item 58, wherein the trichothecene comprising a 3-hydroxy group is present in the S configuration.
60. Host cell comprising one or more polypeptide(s) as defined in any one of the preceding items (e.g., comprising or consisting of SEQ ID NO. 1 or a sequence having a sequence identity of at least 88.5% to SEQ ID NO. 1).
61. The host cell of item 60, wherein the host cell is a recombinant cell.
62. The host cell of item 60 or 61 additionally expressing a cofactor for the polypeptide, preferably overexpressing NADH or NADPH.
63. Plant genetically modified to express one or more polypeptide(s) as defined in any one of the preceding items (e.g., comprising or consisting of SEQ ID NO. 1 or a sequence having a sequence identity of at least 88.5% to SEQ ID NO. 1).
64. Seed of a plant defined in item 63.
65. Preparation comprising one or more polypeptide(s) as defined in any one of the preceding items (e.g., comprising or consisting of SEQ ID NO. 1 or a sequence having a sequence identity of at least 88.5% to SEQ ID NO. 1).
66. One or more polypeptide(s) as defined in any one of the preceding items (e.g., comprising or consisting of SEQ ID NO. 1 or a sequence having a sequence identity of at least 88.5% to SEQ ID NO. 1) for use in the prevention and/or treatment of mycotoxicosis.
67. Method of prevention or treatment of mycotoxicosis, the method comprising administering to a subject at risk or in need thereof one or more polypeptide(s) as defined in any one of the preceding items (e.g., comprising or consisting of SEQ ID NO. 1 or a sequence having a sequence identity of at least 88.5% to SEQ ID NO. 1).
68. Method of item 67 or polypeptide for use of item 66, wherein the polypeptide is administered in a therapeutically efficient amount.
69. Pharmaceutical composition comprising one or more polypeptides as defined in any one of the preceding items (e.g., comprising or consisting of SEQ ID NO. 1 or a sequence having a sequence identity of at least 88.5% to SEQ ID NO. 1).
70. Pharmaceutical composition of item 58 further comprising a pharmaceutically acceptable carrier.

71. Polynucleotide(s) comprising or consisting of a sequence encoding for SEQ ID NO. 1 or a sequence having a sequence identity of at least 88.5% to SEQ ID NO. 1, wherein the polynucleotide is capable of converting the substrate 3-keto-DON into the product 3-epi-DON and optionally into the product DON.
72. Polynucleotide(s) comprising or consisting of a sequence encoding for SEQ ID NO. 2 or a sequence having a sequence identity of at least 88.5% to SEQ ID NO. 2, wherein the polynucleotide is capable of converting the substrate 3-keto-DON into the product 3-epi-DON and optionally into the product DON.
73. Polynucleotide(s) comprising or consisting of a sequence encoding for SEQ ID NO. 3 or a sequence having a sequence identity of at least 88.5% to SEQ ID NO. 3, wherein the polynucleotide is capable of converting the substrate 3-keto-DON into the product 3-epi-DON and optionally into the product DON.
74. Method of any one of the preceding items, wherein the amount of epi-DON and/or DON obtained from the substrate 3-keto DON is calculated by
(a) contacting 200 nM of polypeptide with
(aa) 3-keto DON at a concentration of 30 ppm;
(ab) buffer comprising of 10.255 mM phosphoric acid, 7.287 mM citric acid, 11.45 mM boric acid and 68.6 mM sodium hydroxide, at a pH of 7.0, wherein the pH is adjusted with HCl; to provide a solution
(b) taking a 20 μl sample from the solution of step (a); and
(ba) contacting the sample with 20 μl of 100% methanol
(bb) storing the sample at 4° C. until the end of incubation;
(c) contacting the solution of step (a) with NADPH at a final concentration of 1 mM, to provide for an incubation sample;
(d) incubating the incubation sample at 30° C. for 120 minutes, taking a 20 μl sample and contacting the sample with 20 μl of 100% methanol;
(e) contacting the sample taken at 0 minutes in step (b) and the sample taken at 120 minutes in step (d) with 40% methanol in ultrapure $H_2O$ to provide a concentration of 0.3 ppm 3-keto-DON or less in the sample;
(f) analyzing each sample by LC-MS/MS;
(g) determining the amounts of 3-epi-DON and DON in each sample;
(h) calculating the amount of total product of 3-epi-DON and DON the sum of which is set at 100%
(i) calculating the percentage of 3-epi-DON and/or the percentage of DON with regard to the total product obtained (=100%).
75. Method of any one of the preceding items, wherein the LC-MS/MS analysis of step (f) is performed by
(fa) separating DON, 3-keto-DON and 3-epi-DON on a 150 mm×2.1 Biphenyl column with a particle size of 2.6 μm;
(fb) wherein the mobile phase consists of a mixture of methanol and water having a maximal conductivity of 0.055 μS/cm with 0.1% (v/v) acetic acid;
(fc) wherein ions are generated by electro spray ionization (ESI) in negative ionization mode,
(fd) wherein the LC-MS/MS quantification is performed by a triple quadrupole mass spectrometer.
76. Method of any one of the preceding items, wherein said one or more polypeptide(s) comprising or consisting of SEQ ID NO. 1 or a sequence having a sequence identity of at least 88.5% (e.g., at least 89% or at least 90%) to SEQ ID NO. 1 with 3-keto DON.
77. Method of any one of the preceding items, wherein said method is an in vitro, in vivo or ex vivo method.
78. Method of any one of the preceding items, wherein said method is a manufacturing method, preferably feed additive manufacturing method or feed composition manufacturing method or a pharmaceutical composition manufacturing method.
79. Use of any one of the preceding items, wherein said use is a use in a manufacturing process, preferably in a feed additive manufacturing process or in a feed composition manufacturing process or in a pharmaceutical composition manufacturing process.
80. Use of any one of the preceding items, wherein said use an in vitro, in vivo or ex vivo use.

The following sequences are used in the present application.

TABLE 2

Depicting sequences as described herein.

| # | Synonym | Sequence |
|---|---|---|
| 1 | SEQ ID NO. 1 | MDYRKLGNSGAVVSHLCLGTMTFGKEADEATSHLLLDDYVAAGGNFIDTADVYSTGVSETII<br>GNWLKAKPGRELNLVIASKGRFPMGNGPNDLGLSRKHLGAALDASLKRLGVERIDLYQMH<br>AFDALTPMDETLRFLDDSIRNGKIAYYGFSNFTGWQLTKAVYLAKLNGYQPPVTLQPQYNLL<br>VRDIEHEIVPASLDAQIGLLPWSPLGGGWLSGKYKRDQAPSGATRLGENPKRGMEAFEAR<br>NAKDATWSIIGAVEDIAKAHNVSMAQVALAWVVAQPAVTSVILGARTREQLADNLKSVSLKL<br>SAADLATLSEASKPAMSDYPYGAGGINQRHRKLEGGR<br>Total amino acids: 343 |
| 2 | SEQ ID NO. 2 | MEYRKLGNSGTIVTSYCLGTMTFGAEADETTSHLILDDYVEAGGNFIDTANVYSLGVSEEIV<br>GRWLKARPEAASQVVLATKGRFPMGAGPNDIGLSRKHLNRALEDSLRRLGVEQIDLYQMH<br>AWDALTPIEETLRFLDDAVGAGKIAYYGFSNYLGWQVTKAVHVAKANHWSAPVTLQPQYN<br>LLVRDIEHEIVPACLDAGMGLLPWSPLGGGWLAGKYQRDVMPSGATRLGENPNRGMESF<br>GPRNAQERTWQIIDAVAEIAKDRGASAAQVALAWVEARPAVTSVILGARTREQLADNLGSS<br>KVKLSAEETDKLTRISMPQMSDYPYGERGVSQRFRKMEGGR<br>Total amino acids: 343 |
| 3 | SEQ ID NO. 3 | MDYRKLGNSGAWSNLCLGTMTFGDEADEATSFVLMDQYVEAGGNFLDTADVYSAGLSEE<br>IVGRWLKGKKLRDLVIATKGRFPMGQGPNHLGLSRKHLGEALDASLQRLGVEQIDLYQMHA<br>WDALTPLEETLRFLDDAVRSGKIAYYGFSNFLGWHITKAVWMARAQGYAAPVTLQPQYNLL<br>VRDIEHEWPACEDAGMGLLPWSPLGGGWLSGKYKRDQMPEGATRLGENPKRGMEAYE<br>GRNAQERTWAIIGAVEDIAKAQDVTMAQVALAWTAARPAVTSVILGARTAEQLKDNLGAAD<br>LVLSEADMERLNAVSAPQMADYPYGTGGIGQRNRKIEGGR<br>Total amino acids: 341 |

TABLE 2-continued

Depicting sequences as described herein.

| # | Synonym | Sequence |
|---|---|---|
| 4 | SEQ ID NO. 4 | MDYRKLGNSGAVVSHLCLGTMTFGSEADEATSFKLLDDYVAAGGNFIDTADVYSAGVSEEII<br>GRWLKDKPGRAQNLVIATKGRFPMGQGPNDLGLSRKHLGAALDASLKRLGVEQIDLYQMH<br>AFDVLTPLEETLRFLDDSIRNGKIAYYGFSNFTGWQLTKAVWLAKLNGYQPPVTLQPQYSLL<br>VRDIEHEIVPASLDAGIGLLPWSPLGGGWLSGKYKRDQMPTGATRLGENPKRGMEAFEAR<br>NAKDSTWAVIGAVEDIAKARGVSMAQVALAWVAAQPAVASVILGARTQEQLADNLKSAALK<br>LSAGDLQTLGDVSKPVMADYPYGTGGINQRNRNIEGGR<br>Total amino acids: 343 |
| 5 | SEQ ID NO. 5 | MKYRKLGNSGAVVSAYCLGTMTFGAESDEATSFRLMDDYVAAGGNFLDTANVYSAGVSE<br>EIVGRWLKTKPTGLRDLVITTKGRFPMGDGPNHLGLSRKNLREALDASLKRLGVEHIDLYQ<br>MHAFDALTPLEETLRFLDDSIRNGKIAYYGFSNFLGWQLTKAVWIARANGYQPPVTLQPQY<br>NLLVRDIEHEIVPASLDAGIGLLPWSPLGGGWLSGKYRRDEMPTGATRLGENPKRGGEAYE<br>RRNAKSATWDIIGWEDVAKTRGVSMAQVALAWVAQRPAVTSVILGARTTEQLKDNLGAID<br>LALSTEEIEKLNAASKPAVGDYPYGAGGINQRNRKIEGGR<br>Total amino acids: 343 |
| 6 | SEQ ID NO. 6 | MQYRKLGNSGAWVSTQTLGTMTFGAEADEATSFQLMDDYVAAGGNFLDTADVYSAGTSE<br>EIVGRWLKARPEAARQVLITTKARFPMGSGPNDLGLSRRHLNQALDASLGRLGVEHIDLYQ<br>MHAFDALTPLEETLRFLDDAIRNGKIGYYGFSNFIGWQLTKATWIAKAGGLAPPITLQPHYNL<br>LVRDIEHEIVPAALDADIGLLPWSPLGGGWLTGKYKRDQLPTGATRLGENPNRGQESYGPR<br>NEQERTWRIIAAVEAVAKALGVSMAQVALAWLADRPAVTSVILGARTREQLADNLAAADLR<br>LDAEHAQQLTDASAPEVADYPYGKGGVNQRHRKIAGGR<br>Total amino acids: 343 |
| 7 | SEQ ID NO. 7 | MEYRKLGNSGAIVTNYCLGTMTFGKESDEATSFRLMDDYVAAGGNFIDTANVYSDGLSEQII<br>GGWLKSKPGILRDLVITTKGRFPMGDGPNHLGLSRKNLSEALDASLKRLGVEHIDLYQLHAF<br>DALTPIEETLRFLDDSIRNGKIAYYGFSNFLGWQMTKAVWIAKAGNFQPPVTLQPQYNLLAR<br>DIEHEWPAALDAGIGLLPWSPLGGGWLSGKYKRDQMPSGATRLGENPKRGLEAFEKRNA<br>NPATWQVIGALEDIAKARGASMAQVALAWLVKRPAVTSVILGARTAEQLADNLGAADVTLS<br>DDEMRTLTEMSAPQVADYPYGEGGNRQRNRRMEGGR<br>Total amino acids: 343 |
| 8 | SEQ ID NO. 8 | MDYRKLGNSGAWSSYCLGTMTFGAEADEATSHLLLDDYVEAGGNFIDTANVYSLGVSEEII<br>GRWLKAKPEAASNLVIASKGRFPMGAGPNDLGLSRKHLNRALDDSLKRLGVEQIDLYQMH<br>AWDALTPIEETLRFLDDSIGAGKIAYYGFSNYLGWQVTKAVHVAKANHWSAPVTLQPQYNL<br>LVRDIEHEIVPACLDAGMGLLPWSPLGGGWLAGKYQRDVMPSGATRLGENPNRGMESFG<br>PRNAQERTWQIIDAVAEIAKDRGASAAQVALAWVEARPAVTSVILGARTREQLADNLGSSK<br>VKLSAEETDKLTRISMPQMSDYPYGERGVSQRFRKMEGGR<br>Total amino acids: 343 |
| 9 | SEQ ID NO. 9 | MEYRKLGNSGTIVTSYCLGTMTFGAEADETTSHLILDDYVEAGGNFIDTANVYSLGVSEEIV<br>GRWLKARPEAASQVVLASKGRFPMGAGPNDLGLSRKHLNRALDDSLKRLGVEQIDLYQMH<br>AWDALTPIEETLRFLDDSIGAGKIAYYGFSNYLGWQLTKAVHLAKLNHWSAPVTLQPQYNLL<br>VRDIEHEIVPACLDAGMGLLPWSPLGGGWLAGKYQRDVMPSGATRLGENPNRGMESFGP<br>RNAQDRTWQIIDAVADIAKDRGVSAAQVALAWVEARPAVTSVILGARTREQLADNLGSSKL<br>KLSAEDTDKLSRASMPQMSDYPYGERGISQRFRKMEGGR<br>Total amino acids: 350 |
| 10 | SEQ ID NO. 10 | MEYRKLGNSGTIVTSYCLGTMTFGAEADETTSHLLLDDYVEAGGNFIDTANVYSLGVSEEII<br>GRWLKAKPEAASQVVIASKGRFPMGAGPNDLGLSRKHLNRALDDSLRRLGVEQIDLYQMH<br>AWDALTPIEETLRFLDDSIGAGKIAYYGFSNYLGWQLTKAVHLAKLNHWSAPVTLQPQYNLL<br>VRDIEHEIVPACLDAGMGLLPWSPLGGGWLSGKYQRDVMPSGATRLGENPNRGMESFGP<br>RNAQERTWQIIDAVAEIAKDRGASAAQVALAWVEARPAVTSVILGARTREQLADNLGSSKV<br>KLSAEETDKLTRISMPQMSDYPYGERGVSQRFRKMEGGR<br>Total amino acids: 343 |
| 11 | SEQ ID NO. 11 | MEYRKLGNSGTIVSSYCLGTMTFGAEADEATSHLILDDYVEAGGNFIDTANVYSLGVSEEIIG<br>RWLKARPEAASNVVLASKGRFPMGAGPNDLGLSRKHLNRALEDSLKRLGVEQIDLYQMHA<br>WDALTPIEETLRFLDDAVGAGKIAYYGFSNYLGWQLTKAVHLAKANHWSAPVTLQPQYNLL<br>VRDIEHEIVPACLDAGMGLLPWSPLGGGWLAGKYQRDVMPSGATRLGENPNRGMEAFGP<br>RNAQDRTWQIIDAVADIAKDRGVSAAQVALAWVEARPAVTSVILGARTREQLADNLGSSKL<br>KLSAEDTDKLSRISMPQMSDYPYGERGISQRFRKMEGGR<br>Total amino acids: 343 |
| 12 | SEQ ID NO. 12 | MEYRKLGNSGTIVTSYCLGTMTFGAEADETTSHLILDDYVEAGGNFIDTANVYSLGVSEEIIG<br>RWLKAKPEAASNLVIASKGRFPMGAGPNDLGLSRKHLNRALDDSLKRLGVEQIDLYQMHA<br>WDALTPIEETLRFLDDAVGAGKIAYYGFSNYLGWQLTKAVHLAKLNHWSAPVTLQPQYNLL<br>VRDIEHEIVPACLDAGMGLLPWSPLGGGWLAGKYQRDVMPSGATRLGENPNRGMESFGP<br>RNAQDRTWQIIDAVADIAKDRGVSAAQVALAWVEARPAVTSVILGARTREQLADNLGSSKV<br>KLSAEETDKLTRISMPQMSDYPYGERGVSQRFRKMEGGR<br>Total amino acids: 343 |
| 13 | SEQ ID NO. 13 | MDYRKLGNSGTWTSYCLGTMTFGAEADEATSHLILDDYVEAGGNFIDTANVYSLGVSEEII<br>GRWLKARPEAASNVVIATKGRFPMGAGPNDLGLSRKHLNRALEDSLKRLGVEQIDLYQMH<br>AWDALTPIEETLRFLDDAIGAGKIAYYGFSNYLGWQVTKAVHLAKANHWSAPVTLQPQYNL<br>LVRDIEHEIVPACLDAGMGLLPWSPLGGGWLSGKYQRDVMPSGATRLGENPNRGMEAFG |

TABLE 2-continued

Depicting sequences as described herein.

| # | Synonym | Sequence |
|---|---|---|
| | | PRNAQDRTWQIIDAVAEIAKDRGVSAAQVALAWVEARPAVTSVILGARTREQLADNLGSSK VKLSAEDTDKLTRASMPQMSDYPYGERGVSQRFRKMEGGR Total amino acids: 343 |
| 14 | SEQ ID NO. 14 | MEYRKLGNSGAIVTSYCLGTMTFGAEADETTSHLLLDDYVEAGGNFIDTANVYSLGVSEEII GRWLKARPEAASNVVLATKGRFPMGAGPNDLGLSRKHLNRALEDSLKRLGVEQIDLYQMH AWDALTPIEETLRFLDDSVGAGKIAYYGFSNYLGWQVTKAVHLAKANHWSAPVTLQPQYNL LVRDIEHEIVPACLDAGMGLLPWSPLGGGWLSGKYQRDVMPSGATRLGENPNRGMEAFG PRNAQDRTWQIIDAVAEIAKDRGVSAAQVALAWVEARPAVTSVILGARTREQLADNLGSSK VKLSAEDTDKLTRASMPQMSDYPYGERGVSQRFRKMEGGR Total amino acids: 343 |
| 15 | SEQ ID NO. 15 | MDYRKLGNSGAWSSYCLGTMTFGAEADEATSHLLLDDYVEAGGNFIDTANVYSLGVSEEI VGRWLKARPEAASQVVLATKGRFPMGAGPNDIGLSRKHLNRALEDSLRRLGVEQIDLYQM HAWDALTPIEETLRFLDDSIGAGKIAYYGFSNYLGWQLTKAVHLAKLNHWSAPVTLQPQYN LLVRDIEHEIVPACLDAGMGLLPWSPLGGGWLSGKYQRDVMPSGATRLGENPNRGMESF GPRNAQERTWQIIDAVAEIAKDRGASAAQVALAWVEARPAVTSVILGARTREQLADNLGSS KSKLSAEDTDKLTRISMPQMSDYPYGERGISQRFRKMEGGR Total amino acids: 343 |
| 16 | SEQ ID NO. 16 | MEYRKLGNSGTIVTSYCLGTMTFGAEADETTSHLILDDYVEAGGNFIDTANVYSLGVSEEIIG RWLKAKPEAASNLVIASKGRFPMGAGPNDLGLSRKHLNRALDDSLKRLGVEQIDLYQMHA WDALTPIEETLRFLDDAVGAGKIAYYGFSNYLGWQVTKAVHVAKANHWSAPVTLQPQYNLL VRDIEHEIVPACLDAGMGLLPWSPLGGGWLAGKYQRDVMPSGATRLGENPNRGMEAFGP RNAQDRTWQIIDAVADIAKDRGVSAAQVALAWVEARPAVTSVILGARTREQLADNLGSSKV KLSAEETDKLTRISMPQMSDYPYGERGVSQRFRKMEGGR Total amino acids: 343 |
| 17 | SEQ ID NO. 17 | MDYRKLGNSGTIVTSYCLGTMTFGAEADEATSHLLLDDYVEAGGNFIDTANVYSLGVSEEII GRWLKAKPEAASNLVIASKGRFPMGAGPNDLGLSRKHLNRALDDSLKRLGVEQIDLYQMH AWDALTPIEETLRFLDDAVGAGKIAYYGFSNYLGWQVTKAVHVAKANHWSAPVTLQPQYN LLVRDIEHEIVPACLDAGMGLLPWSPLGGGWLSGKYQRDVMPSGATRLGENPNRGMESF GPRNAQDRTWQIIDAVAEIAKDRGVSAAQVALAWVEARPAVTSVILGARTREQLADNLGSS KLKLSAEETDKLTRISMPQMSDYPYGERGVSQRFRKMEGGR Total amino acids: 343 |
| 18 | SEQ ID NO. 18 | MEYRKLGNSGTIVTSYCLGTMTFGAEADEATSHLLLDDYVEAGGNFIDTANVYSLGLSEQII GRWLKAKPEAASQVVIASKGRFPMGAGPNDLGLSRKHLNRALDDSLKRLGVEQIDLYQMH AWDALTPIEETLRFLDDAVGAGKIAYYGFSNYLGWQLTKAVHVAKANHWSAPVTLQPQYNL LARDIEHEIVPACLDAGMGLLPWSPLGGGWLAGKYQRDVMPTGATRLGENPNRGMEAFG PRNAQERTWQIIDAVAEIAKDRGASAAQVALAWVEARPAVTSVILGARTREQLADNLGSVK VKLSAEETDKLTRISMPQMSDYPYGERGVSQRFRRMEGGR Total amino acids: 343 |
| 19 | SEQ ID NO. 19 | MDYRKLGNSGAWSNLCLGTMTFGDEADEATSFLLMDQYVEAGGNFLDTADVYSTGVSEE IIGRWLKAKRLRNLVIASKGRFPMGNGPNHLGLSRKHLGEALDASLQRLGVEQIDLYQMHA WDALTPLEETLRFLDDSIRSGKIAYYGFSNFLGWHLTKAVWMAKLNGYAAPVTLQPQYNLL VRDIEHEWPACEDAGMGLLPWSPLGGGWLSGKYKRDQMPEGATRLGENPKRGMEAYE GRNAQDRTWSIIGAVEDIAKAQDVTMAQVALAWTAARPAVTSVILGARTAEQLKDNLGAAD LVLSEADMERLNAVSAPQMADYPYGTGGIGQRNRKIEGGR Total amino acids: 341 |
| 20 | SEQ ID NO. 20 | MDYRKLGNSGAWSNLCLGTMTFGDEADEATSFVLMDQYVEAGGNFLDTADVYSAGLSEE IVGRWLKGKKLRDLVIATKGRFPMGNGPNHLGLSRKHLGEALDASLQRLGVEQIDLYQMHA WDALTPLEETLRFLDDSIRSGKIAYYGFSNFLGWHLTKAVWMAKLNGYAAPVTLQPQYNLL VRDIEHEWPACEDAGMGLLPWSPLGGGWLSGKYKRDQMPEGATRLGENPKRGMEAYE GRNAQDRTWSIIGAVEDIAKAQNVSMAQVALAWTVARPAVTSVILGARTAEQLKDNLGSVD LVLSEADMERLNAASAPQMSDYPYGTGGIGQRNRKLEGGR Total amino acids: 341 |
| 21 | SEQ ID NO. 21 | MDYRKLGNSGAWSNLCLGTMTFGDEADEATSFLLMDQYVEAGGNFLDTADVYSTGVSEE IIGRWLKGKKLRDLVIATKGRFPMGQGPNHLGLSRKHLGEALDASLQRLGVEQIDLYQMHA WDALTPLEETLRFLDDSIRSGKIAYYGFSNFLGWHLTKAVWMAKLNGYAAPVTLQPQYNLL VRDIEHEWPACEDAGMGLLPWSPLGGGWLSGKYKRDQMPEGATRLGENPKRGMEAYE GRNAQDRTWSIIGAVEDIAKAQDVTMAQVALAWTAARPAVTSVILGARTAEQLKDNLGSVD LVLSEADMERLNAASAPQMSDYPYGTGGIGQRNRKLEGGR Total amino acids: 341 |
| 22 | SEQ ID NO. 22 | MDYRKLGNSGAWVSNLCLGTMTFGDEADEATSFVLMDQYVEAGGNFLDTADVYSAGLSEE IIGRWLKAKRLRNLVIASKGRFPMGNGPNHLGLSRKHLGEALDASLQRLGVEQIDLYQMHA WDALTPLEETLRFLDDAIRSGKIAYYGFSNFLGWHITKAVWMARAQGYAAPVTLQPQYNLL VRDIEHEWPACEDAGMGLLPWSPLGGGWLSGKYKRDQMPEGATRLGENPKRGMEAYE GRNAQDRTWSIIGAVEDIAKAQNVSMAQVALAWTAARPAVTSVILGARTAEQLKDNLGSVD LVLSEADMERLNAASAPQMSDYPYGTGGIGQRNRKLEGGR Total amino acids: 341 |

TABLE 2-continued

Depicting sequences as described herein.

| # | Synonym | Sequence |
|---|---|---|
| 23 | SEQ ID NO. 23 | MDYRKLGNSGAWSNLCLGTMTFGDEADEATSFLLMDQYVEAGGNFLDTADVYSAGVSEE<br>IVGRWLKAKKLRNLVIATKGRFPMGNGPNHLGLSRKHLGEALDASLQRLGVEQIDLYQMHA<br>WDALTPLEETLRFLDDAIRSGKIAYYGFSNFLGWHITKAVWMAKANGYAAPVTLQPQYNLL<br>VRDIEHEWPACEDAGMGLLPWSPLGGGWLSGKYKRDQMPEGATRLGENPKRGMEAYE<br>GRNAQERTWSIIGAVEDIAKAQDVSMAQVALAWTAARPAVTSVILGARTAEQLKDNLGSAD<br>LVLSEADMERLNAASAPQMADYPYGTGGIGQRNRKLEGGR<br>Total amino acids: 341 |
| 24 | SEQ ID NO. 24 | MDYRKLGNSGAWSNLCLGTMTFGDEADEATSFVLMDQYVEAGGNFLDTADVYSTGLSEE<br>IIGRWLKGKRLRDLVIASKGRFPMGQGPNHLGLSRKHLGEALDASLQRLGVEQIDLYQMHA<br>WDALTPLEETLRFLDDSVRSGKIAYYGFSNFLGWHLTKAVWMARLQGYAAPVTLQPQYNL<br>LVRDIEHEVVPACEDAGMGLLPWSPLGGGWLSGKYKRDQMPEGATRLGENPKRGMEAYE<br>GRNAQDRTWAIIGAVEDIAKAQNVTMAQVALAWTVARPAVTSVILGARTAEQLKDNLGAVD<br>LVLSEADMERLNAVSAPQMSDYPYGTGGIGQRNRKIEGGR<br>Total amino acids: 341 |
| 25 | SEQ ID NO. 25 | MDYRKLGNSGAVVSNLCLGTMTFGDEADEATSFLLMDQYVEAGGNFLDTADVYSAGLSEE<br>IIGRWLKAKRLRDLVIATKGRFPMGNGPNHLGLSRKHLGEALDASLQRLGVEQIDLYQMHA<br>WDALTPLEETLRFLDDAVRSGKIAYYGFSNFLGWHLTKAVWMAKAQGYAAPVTLQPQYNL<br>LVRDIEHEWPACEDAGMGLLPWSPLGGGWLSGKYKRDQMPEGATRLGENPKRGMEAYE<br>GRNAQDRTWAIIGAVEDIAKAQDVSMAQVALAWTVARPAVTSVILGARTAEQLKDNLGSAD<br>LVLSEADMERLNAVSAPQMSDYPYGTGGIGQRNRKLEGGR<br>Total amino acids: 341 |
| 26 | SEQ ID NO. 26 | MDYRKLGNSGAVVSNLCLGTMTFGDEADEATSFLLMDQYVEAGGNFLDTADVYSTGVSEE<br>IVGRWLKGKKLRDLVIATKGRFPMGQGPNHLGLSRKHLGEALDASLQRLGVEQIDLYQMHA<br>WDALTPLEETLRFLDDAVRSGKIAYYGFSNFLGWHLTKAVWMAKLNGYAAPVTLQPQYNLL<br>VRDIEHEWPACEDAGMGLLPWSPLGGGWLSGKYKRDQMPEGATRLGENPKRGMEAYE<br>GRNAQERTWAIIGAVEDIAKAQDVTMAQVALAWTVARPAVTSVILGARTAEQLKDNLGSVD<br>LVLSEADMERLNAASAPQMADYPYGTGGIGQRNRKIEGGR<br>Total amino acids: 341 |
| 27 | SEQ ID NO. 27 | MDYRKLGNSGAVVSNLCLGTMTFGDEADEATSFLLMDQYVEAGGNFLDTADVYSTGLSEE<br>IIGRWLKAKKLRDLVIASKGRFPMGNGPNHLGLSRKHLGEALDASLQRLGVEQIDLYQMHA<br>WDALTPLEETLRFLDDSIRSGKIAYYGFSNFLGWHLTKAVWMARANGYAAPVTLQPQYNLL<br>VRDIEHEWPACEDAGMGLLPWSPLGGGWLSGKYKRDQMPEGATRLGENPKRGMEAYE<br>GRNAQDRTWSIIGAVEDIAKAQDVTMAQVALAWTVARPAVTSVILGARTAEQLKDNLGAAD<br>LVLSEADMERLNAVSAPQMADYPYGTGGIGQRNRKIEGGR<br>Total amino acids: 341 |
| 28 | SEQ ID NO. 28 | MDYRKLGNSGAVVSNLCLGTMTFGDEADEATSFVLMDQYVEAGGNFLDTADVYSTGVSE<br>EINGRWLKGKKLRDLVIATKGRFPMGNGPNHLGLSRKHLGEALDASLQRLGVEQIDLYQMH<br>AWDALTPLEETLRFLDDSIRSGKIAYYGFSNFLGWHLTKAVWMAKLNGYAAPVTLQPQYNL<br>LVRDIEHEVVPACEDAGMGLLPWSPLGGGWLSGKYKRDQMPEGATRLGENPKRGMEAYE<br>GRNAQERTWAIIGAVEDIAKAQDVTMAQVALAWTAARPAVTSVILGARTAEQLKDNLGAVD<br>LVLSEADMERLNAASAPQMSDYPYGTGGIGQRNRKIEGGR<br>Total amino acids: 341 |
| 29 | SEQ ID NO. 29 Described by Carere et al. (2018) cited herein (DmDepB from *D. mutans* 17-2-E-8) | MEYRKLGNSGTVVTSYCLGTMTFGQETDEATSHLIMDDYIKAGGNFIDTANVYSAGVSEEIV<br>GRWLKARPSEARQVWATKGRFPMGAGPNDLGLSRTNLNRALNDSLRRLGVEQIDLYQM<br>HAWDAVTPIEETLRFLDDAVSAGKIAYYGFSNYLGWQVTKAVHVARANHWTAPVTLQPQY<br>NLLVRDIEHEIVPACQDAAMGLLPWSPLGGGWLAGKYQRDVMPSGATRLGENPNRGMES<br>YGPRNAQERTWQIIDMVAEIAKERGVSAAQVALAWWARPAVTAVILGARTREQLADNLGA<br>VAVTLSTEEMERLNRVSAPAMADYPYGERGVSQRHRKMDGGR<br>Total amino acids: 343 |
| 30 | SEQ ID NO. 30 described in WO2019/046954 (DepB enzyme from *Rhizobium leguminosarum* (RIDepB)) | MDYRKLGPSGTVVTAYCLGTMTGAEADEAASHKLLDDYFAWGGNFIDTADVYSAGKSEEII<br>GRWLKARPTEARQAIVATKGRFPMGNGPNDIGLSRRHLSQALDDSLRRLGLEQIDLYQMH<br>AWDALTPIEETLRFLDDAVSSGKIGYYGFSNYVGWHIAKASEIAKARGYTRPVTLQPQYNLL<br>MRDIELEIVAACQDAGMGLLPWSPLGGGWLTGKYKRDEMPTGATRLGENPNRGGESYAP<br>RNAQERTWAIIGTVEEIAKARGVSMAQVALAWTAARPAITSVILGARTPEQLADNLGAMKVE<br>LSGEEMARLNEVSAPQPLDYPYGKGGINQRHRKIEGGR<br>Total amino acids: 342 |

TABLE 2-continued

Depicting sequences as described herein.

| # | Synonym | Sequence |
|---|---|---|
| 31 | SEQ ID NO. 31 | YRKLGNSG |
| 32 | SEQ ID NO. 32 | LGTMTFG |
| 33 | SEQ ID NO. 33 | AGGNF$X_1$DTA$X_2$VYS<br>$X_1$ = I or L<br>$X_2$ = N or D |
| 34 | SEQ ID NO. 34 | ETLRFLDD |
| 35 | SEQ ID NO. 35 | GKI$X_3$YYGFSN<br>$X_3$ = A or G |
| 36 | SEQ ID NO. 36 | RDIEHE$X_4$VPA<br>$X_4$ = I or V |
| 37 | SEQ ID NO. 37 | GLLPWSPLGGGWL |
| 38 | SEQ ID NO. 38 | GATRLGENP |
| 39 | SEQ ID NO. 39 | AQVALAW |
| 40 | SEQ ID NO. 40 | PAV$X_5$SVILGART<br>$X_5$ = T or A |
| 41 | SEQ ID NO. 41 (SEQ ID NO. 1 of WO2016/154640) | MRFEYLRQNVVGLALSTALIASLSGPAFAQHDANAAAEPSKAGQSAIENFQPVTADDLAGK<br>NPANWPILRGNYQGWGYSPLDQINKDNVGDLQLVWSRTMEPGSNEGAAIAYNGVIFLGNT<br>NDVIQAIDGKTGSLIWEYRRKLPSASKFINSLGAAKRSIALFGDKVYFVSWDNFVVALDAKT<br>GKLAWETNRGQGVEEGVANSSGPIWDGWIAGSTCQFSGFGCYVTGTDAESGEELWRN<br>TFIPRPGEEGDDTWGGAPYENRWMTGAWGQITYDPELDLVYYGSTGAGPASEVQRGTEG<br>GTLAGTNTRFAVKPKTGEVVWKHQTLPRDNWDSECTFEMMVVSTSVNPDAKADGMMSV<br>GANVPRGETRKVLTGVPCKTGVAWQFDAKTGDYFWSKATVEQNSIASIDDTGLVTVNEDM<br>ILKEPGKTYNYCPTFLGGRDWPSAGYLPKSNLYVIPLSNACYDVMARTTEATPADVYNTDA<br>TLVLAPGKTNMGRVDAIDLATGETKWSYETRAALYDPVLTTGGDLVFVGGIDRDFRALDAE<br>SGKEVWSTRLPGAVSGYTTSYSIDGRQYVAVVSGGSLGGPTFGPTTPDVDSASGANGIYV<br>FALPEKK |
| 42 | SEQ ID NO. 42 (SEQ ID NO. 7 of WO2019/046954) | MKKRTSILLASVAMLGMGSTAFAQVDINALPAVTDAILANPDAGDWPSYGRDITNYRFSPLD<br>QVNKDNVGQLTLAWARALEPGNLQSAPLEFGGVLFTAAPGDVVQAMDAATGQLIWEYRR<br>QLPDRATLNSLGENKRGIALYEDKIYVATWDNFIVALDAKTGQVAWESDRGGGADLISNTT<br>GPIVANGWVAGSTCQFSEFGCYVTGHDAATGEELWRNNFIPKKGEEGDDTWGDSTEDQ<br>RWMTGAWGQMTYDPELDLVYYGSTGAGPAAEFQRNTVGGTLFGSNTRFAVKPKTGEIVW<br>RHQVLPRDNWDQECTYEMVPVDIDSAPAADMEGLLALGTAAPGKKRVLTGVPCKTGVMW<br>QFDAQTGEFIYARDTVQQTLIESVDNTGLVTVNEAAIPTEVDVATPMCPTYLGGRDWSPTA<br>FNPTSKVMFVPLTNMCADVTVLDQEPTGLDVYNTELTYKMPEGVTDAGRIDAINVETGKTL<br>WSWTQQTPQYASITATAGGLIFTGGADRRFKAIDQETGELVWSVTLGSRATGHPISYEVDG<br>RQYIAIPAGGPGYATDLITASGSTVDVVSGSNMLYVFALPEQKK |

EXAMPLES OF THE INVENTION

Example 1: Determination of pH Optimum

To determine the catalytic pH optimum of a polypeptide as referred to herein, reactions for the transformation of 3-keto-DON at different pH values were prepared. To this end, 16 reactions of different pH values were prepared to a final volume of 200 µL each. A polypeptide having the amino acid sequence of SEQ ID NO: 1 was used at a final concentration of 200 nM. As substrate, 3-keto-DON was used at a final concentration of 30 ppm, and NADPH was used at a final concentration of 1 mM. As buffer, Teorell Stenhagen (TS) buffer was used (Stenhagen & Teorell. 1938. Nature 141, 415) and set to a pH of either 2.5, 3.0, 3.5, 4.0, 4.5, 5.0, 5.5, 6.0, 6.5, 7.0, 7.5, 8.0, 8.5, 9.0, 9.5, 10.0. Specifically, the TS buffer contained: 68.6 mM NaOH, 10,255 mM phosphoric acid, 7,287 mM citric acid, 11.45 mM boric acid and approximately 17-63 mM HCl to achieve the required pH. The transformation reactions were incubated at 30° C. for 120 min, and started by the addition of the NADPH. Throughout the incubation, 20 µL samples were drawn at 0 min, 10 min, 20 min, 30 min, 60 min and 120 min. The sample at 0 min was drawn prior to the addition of the NADPH. The 20 µL samples were immediately mixed with 20 µL of 100% methanol to stop the transformation reaction, and then kept on ice until the end of the incubation.

Prior to analysis by LC-MS/MS, all samples were diluted with 40% methanol in water to a final concentration of maximum 0.3 ppm 3-keto-DON. In particular, in this experimental setup 30 ppm 3-keto DON were used as starting material. When stopping the reaction with methanol a 1:2 dilution has been achieved (20 μl+20 μl) resulting in a concentration of 15 ppm 3-keto DON in the sample. A further 1:50 dilution results in a concentration of 0.3 ppm 3-keto DON.

For LC-MS/MS analysis, DON, 3-keto-DON and 3-epi DON were separated on a 150 mm×2.1 mm Phenomenex Kinetex Biphenyl column with a particle size of 2.6 μm (100 Å). The mobile phase consisted of a mixture of methanol and ultrapure water (conductivity of max. 0.055 μS/cm) with 0.1% (v/v) acetic acid. Ions were generated using electro spray ionization (ESI) in negative ionization mode. The quantification was done using a QTrap and/or triple quadrupole mass detector. Notably, the so-called QTRAP mass detectors are triple quadrupole mass detector from Sciex having a better scan function to ease the detection and quantification of low amounts of analytes. If necessary, samples were diluted to fall into the linear range of this method which ranges from analyte concentrations of 1 ppb to 500 ppb in the injected sample. The limit of quantification (LOQ) was the limit of reliable detection, and concentrations below 1 ppb of compound detected in a sample were not considered as reliable, resulting in a LOQ of 1 ppb. In case the concentration of the analyte was below the LOQ, all further calculations (e.g. for determination of the specific) activity or ratio of analytes) were made with 1 ppb. Kinetic parameters were calculated based on the determined amounts of 3-epi-DON and/or DON from the individual sample time points.

Specific activities were calculated during the linear range of each reaction.

For the determination of the linear range of the reaction the following procedure was applied. From the individual sample time points, a curve is plotted into a graph (x-axis=time, y-axis=amount of 3-epi-DON or DON). Then in this graph the time frame in which the curve has a linear shape is identified.

Then the molecular weight of the enzyme in kDa is multiplied with the enzyme concentration in μM used in the experiment (here 0.2=mg enzyme in 1 ml of a 0.2 μM solution). The latter value is then shifted to the actual reaction volume—here 200 μl—to obtain the amount of enzyme in the reaction in mg (4 amount of enzyme e [mg]).

The concentration of the product 3-epi DON/DON in ppm (=mg/L) for a given time point z (selected to fall into the linear range of the reaction) is also converted into absolute values, namely μg in the reaction volume. This value is then divided by the molecular weight of the product (296.32 g/mol for both 3-epi DON and DON). In this way the unit is shifted from [μg] to [μmol]($\rightarrow$amount of product p [μmol]).

For the determination of the (specific) activity the following calculation is performed a=p/z/e. The (specific) activity has the unit [μmol$_{product}$/min/mg$_{enzyme}$].

The specific activities for the formation of 3-epi-DON at different pH values are shown in Table 3 below.

TABLE 3

| Specific activities of a polypeptide having the amino acid sequence of SEQ ID NO: 1 at different pH values, in μmol of 3-epi-DON formed per min and per mg of polypeptide. | |
| --- | --- |
| pH | μmol/min/mg |
| 2.5 | 0.000 |
| 3.0 | 0.000 |
| 3.5 | 0.000 |

TABLE 3-continued

| Specific activities of a polypeptide having the amino acid sequence of SEQ ID NO: 1 at different pH values, in μmol of 3-epi-DON formed per min and per mg of polypeptide. | |
| --- | --- |
| pH | μmol/min/mg |
| 4.0 | 0.007 |
| 4.5 | 0.020 |
| 5.0 | 0.082 |
| 5.5 | 0.133 |
| 6.0 | 0.201 |
| 6.5 | 0.243 |
| 7.0 | 0.199 |
| 7.5 | 0.181 |
| 8.0 | 0.154 |
| 8.5 | 0.197 |
| 9.0 | 0.137 |
| 9.5 | 0.127 |
| 10.0 | 0.114 |

The polypeptide was found active in a pH range from pH 4.5 to pH 10, with an optimum of 3-epi-DON formation at pH 6.5.

The stereoselectivity was determined by putting the total product formation (DON+3-epi-DON) at 100%. Then the portion of the obtained product DON or 3-epi-DON was determined in relation to the total amount of product (100%).

Example 2: Determination of Temperature Optimum

To determine the catalytic temperature optimum of a polypeptide as referred to herein, reactions for the transformation of 3-keto-DON at different temperatures were prepared. To this end, 24 reactions were prepared to a final volume of 180 μL each. A polypeptide having the amino acid sequence of SEQ ID NO. 1 was used at a final concentration of 200 nM. As substrate, 3-keto-DON was used at a final concentration of 30 ppm, and NADPH was used at a final concentration of 1 mM. As buffer, TS buffer was used at pH 7.0. The buffer was prepared as described in Teorell and Stenhagen (1938) "Ein Universalpuffer für den pH-Bereich 2.0 bis 12.0." Biochem Z.; 299:416-419. The transformation reactions were incubated in a laboratory PCR-thermocycler at different temperatures for 120 min, and started by the addition of the NADPH. Throughout the incubation, 20 μL samples were drawn at 0 min, 5 min, 10 min, 20 min, 30 min, 60 min and 120 min. The sample at 0 min was drawn from the reactions prior to the addition of the NADPH. The 20 μL samples were immediately mixed with 180 μL of 100% methanol to stop the transformation reaction, and then kept on ice until the end of the incubation.

Analyses were performed by LC-MS/MS as described in Example 1.

The specific activities for the formation of 3-epi-DON at different temperatures are shown in Table 4 below.

TABLE 4

| Specific activities of a polypeptide having the amino acid sequence of SEQ ID NO: 1 at different temperatures, in μmol of 3-epi-DON formed per min and per mg of polypeptide. | |
| --- | --- |
| Temperature ° C. | μmol/min/mg |
| 14.9 | 0.106 |
| 15.0 | 0.094 |
| 16.0 | 0.089 |

TABLE 4-continued

Specific activities of a polypeptide having the amino acid sequence of SEQ ID NO: 1 at different temperatures, in μmol of 3-epi-DON formed per min and per mg of polypeptide.

| Temperature ° C. | μmol/min/mg |
|---|---|
| 17.8 | 0.109 |
| 20.1 | 0.116 |
| 22.7 | 0.114 |
| 25.5 | 0.116 |
| 28.3 | 0.127 |
| 31.0 | 0.118 |
| 33.3 | 0.100 |
| 35.0 | 0.098 |
| 36.0 | 0.088 |
| 34.9 | 0.105 |
| 35.2 | 0.102 |
| 36.3 | 0.085 |
| 38.0 | 0.092 |
| 40.3 | 0.076 |
| 42.9 | 0.059 |
| 45.7 | 0.040 |
| 48.4 | 0.031 |
| 51.0 | 0.017 |
| 53.2 | 0.015 |
| 54.8 | 0.018 |
| 55.7 | 0.019 |

Most 3-epi-DON was formed by the polypeptide at temperatures from 14.9° C. to 55.7° C.

Example 3: Alignment and Identity of SEQ ID NO. 1-28

ClustalO alignment of SEQ ID NOs 1-28. The results of this sequence alignment are shown in FIG. 1. In FIG. 2 ClustalO sequence identities are depicted. For all of SEQ ID NOs 1-28 as well as for prior art enzymes of SEQ ID NO. 29 and SEQ ID NO. 30 the specific) activity as well as the stereoselectivity (based on the total amount of 3-epi-DON (3ED) and DON measured as described in Example 1) was determined as described in Example 1. The results are shown in FIG. 3.

LIST OF REFERENCES

Altschul, J. Mol. Biol. 215 (1990), 403-410

Altschul et al., 1997 (Nucleic Acids Res. (1997) 25:3389-3402

Carere et al. (2018) "The identification of DepB: An enzyme responsible for the final detroxification Step in the deoxynivalenol epimerization pathway in *Devosia mutans* 17-2-E-8." Frontiers in Microbiology. 9:1573

Hassan et al. (2017) "The enzymatic epimerization of deoxynivalenol by *Devosia mutans* proceeds through the formation of 3-keto-DON intermediate." Scientific Reports 7, article number 6929

He et al. (2015) "Toxicology of 3-epi-deoxynivalenol, a deoxynivalenol-transformation product by *Devosia mutans* 17-2-E-8." Food and Chemical Toxicology 84: 250-259

He et al. (2020) "A quinone-dependent dehydrogenase and two NADPH-dependent aldo/keto reductases detoxify deoxynivalenol in wheat via epimerization in a *Devosia* strain." Food Chemistry, 321:126703.

Henikoff Proc. Natl. Acad. Sci., USA, 89, (1989), 10915

Henikoff and Henikoff (1992) 'Amino acid substitution matrices from protein blocks.' Proc Natl Acad Sci USA. 1992 Nov. 15; 89(22):10915-9

Kurtzman (2009) "Biotechnological strains of *Komagataella* (*Pichia*) *pastoris* are *Komagataella* phaffii as determined from multigene sequence analysis." J Ind Microbiol Biotechnol. 36(11):1435-8

Payros et al., (2016) "Toxicology of deoxynivalenol and its acetylated and modified forms." Archives of Toxicology 90(12): 2931-2957)

Pierron et al., (2016) "Microbial biotransformation of DON: molecular basis for reduced toxicity." Scientific Reports 6(1))

POST-TRANSLATIONAL COVALENT MODIFICATION OF PROTEINS, B. C. Johnson, Ed., Academic Press, New York (1983), pgs. 1-12

PROTEINS—STRUCTURE AND MOLECULAR PROPERTIES, 2nd Ed., T. E. Creighton, W. H. Freeman and Company, New York (1993)

Rattan, Ann. NY Acad. Sci. 663 (1992); 48-62

Schatzmayr and Streit (2013) 'Global occurrence of mycotoxins in the food and feed chain: Facts and figures.' World Mycotoxin Journal 6(3):213-222

Seifter, Meth. Enzymol. 182 (1990); 626-646

Teorell and Stenhagen (1938) "Ein Universalpuffer für den pH-Bereich 2.0 bis 12.0." Biochem Z.; 299:416-419

Thompson Nucl. Acids Res. 2 (1994), 4673-4680) or FASTDB (Brutlag Comp. App. Biosci. 6 (1990), 237-245

WO2019/046954

Yamada et al. (1995) 'The Phylogenetic Relationships of Methanol-assimilating Yeasts Based on the Partial Sequences of 18S and 26S Ribosomal RNAs: The Proposal of *Komagataella* Gen. Nov. (Saccharomycetaceae)' Bioscience, Biotechnology and Biochemistry, Vol. 59, issue 3, pp. 439-444

Zdarta et al. (2018) "A general overview of support materials for enzyme immobilization: characteristics, properties, practical utility" Catalysts 8, 92, p. 1-27.

The invention claimed is:

1. A method of converting 3-keto-DON into 3-epi-DON, the method comprising contacting one or more polypeptide (s) comprising or consisting of: (a) SEQ ID NO: 1, or (b) a sequence having a sequence identity of at least 72.0% to SEQ ID NO: 1, with 3-keto DON, wherein the polypeptide comprises one or more of the following polypeptide sequences:

(i) (SEQ ID NO. 31)
YRKLGNSG;

(ii) (SEQ ID NO. 32)
LGTMTFG;

-continued (iii) (SEQ ID NO. 33)
AGGNF$X_1$DTA$X_2$VYS, wherein $X_1$ is I or L and $X_2$ is N or D;

(iv) (SEQ ID NO. 34)
ETLRFLDD;

(v) (SEQ ID NO. 35)
GKI$X_3$YYGFSN, wherein $X_3$ is A or G;

(vi) (SEQ ID NO. 36)
RDIEHE$X_4$VPA, wherein $X_4$ = I or V;

(vii) (SEQ ID NO. 37)
GLLPWSPLGGGWL;

-continued (viii)

(SEQ ID NO. 38)

GATRLGENP;

(ix)

(SEQ ID NO. 39)

AQVALAW;
and/or (x)

(SEQ ID NO. 40)

$PAVX_5SVILGART$, wherein $X_5$ = T or A.

2. The method of claim 1, wherein the polypeptide comprises 2, 3, 4, 5, 6, 7, 8, or 9 of polypeptide sequences (i)-(x).

3. The method of claim 1, wherein the polypeptide is capable of converting the substrate 3-keto-DON into the product 3-epi-DON and into the product DON with a ratio of the activity of the polypeptide for DON to the activity of the polypeptide for 3-epi-DON (DON: 3-epi-DON) between 0.045 and 0.26.

4. The method of claim 1, wherein the polypeptide is capable of converting the substrate 3-keto-DON into the product 3-epi-DON, wherein between 79.0% and 96.0%, between 80.0% and 95.0%, or between 81.0% and 94.0% of the total product is 3-epi-DON.

5. The method of claim 1, wherein the polypeptide is capable of converting the substrate 3-keto-DON into the product 3-epi-DON and additionally into the product DON amounting to 100% of total product, wherein between 3.9% and 21.5%, between 4.0% and 21.0%, or between 5.0% and 19.0% of the total product is DON.

6. The method of claim 1, wherein the polypeptide is capable of converting the substrate 3-keto-DON into the products 3-epi-DON and DON with a ratio of between 24.5:1 to 3.7:1, 24:1 to 4:1, 20:1 to 4:1, 18:1 to 4:1, 19:1 to 5:1, or 18:1 to 6:1.

7. A method of reducing the content of DON in a composition comprising DON or of reducing the toxicity of a composition comprising DON by converting DON into 3-epi-DON, the method comprising a) contacting the composition with an enzyme capable of converting DON into 3-keto DON; and b) subsequently or concurrently contacting the composition with one or more polypeptide(s) comprising or consisting of SEQ ID NO: 1, or a sequence having a sequence identity of at least at least 72.0% to SEQ ID NO: 1; wherein the polypeptide comprises one or more of the following polypeptide sequences:

(i)

(SEQ ID NO. 31)

YRKLGNSG;

(ii)

(SEQ ID NO. 32)

LGTMTFG;

(iii)

(SEQ ID NO. 33)

$AGGNFX_1DTAX_2VYS$, wherein $X_1$ is I or L and $X_2$ is N or D;

(iv)

(SEQ ID NO. 34)

ETLRFLDD;

-continued (v)

(SEQ ID NO. 35)

$GKIX_3YYGFSN$, wherein $X_3$ is A or G;

(vi)

(SEQ ID NO. 36)

$RDIEHEX_4VPA$, wherein $X_4$ = I or V;

(vii)

(SEQ ID NO. 37)

GLLPWSPLGGGWL;

(viii)

(SEQ ID NO. 38)

GATRLGENP;

(ix)

(SEQ ID NO. 39)

AQVALAW;
and/or (x)

(SEQ ID NO. 40)

$PAVX_5SVILGART$, wherein $X_5$ = T or A.

8. The method of claim 1 wherein the polypeptide comprises at least 330 or at least 340 amino acids, with respect to SEQ ID NO: 1.

9. The method of claim 8 wherein the polypeptide comprises or consists of 341, 342, or 343 amino acids, with respect to SEQ ID NO: 1.

10. The method of claim 2 wherein the polypeptide comprises all of the polypeptide sequences (i)-(x).

11. A method of converting 3-keto-DON into 3-epi-DON, the method comprising contacting one or more polypeptide(s) with 3-keto DON, wherein the one or more polypeptide(s) comprise or consist of: (a) SEQ ID NO: 1, or (b) a sequence having a sequence identity of at least 72.0% to SEQ ID NO: 1, and at least 95.0% sequence identity to any one of SEQ ID NOs: 1-28.

12. The method of claim 11 wherein the one or more polypeptide(s) comprise or consist of: (b) a sequence having a sequence identity of at least 72.0% to SEQ ID NO: 1, and at least 97.0% sequence identity to any one of SEQ ID NOs: 1-28.

13. The method of claim 12 wherein the one or more polypeptide(s) comprise or consist of: (b) a sequence having a sequence identity of at least 72.0% to SEQ ID NO: 1, and at least 99.0% sequence identity to any one of SEQ ID NOs: 1-28.

14. The method of claim 13 wherein the one or more polypeptide(s) comprise or consist of any one of SEQ ID NOs: 1-28.

15. The method of claim 11, wherein the polypeptide comprises one or more of the following polypeptide sequences:

(i)

(SEQ ID NO. 31)

YRKLGNSG;

(ii)

(SEQ ID NO. 32)

LGTMTFG;

(iii)

(SEQ ID NO. 33)

$AGGNFX_1DTAX_2VYS$, wherein $X_1$ is I or L and $X_2$ is N or D;

-continued (iv)

(SEQ ID NO. 34)

ETLRFLDD;

(v)

(SEQ ID NO. 35)

GKIX$_3$YYGFSN, wherein X$_3$ is A or G;

(vi)

(SEQ ID NO. 36)

RDIEHEX$_4$VPA, wherein X$_4$ = I or V;

(vii)

(SEQ ID NO. 37)

GLLPWSPLGGGWL;

(viii)

(SEQ ID NO. 38)

GATRLGENP;

(ix)

(SEQ ID NO. 39)

AQVALAW;
and/or (x)

(SEQ ID NO. 40)

PAVX$_5$SVILGART, wherein X$_5$ = T or A.

16. The method of claim 15 wherein the polypeptide comprises all of the polypeptide sequences (i)-(x).

17. The method of claim 11 wherein the polypeptide comprises at least 330 or at least 340 amino acids, with respect to SEQ ID NO: 1.

18. The method of claim 17 wherein the polypeptide comprises or consists of 341, 342, or 343 amino acids, with respect to SEQ ID NO: 1.

* * * * *

SEQUENCE LISTING

```
<160> NUMBER OF SEQ ID NOS: 42

<210> SEQ ID NO 1
<211> LENGTH: 343
<212> TYPE: PRT
<213> ORGANISM: Artificial Sequence
<220> FEATURE:
<223> OTHER INFORMATION: polypeptide/enzyme

<400> SEQUENCE: 1

Met Asp Tyr Arg Lys Leu Gly Asn Ser Gly Ala Val Val Ser His Leu
1               5                   10                  15
```

-continued

```
Cys Leu Gly Thr Met Thr Phe Gly Lys Glu Ala Asp Glu Ala Thr Ser
            20                  25                  30

His Leu Leu Leu Asp Asp Tyr Val Ala Ala Gly Gly Asn Phe Ile Asp
        35                  40                  45

Thr Ala Asp Val Tyr Ser Thr Gly Val Ser Glu Thr Ile Ile Gly Asn
    50                  55                  60

Trp Leu Lys Ala Lys Pro Gly Arg Glu Leu Asn Leu Val Ile Ala Ser
65                  70                  75                  80

Lys Gly Arg Phe Pro Met Gly Asn Gly Pro Asn Asp Leu Gly Leu Ser
                85                  90                  95

Arg Lys His Leu Gly Ala Ala Leu Asp Ala Ser Leu Lys Arg Leu Gly
            100                 105                 110

Val Glu Arg Ile Asp Leu Tyr Gln Met His Ala Phe Asp Ala Leu Thr
        115                 120                 125

Pro Met Asp Glu Thr Leu Arg Phe Leu Asp Asp Ser Ile Arg Asn Gly
    130                 135                 140

Lys Ile Ala Tyr Tyr Gly Phe Ser Asn Phe Thr Gly Trp Gln Leu Thr
145                 150                 155                 160

Lys Ala Val Tyr Leu Ala Lys Leu Asn Gly Tyr Gln Pro Pro Val Thr
                165                 170                 175

Leu Gln Pro Gln Tyr Asn Leu Leu Val Arg Asp Ile Glu His Glu Ile
            180                 185                 190

Val Pro Ala Ser Leu Asp Ala Gln Ile Gly Leu Leu Pro Trp Ser Pro
        195                 200                 205

Leu Gly Gly Gly Trp Leu Ser Gly Lys Tyr Lys Arg Asp Gln Ala Pro
    210                 215                 220

Ser Gly Ala Thr Arg Leu Gly Glu Asn Pro Lys Arg Gly Met Glu Ala
225                 230                 235                 240

Phe Glu Ala Arg Asn Ala Lys Asp Ala Thr Trp Ser Ile Ile Gly Ala
                245                 250                 255

Val Glu Asp Ile Ala Lys Ala His Asn Val Ser Met Ala Gln Val Ala
            260                 265                 270

Leu Ala Trp Val Val Ala Gln Pro Ala Val Thr Ser Val Ile Leu Gly
        275                 280                 285

Ala Arg Thr Arg Glu Gln Leu Ala Asp Asn Leu Lys Ser Val Ser Leu
    290                 295                 300

Lys Leu Ser Ala Ala Asp Leu Ala Thr Leu Ser Glu Ala Ser Lys Pro
305                 310                 315                 320

Ala Met Ser Asp Tyr Pro Tyr Gly Ala Gly Gly Ile Asn Gln Arg His
                325                 330                 335

Arg Lys Leu Glu Gly Gly Arg
            340


<210> SEQ ID NO 2
<211> LENGTH: 343
<212> TYPE: PRT
<213> ORGANISM: Artificial Sequence
<220> FEATURE:
<223> OTHER INFORMATION: polypeptide/enzyme

<400> SEQUENCE: 2

Met Glu Tyr Arg Lys Leu Gly Asn Ser Gly Thr Ile Val Thr Ser Tyr
1               5                   10                  15

Cys Leu Gly Thr Met Thr Phe Gly Ala Glu Ala Asp Glu Thr Thr Ser
            20                  25                  30
```

-continued

```
His Leu Ile Leu Asp Asp Tyr Val Glu Ala Gly Gly Asn Phe Ile Asp
        35                  40                  45

Thr Ala Asn Val Tyr Ser Leu Gly Val Ser Glu Glu Ile Val Gly Arg
    50                  55                  60

Trp Leu Lys Ala Arg Pro Glu Ala Ala Ser Gln Val Val Leu Ala Thr
65                  70                  75                  80

Lys Gly Arg Phe Pro Met Gly Ala Gly Pro Asn Asp Ile Gly Leu Ser
                85                  90                  95

Arg Lys His Leu Asn Arg Ala Leu Glu Asp Ser Leu Arg Arg Leu Gly
            100                 105                 110

Val Glu Gln Ile Asp Leu Tyr Gln Met His Ala Trp Asp Ala Leu Thr
        115                 120                 125

Pro Ile Glu Glu Thr Leu Arg Phe Leu Asp Asp Ala Val Gly Ala Gly
    130                 135                 140

Lys Ile Ala Tyr Tyr Gly Phe Ser Asn Tyr Leu Gly Trp Gln Val Thr
145                 150                 155                 160

Lys Ala Val His Val Ala Lys Ala Asn His Trp Ser Ala Pro Val Thr
                165                 170                 175

Leu Gln Pro Gln Tyr Asn Leu Leu Val Arg Asp Ile Glu His Glu Ile
            180                 185                 190

Val Pro Ala Cys Leu Asp Ala Gly Met Gly Leu Leu Pro Trp Ser Pro
        195                 200                 205

Leu Gly Gly Gly Trp Leu Ala Gly Lys Tyr Gln Arg Asp Val Met Pro
    210                 215                 220

Ser Gly Ala Thr Arg Leu Gly Glu Asn Pro Asn Arg Gly Met Glu Ser
225                 230                 235                 240

Phe Gly Pro Arg Asn Ala Gln Glu Arg Thr Trp Gln Ile Ile Asp Ala
                245                 250                 255

Val Ala Glu Ile Ala Lys Asp Arg Gly Ala Ser Ala Ala Gln Val Ala
            260                 265                 270

Leu Ala Trp Val Glu Ala Arg Pro Ala Val Thr Ser Val Ile Leu Gly
        275                 280                 285

Ala Arg Thr Arg Glu Gln Leu Ala Asp Asn Leu Gly Ser Ser Lys Val
    290                 295                 300

Lys Leu Ser Ala Glu Glu Thr Asp Lys Leu Thr Arg Ile Ser Met Pro
305                 310                 315                 320

Gln Met Ser Asp Tyr Pro Tyr Gly Glu Arg Gly Val Ser Gln Arg Phe
                325                 330                 335

Arg Lys Met Glu Gly Gly Arg
            340


<210> SEQ ID NO 3
<211> LENGTH: 341
<212> TYPE: PRT
<213> ORGANISM: Artificial Sequence
<220> FEATURE:
<223> OTHER INFORMATION: polypeptide/enzyme

<400> SEQUENCE: 3

Met Asp Tyr Arg Lys Leu Gly Asn Ser Gly Ala Val Val Ser Asn Leu
1               5                   10                  15

Cys Leu Gly Thr Met Thr Phe Gly Asp Glu Ala Asp Glu Ala Thr Ser
            20                  25                  30

Phe Val Leu Met Asp Gln Tyr Val Glu Ala Gly Gly Asn Phe Leu Asp
        35                  40                  45
```

-continued

Thr Ala Asp Val Tyr Ser Ala Gly Leu Ser Glu Glu Ile Val Gly Arg
    50                  55                  60

Trp Leu Lys Gly Lys Lys Leu Arg Asp Leu Val Ile Ala Thr Lys Gly
65                  70                  75                  80

Arg Phe Pro Met Gly Gln Gly Pro Asn His Leu Gly Leu Ser Arg Lys
                85                  90                  95

His Leu Gly Glu Ala Leu Asp Ala Ser Leu Gln Arg Leu Gly Val Glu
            100                 105                 110

Gln Ile Asp Leu Tyr Gln Met His Ala Trp Asp Ala Leu Thr Pro Leu
        115                 120                 125

Glu Glu Thr Leu Arg Phe Leu Asp Asp Ala Val Arg Ser Gly Lys Ile
    130                 135                 140

Ala Tyr Tyr Gly Phe Ser Asn Phe Leu Gly Trp His Ile Thr Lys Ala
145                 150                 155                 160

Val Trp Met Ala Arg Ala Gln Gly Tyr Ala Ala Pro Val Thr Leu Gln
                165                 170                 175

Pro Gln Tyr Asn Leu Leu Val Arg Asp Ile Glu His Glu Val Val Pro
            180                 185                 190

Ala Cys Glu Asp Ala Gly Met Gly Leu Leu Pro Trp Ser Pro Leu Gly
        195                 200                 205

Gly Gly Trp Leu Ser Gly Lys Tyr Lys Arg Asp Gln Met Pro Glu Gly
    210                 215                 220

Ala Thr Arg Leu Gly Glu Asn Pro Lys Arg Gly Met Glu Ala Tyr Glu
225                 230                 235                 240

Gly Arg Asn Ala Gln Glu Arg Thr Trp Ala Ile Ile Gly Ala Val Glu
                245                 250                 255

Asp Ile Ala Lys Ala Gln Asp Val Thr Met Ala Gln Val Ala Leu Ala
            260                 265                 270

Trp Thr Ala Ala Arg Pro Ala Val Thr Ser Val Ile Leu Gly Ala Arg
        275                 280                 285

Thr Ala Glu Gln Leu Lys Asp Asn Leu Gly Ala Ala Asp Leu Val Leu
    290                 295                 300

Ser Glu Ala Asp Met Glu Arg Leu Asn Ala Val Ser Ala Pro Gln Met
305                 310                 315                 320

Ala Asp Tyr Pro Tyr Gly Thr Gly Gly Ile Gly Gln Arg Asn Arg Lys
                325                 330                 335

Ile Glu Gly Gly Arg
            340

<210> SEQ ID NO 4
<211> LENGTH: 343
<212> TYPE: PRT
<213> ORGANISM: Artificial Sequence
<220> FEATURE:
<223> OTHER INFORMATION: polypeptide/enzyme

<400> SEQUENCE: 4

Met Asp Tyr Arg Lys Leu Gly Asn Ser Gly Ala Val Val Ser His Leu
1               5                   10                  15

Cys Leu Gly Thr Met Thr Phe Gly Ser Glu Ala Asp Glu Ala Thr Ser
            20                  25                  30

Phe Lys Leu Leu Asp Asp Tyr Val Ala Ala Gly Gly Asn Phe Ile Asp
        35                  40                  45

Thr Ala Asp Val Tyr Ser Ala Gly Val Ser Glu Glu Ile Ile Gly Arg
    50                  55                  60

Trp Leu Lys Asp Lys Pro Gly Arg Ala Gln Asn Leu Val Ile Ala Thr
65 70 75 80

Lys Gly Arg Phe Pro Met Gly Gln Gly Pro Asn Asp Leu Gly Leu Ser
85 90 95

Arg Lys His Leu Gly Ala Ala Leu Asp Ala Ser Leu Lys Arg Leu Gly
100 105 110

Val Glu Gln Ile Asp Leu Tyr Gln Met His Ala Phe Asp Val Leu Thr
115 120 125

Pro Leu Glu Glu Thr Leu Arg Phe Leu Asp Asp Ser Ile Arg Asn Gly
130 135 140

Lys Ile Ala Tyr Tyr Gly Phe Ser Asn Phe Thr Gly Trp Gln Leu Thr
145 150 155 160

Lys Ala Val Trp Leu Ala Lys Leu Asn Gly Tyr Gln Pro Pro Val Thr
165 170 175

Leu Gln Pro Gln Tyr Ser Leu Leu Val Arg Asp Ile Glu His Glu Ile
180 185 190

Val Pro Ala Ser Leu Asp Ala Gly Ile Gly Leu Leu Pro Trp Ser Pro
195 200 205

Leu Gly Gly Gly Trp Leu Ser Gly Lys Tyr Lys Arg Asp Gln Met Pro
210 215 220

Thr Gly Ala Thr Arg Leu Gly Glu Asn Pro Lys Arg Gly Met Glu Ala
225 230 235 240

Phe Glu Ala Arg Asn Ala Lys Asp Ser Thr Trp Ala Val Ile Gly Ala
245 250 255

Val Glu Asp Ile Ala Lys Ala Arg Gly Val Ser Met Ala Gln Val Ala
260 265 270

Leu Ala Trp Val Ala Ala Gln Pro Ala Val Ala Ser Val Ile Leu Gly
275 280 285

Ala Arg Thr Gln Glu Gln Leu Ala Asp Asn Leu Lys Ser Ala Ala Leu
290 295 300

Lys Leu Ser Ala Gly Asp Leu Gln Thr Leu Gly Asp Val Ser Lys Pro
305 310 315 320

Val Met Ala Asp Tyr Pro Tyr Gly Thr Gly Gly Ile Asn Gln Arg Asn
325 330 335

Arg Asn Ile Glu Gly Gly Arg
340

<210> SEQ ID NO 5
<211> LENGTH: 343
<212> TYPE: PRT
<213> ORGANISM: Artificial Sequence
<220> FEATURE:
<223> OTHER INFORMATION: polypeptide/enzyme

<400> SEQUENCE: 5

Met Lys Tyr Arg Lys Leu Gly Asn Ser Gly Ala Val Val Ser Ala Tyr
1 5 10 15

Cys Leu Gly Thr Met Thr Phe Gly Ala Glu Ser Asp Glu Ala Thr Ser
20 25 30

Phe Arg Leu Met Asp Asp Tyr Val Ala Ala Gly Gly Asn Phe Leu Asp
35 40 45

Thr Ala Asn Val Tyr Ser Ala Gly Val Ser Glu Glu Ile Val Gly Arg
50 55 60

Trp Leu Lys Thr Lys Pro Thr Gly Leu Arg Asp Leu Val Ile Thr Thr
65 70 75 80

-continued

```
Lys Gly Arg Phe Pro Met Gly Asp Gly Pro Asn His Leu Gly Leu Ser
                85                  90                  95

Arg Lys Asn Leu Arg Glu Ala Leu Asp Ala Ser Leu Lys Arg Leu Gly
            100                 105                 110

Val Glu His Ile Asp Leu Tyr Gln Met His Ala Phe Asp Ala Leu Thr
        115                 120                 125

Pro Leu Glu Glu Thr Leu Arg Phe Leu Asp Asp Ser Ile Arg Asn Gly
    130                 135                 140

Lys Ile Ala Tyr Tyr Gly Phe Ser Asn Phe Leu Gly Trp Gln Leu Thr
145                 150                 155                 160

Lys Ala Val Trp Ile Ala Arg Ala Asn Gly Tyr Gln Pro Pro Val Thr
                165                 170                 175

Leu Gln Pro Gln Tyr Asn Leu Leu Val Arg Asp Ile Glu His Glu Ile
            180                 185                 190

Val Pro Ala Ser Leu Asp Ala Gly Ile Gly Leu Leu Pro Trp Ser Pro
        195                 200                 205

Leu Gly Gly Gly Trp Leu Ser Gly Lys Tyr Arg Arg Asp Glu Met Pro
    210                 215                 220

Thr Gly Ala Thr Arg Leu Gly Glu Asn Pro Lys Arg Gly Gly Glu Ala
225                 230                 235                 240

Tyr Glu Arg Arg Asn Ala Lys Ser Ala Thr Trp Asp Ile Ile Gly Val
                245                 250                 255

Val Glu Asp Val Ala Lys Thr Arg Gly Val Ser Met Ala Gln Val Ala
            260                 265                 270

Leu Ala Trp Val Ala Gln Arg Pro Ala Val Thr Ser Val Ile Leu Gly
        275                 280                 285

Ala Arg Thr Thr Glu Gln Leu Lys Asp Asn Leu Gly Ala Ile Asp Leu
    290                 295                 300

Ala Leu Ser Thr Glu Glu Ile Glu Lys Leu Asn Ala Ala Ser Lys Pro
305                 310                 315                 320

Ala Val Gly Asp Tyr Pro Tyr Gly Ala Gly Gly Ile Asn Gln Arg Asn
                325                 330                 335

Arg Lys Ile Glu Gly Gly Arg
            340


<210> SEQ ID NO 6
<211> LENGTH: 343
<212> TYPE: PRT
<213> ORGANISM: Artificial Sequence
<220> FEATURE:
<223> OTHER INFORMATION: polypeptide/enzyme

<400> SEQUENCE: 6

Met Gln Tyr Arg Lys Leu Gly Asn Ser Gly Ala Val Val Ser Thr Gln
1               5                   10                  15

Thr Leu Gly Thr Met Thr Phe Gly Ala Glu Ala Asp Glu Ala Thr Ser
            20                  25                  30

Phe Gln Leu Met Asp Asp Tyr Val Ala Ala Gly Gly Asn Phe Leu Asp
        35                  40                  45

Thr Ala Asp Val Tyr Ser Ala Gly Thr Ser Glu Glu Ile Val Gly Arg
    50                  55                  60

Trp Leu Lys Ala Arg Pro Glu Ala Ala Arg Gln Val Leu Ile Thr Thr
65                  70                  75                  80

Lys Ala Arg Phe Pro Met Gly Ser Gly Pro Asn Asp Leu Gly Leu Ser
                85                  90                  95
```

-continued

```
Arg Arg His Leu Asn Gln Ala Leu Asp Ala Ser Leu Gly Arg Leu Gly
            100                 105                 110

Val Glu His Ile Asp Leu Tyr Gln Met His Ala Phe Asp Ala Leu Thr
        115                 120                 125

Pro Leu Glu Glu Thr Leu Arg Phe Leu Asp Asp Ala Ile Arg Asn Gly
    130                 135                 140

Lys Ile Gly Tyr Tyr Gly Phe Ser Asn Phe Ile Gly Trp Gln Leu Thr
145                 150                 155                 160

Lys Ala Thr Trp Ile Ala Lys Ala Gly Gly Leu Ala Pro Pro Ile Thr
                165                 170                 175

Leu Gln Pro His Tyr Asn Leu Leu Val Arg Asp Ile Glu His Glu Ile
            180                 185                 190

Val Pro Ala Ala Leu Asp Ala Asp Ile Gly Leu Leu Pro Trp Ser Pro
        195                 200                 205

Leu Gly Gly Gly Trp Leu Thr Gly Lys Tyr Lys Arg Asp Gln Leu Pro
    210                 215                 220

Thr Gly Ala Thr Arg Leu Gly Glu Asn Pro Asn Arg Gly Gln Glu Ser
225                 230                 235                 240

Tyr Gly Pro Arg Asn Glu Gln Glu Arg Thr Trp Arg Ile Ile Ala Ala
                245                 250                 255

Val Glu Ala Val Ala Lys Ala Leu Gly Val Ser Met Ala Gln Val Ala
            260                 265                 270

Leu Ala Trp Leu Ala Asp Arg Pro Ala Val Thr Ser Val Ile Leu Gly
        275                 280                 285

Ala Arg Thr Arg Glu Gln Leu Ala Asp Asn Leu Ala Ala Ala Asp Leu
    290                 295                 300

Arg Leu Asp Ala Glu His Ala Gln Gln Leu Thr Asp Ala Ser Ala Pro
305                 310                 315                 320

Glu Val Ala Asp Tyr Pro Tyr Gly Lys Gly Gly Val Asn Gln Arg His
                325                 330                 335

Arg Lys Ile Ala Gly Gly Arg
            340


<210> SEQ ID NO 7
<211> LENGTH: 343
<212> TYPE: PRT
<213> ORGANISM: Artificial Sequence
<220> FEATURE:
<223> OTHER INFORMATION: polypeptide/enzyme

<400> SEQUENCE: 7

Met Glu Tyr Arg Lys Leu Gly Asn Ser Gly Ala Ile Val Thr Asn Tyr
1               5                   10                  15

Cys Leu Gly Thr Met Thr Phe Gly Lys Glu Ser Asp Glu Ala Thr Ser
            20                  25                  30

Phe Arg Leu Met Asp Asp Tyr Val Ala Ala Gly Gly Asn Phe Ile Asp
        35                  40                  45

Thr Ala Asn Val Tyr Ser Asp Gly Leu Ser Glu Gln Ile Ile Gly Gly
    50                  55                  60

Trp Leu Lys Ser Lys Pro Gly Ile Leu Arg Asp Leu Val Ile Thr Thr
65                  70                  75                  80

Lys Gly Arg Phe Pro Met Gly Asp Gly Pro Asn His Leu Gly Leu Ser
                85                  90                  95

Arg Lys Asn Leu Ser Glu Ala Leu Asp Ala Ser Leu Lys Arg Leu Gly
            100                 105                 110
```

-continued

```
Val Glu His Ile Asp Leu Tyr Gln Leu His Ala Phe Asp Ala Leu Thr
        115                 120                 125

Pro Ile Glu Glu Thr Leu Arg Phe Leu Asp Asp Ser Ile Arg Asn Gly
    130                 135                 140

Lys Ile Ala Tyr Tyr Gly Phe Ser Asn Phe Leu Gly Trp Gln Met Thr
145                 150                 155                 160

Lys Ala Val Trp Ile Ala Lys Ala Gly Asn Phe Gln Pro Pro Val Thr
                165                 170                 175

Leu Gln Pro Gln Tyr Asn Leu Leu Ala Arg Asp Ile Glu His Glu Val
            180                 185                 190

Val Pro Ala Ala Leu Asp Ala Gly Ile Gly Leu Leu Pro Trp Ser Pro
        195                 200                 205

Leu Gly Gly Gly Trp Leu Ser Gly Lys Tyr Lys Arg Asp Gln Met Pro
    210                 215                 220

Ser Gly Ala Thr Arg Leu Gly Glu Asn Pro Lys Arg Gly Leu Glu Ala
225                 230                 235                 240

Phe Glu Lys Arg Asn Ala Asn Pro Ala Thr Trp Gln Val Ile Gly Ala
                245                 250                 255

Leu Glu Asp Ile Ala Lys Ala Arg Gly Ala Ser Met Ala Gln Val Ala
            260                 265                 270

Leu Ala Trp Leu Val Lys Arg Pro Ala Val Thr Ser Val Ile Leu Gly
        275                 280                 285

Ala Arg Thr Ala Glu Gln Leu Ala Asp Asn Leu Gly Ala Ala Asp Val
    290                 295                 300

Thr Leu Ser Asp Asp Glu Met Arg Thr Leu Thr Glu Met Ser Ala Pro
305                 310                 315                 320

Gln Val Ala Asp Tyr Pro Tyr Gly Glu Gly Gly Asn Arg Gln Arg Asn
                325                 330                 335

Arg Arg Met Glu Gly Gly Arg
            340


<210> SEQ ID NO 8
<211> LENGTH: 343
<212> TYPE: PRT
<213> ORGANISM: Artificial Sequence
<220> FEATURE:
<223> OTHER INFORMATION: polypeptide/enzyme

<400> SEQUENCE: 8

Met Asp Tyr Arg Lys Leu Gly Asn Ser Gly Ala Val Val Ser Ser Tyr
1               5                   10                  15

Cys Leu Gly Thr Met Thr Phe Gly Ala Glu Ala Asp Glu Ala Thr Ser
            20                  25                  30

His Leu Leu Leu Asp Asp Tyr Val Glu Ala Gly Gly Asn Phe Ile Asp
        35                  40                  45

Thr Ala Asn Val Tyr Ser Leu Gly Val Ser Glu Glu Ile Ile Gly Arg
    50                  55                  60

Trp Leu Lys Ala Lys Pro Glu Ala Ala Ser Asn Leu Val Ile Ala Ser
65                  70                  75                  80

Lys Gly Arg Phe Pro Met Gly Ala Gly Pro Asn Asp Leu Gly Leu Ser
                85                  90                  95

Arg Lys His Leu Asn Arg Ala Leu Asp Asp Ser Leu Lys Arg Leu Gly
            100                 105                 110

Val Glu Gln Ile Asp Leu Tyr Gln Met His Ala Trp Asp Ala Leu Thr
        115                 120                 125
```

```
Pro Ile Glu Glu Thr Leu Arg Phe Leu Asp Asp Ser Ile Gly Ala Gly
    130                 135                 140

Lys Ile Ala Tyr Tyr Gly Phe Ser Asn Tyr Leu Gly Trp Gln Val Thr
145                 150                 155                 160

Lys Ala Val His Val Ala Lys Ala Asn His Trp Ser Ala Pro Val Thr
                165                 170                 175

Leu Gln Pro Gln Tyr Asn Leu Leu Val Arg Asp Ile Glu His Glu Ile
            180                 185                 190

Val Pro Ala Cys Leu Asp Ala Gly Met Gly Leu Leu Pro Trp Ser Pro
        195                 200                 205

Leu Gly Gly Gly Trp Leu Ala Gly Lys Tyr Gln Arg Asp Val Met Pro
    210                 215                 220

Ser Gly Ala Thr Arg Leu Gly Glu Asn Pro Asn Arg Gly Met Glu Ser
225                 230                 235                 240

Phe Gly Pro Arg Asn Ala Gln Glu Arg Thr Trp Gln Ile Ile Asp Ala
                245                 250                 255

Val Ala Glu Ile Ala Lys Asp Arg Gly Ala Ser Ala Ala Gln Val Ala
            260                 265                 270

Leu Ala Trp Val Glu Ala Arg Pro Ala Val Thr Ser Val Ile Leu Gly
        275                 280                 285

Ala Arg Thr Arg Glu Gln Leu Ala Asp Asn Leu Gly Ser Ser Lys Val
    290                 295                 300

Lys Leu Ser Ala Glu Glu Thr Asp Lys Leu Thr Arg Ile Ser Met Pro
305                 310                 315                 320

Gln Met Ser Asp Tyr Pro Tyr Gly Glu Arg Gly Val Ser Gln Arg Phe
                325                 330                 335

Arg Lys Met Glu Gly Gly Arg
            340


<210> SEQ ID NO 9
<211> LENGTH: 343
<212> TYPE: PRT
<213> ORGANISM: Artificial Sequence
<220> FEATURE:
<223> OTHER INFORMATION: polypeptide/enzyme

<400> SEQUENCE: 9

Met Glu Tyr Arg Lys Leu Gly Asn Ser Gly Thr Ile Val Thr Ser Tyr
1               5                   10                  15

Cys Leu Gly Thr Met Thr Phe Gly Ala Glu Ala Asp Glu Thr Thr Ser
            20                  25                  30

His Leu Ile Leu Asp Asp Tyr Val Glu Ala Gly Gly Asn Phe Ile Asp
        35                  40                  45

Thr Ala Asn Val Tyr Ser Leu Gly Val Ser Glu Glu Ile Val Gly Arg
    50                  55                  60

Trp Leu Lys Ala Arg Pro Glu Ala Ala Ser Gln Val Val Leu Ala Ser
65                  70                  75                  80

Lys Gly Arg Phe Pro Met Gly Ala Gly Pro Asn Asp Leu Gly Leu Ser
                85                  90                  95

Arg Lys His Leu Asn Arg Ala Leu Asp Asp Ser Leu Lys Arg Leu Gly
            100                 105                 110

Val Glu Gln Ile Asp Leu Tyr Gln Met His Ala Trp Asp Ala Leu Thr
        115                 120                 125

Pro Ile Glu Glu Thr Leu Arg Phe Leu Asp Asp Ser Ile Gly Ala Gly
    130                 135                 140
```

Lys Ile Ala Tyr Tyr Gly Phe Ser Asn Tyr Leu Gly Trp Gln Leu Thr
145 150 155 160

Lys Ala Val His Leu Ala Lys Leu Asn His Trp Ser Ala Pro Val Thr
165 170 175

Leu Gln Pro Gln Tyr Asn Leu Leu Val Arg Asp Ile Glu His Glu Ile
180 185 190

Val Pro Ala Cys Leu Asp Ala Gly Met Gly Leu Leu Pro Trp Ser Pro
195 200 205

Leu Gly Gly Gly Trp Leu Ala Gly Lys Tyr Gln Arg Asp Val Met Pro
210 215 220

Ser Gly Ala Thr Arg Leu Gly Glu Asn Pro Asn Arg Gly Met Glu Ser
225 230 235 240

Phe Gly Pro Arg Asn Ala Gln Asp Arg Thr Trp Gln Ile Ile Asp Ala
245 250 255

Val Ala Asp Ile Ala Lys Asp Arg Gly Val Ser Ala Ala Gln Val Ala
260 265 270

Leu Ala Trp Val Glu Ala Arg Pro Ala Val Thr Ser Val Ile Leu Gly
275 280 285

Ala Arg Thr Arg Glu Gln Leu Ala Asp Asn Leu Gly Ser Ser Lys Leu
290 295 300

Lys Leu Ser Ala Glu Asp Thr Asp Lys Leu Ser Arg Ala Ser Met Pro
305 310 315 320

Gln Met Ser Asp Tyr Pro Tyr Gly Glu Arg Gly Ile Ser Gln Arg Phe
325 330 335

Arg Lys Met Glu Gly Gly Arg
340

<210> SEQ ID NO 10
<211> LENGTH: 343
<212> TYPE: PRT
<213> ORGANISM: Artificial Sequence
<220> FEATURE:
<223> OTHER INFORMATION: polypeptide/enzyme

<400> SEQUENCE: 10

Met Glu Tyr Arg Lys Leu Gly Asn Ser Gly Thr Ile Val Thr Ser Tyr
1 5 10 15

Cys Leu Gly Thr Met Thr Phe Gly Ala Glu Ala Asp Glu Thr Thr Ser
20 25 30

His Leu Leu Leu Asp Asp Tyr Val Glu Ala Gly Gly Asn Phe Ile Asp
35 40 45

Thr Ala Asn Val Tyr Ser Leu Gly Val Ser Glu Glu Ile Ile Gly Arg
50 55 60

Trp Leu Lys Ala Lys Pro Glu Ala Ala Ser Gln Val Val Ile Ala Ser
65 70 75 80

Lys Gly Arg Phe Pro Met Gly Ala Gly Pro Asn Asp Leu Gly Leu Ser
85 90 95

Arg Lys His Leu Asn Arg Ala Leu Asp Asp Ser Leu Arg Arg Leu Gly
100 105 110

Val Glu Gln Ile Asp Leu Tyr Gln Met His Ala Trp Asp Ala Leu Thr
115 120 125

Pro Ile Glu Glu Thr Leu Arg Phe Leu Asp Asp Ser Ile Gly Ala Gly
130 135 140

Lys Ile Ala Tyr Tyr Gly Phe Ser Asn Tyr Leu Gly Trp Gln Leu Thr
145 150 155 160

-continued

```
Lys Ala Val His Leu Ala Lys Leu Asn His Trp Ser Ala Pro Val Thr
                165                 170                 175

Leu Gln Pro Gln Tyr Asn Leu Leu Val Arg Asp Ile Glu His Glu Ile
            180                 185                 190

Val Pro Ala Cys Leu Asp Ala Gly Met Gly Leu Leu Pro Trp Ser Pro
        195                 200                 205

Leu Gly Gly Gly Trp Leu Ser Gly Lys Tyr Gln Arg Asp Val Met Pro
    210                 215                 220

Ser Gly Ala Thr Arg Leu Gly Glu Asn Pro Asn Arg Gly Met Glu Ser
225                 230                 235                 240

Phe Gly Pro Arg Asn Ala Gln Glu Arg Thr Trp Gln Ile Ile Asp Ala
                245                 250                 255

Val Ala Glu Ile Ala Lys Asp Arg Gly Ala Ser Ala Ala Gln Val Ala
            260                 265                 270

Leu Ala Trp Val Glu Ala Arg Pro Ala Val Thr Ser Val Ile Leu Gly
        275                 280                 285

Ala Arg Thr Arg Glu Gln Leu Ala Asp Asn Leu Gly Ser Ser Lys Val
    290                 295                 300

Lys Leu Ser Ala Glu Glu Thr Asp Lys Leu Thr Arg Ile Ser Met Pro
305                 310                 315                 320

Gln Met Ser Asp Tyr Pro Tyr Gly Glu Arg Gly Val Ser Gln Arg Phe
                325                 330                 335

Arg Lys Met Glu Gly Gly Arg
            340


<210> SEQ ID NO 11
<211> LENGTH: 343
<212> TYPE: PRT
<213> ORGANISM: Artificial Sequence
<220> FEATURE:
<223> OTHER INFORMATION: polypeptide/enzyme

<400> SEQUENCE: 11

Met Glu Tyr Arg Lys Leu Gly Asn Ser Gly Thr Ile Val Ser Ser Tyr
1               5                   10                  15

Cys Leu Gly Thr Met Thr Phe Gly Ala Glu Ala Asp Glu Ala Thr Ser
            20                  25                  30

His Leu Ile Leu Asp Asp Tyr Val Glu Ala Gly Gly Asn Phe Ile Asp
        35                  40                  45

Thr Ala Asn Val Tyr Ser Leu Gly Val Ser Glu Glu Ile Ile Gly Arg
    50                  55                  60

Trp Leu Lys Ala Arg Pro Glu Ala Ala Ser Asn Val Val Leu Ala Ser
65                  70                  75                  80

Lys Gly Arg Phe Pro Met Gly Ala Gly Pro Asn Asp Leu Gly Leu Ser
                85                  90                  95

Arg Lys His Leu Asn Arg Ala Leu Glu Asp Ser Leu Lys Arg Leu Gly
            100                 105                 110

Val Glu Gln Ile Asp Leu Tyr Gln Met His Ala Trp Asp Ala Leu Thr
        115                 120                 125

Pro Ile Glu Glu Thr Leu Arg Phe Leu Asp Asp Ala Val Gly Ala Gly
    130                 135                 140

Lys Ile Ala Tyr Tyr Gly Phe Ser Asn Tyr Leu Gly Trp Gln Leu Thr
145                 150                 155                 160

Lys Ala Val His Leu Ala Lys Ala Asn His Trp Ser Ala Pro Val Thr
                165                 170                 175
```

Leu Gln Pro Gln Tyr Asn Leu Leu Val Arg Asp Ile Glu His Glu Ile
180 185 190

Val Pro Ala Cys Leu Asp Ala Gly Met Gly Leu Leu Pro Trp Ser Pro
195 200 205

Leu Gly Gly Gly Trp Leu Ala Gly Lys Tyr Gln Arg Asp Val Met Pro
210 215 220

Ser Gly Ala Thr Arg Leu Gly Glu Asn Pro Asn Arg Gly Met Glu Ala
225 230 235 240

Phe Gly Pro Arg Asn Ala Gln Asp Arg Thr Trp Gln Ile Ile Asp Ala
245 250 255

Val Ala Asp Ile Ala Lys Asp Arg Gly Val Ser Ala Ala Gln Val Ala
260 265 270

Leu Ala Trp Val Glu Ala Arg Pro Ala Val Thr Ser Val Ile Leu Gly
275 280 285

Ala Arg Thr Arg Glu Gln Leu Ala Asp Asn Leu Gly Ser Ser Lys Leu
290 295 300

Lys Leu Ser Ala Glu Asp Thr Asp Lys Leu Ser Arg Ile Ser Met Pro
305 310 315 320

Gln Met Ser Asp Tyr Pro Tyr Gly Glu Arg Gly Ile Ser Gln Arg Phe
325 330 335

Arg Lys Met Glu Gly Gly Arg
340

<210> SEQ ID NO 12
<211> LENGTH: 343
<212> TYPE: PRT
<213> ORGANISM: Artificial Sequence
<220> FEATURE:
<223> OTHER INFORMATION: polypeptide/sequence

<400> SEQUENCE: 12

Met Glu Tyr Arg Lys Leu Gly Asn Ser Gly Thr Ile Val Thr Ser Tyr
1 5 10 15

Cys Leu Gly Thr Met Thr Phe Gly Ala Glu Ala Asp Glu Thr Thr Ser
20 25 30

His Leu Ile Leu Asp Asp Tyr Val Glu Ala Gly Gly Asn Phe Ile Asp
35 40 45

Thr Ala Asn Val Tyr Ser Leu Gly Val Ser Glu Glu Ile Ile Gly Arg
50 55 60

Trp Leu Lys Ala Lys Pro Glu Ala Ala Ser Asn Leu Val Ile Ala Ser
65 70 75 80

Lys Gly Arg Phe Pro Met Gly Ala Gly Pro Asn Asp Leu Gly Leu Ser
85 90 95

Arg Lys His Leu Asn Arg Ala Leu Asp Asp Ser Leu Lys Arg Leu Gly
100 105 110

Val Glu Gln Ile Asp Leu Tyr Gln Met His Ala Trp Asp Ala Leu Thr
115 120 125

Pro Ile Glu Glu Thr Leu Arg Phe Leu Asp Asp Ala Val Gly Ala Gly
130 135 140

Lys Ile Ala Tyr Tyr Gly Phe Ser Asn Tyr Leu Gly Trp Gln Leu Thr
145 150 155 160

Lys Ala Val His Leu Ala Lys Leu Asn His Trp Ser Ala Pro Val Thr
165 170 175

Leu Gln Pro Gln Tyr Asn Leu Leu Val Arg Asp Ile Glu His Glu Ile
180 185 190

```
Val Pro Ala Cys Leu Asp Ala Gly Met Gly Leu Leu Pro Trp Ser Pro
        195                 200                 205

Leu Gly Gly Gly Trp Leu Ala Gly Lys Tyr Gln Arg Asp Val Met Pro
    210                 215                 220

Ser Gly Ala Thr Arg Leu Gly Glu Asn Pro Asn Arg Gly Met Glu Ser
225                 230                 235                 240

Phe Gly Pro Arg Asn Ala Gln Asp Arg Thr Trp Gln Ile Ile Asp Ala
                245                 250                 255

Val Ala Asp Ile Ala Lys Asp Arg Gly Val Ser Ala Ala Gln Val Ala
            260                 265                 270

Leu Ala Trp Val Glu Ala Arg Pro Ala Val Thr Ser Val Ile Leu Gly
        275                 280                 285

Ala Arg Thr Arg Glu Gln Leu Ala Asp Asn Leu Gly Ser Ser Lys Val
    290                 295                 300

Lys Leu Ser Ala Glu Glu Thr Asp Lys Leu Thr Arg Ile Ser Met Pro
305                 310                 315                 320

Gln Met Ser Asp Tyr Pro Tyr Gly Glu Arg Gly Val Ser Gln Arg Phe
                325                 330                 335

Arg Lys Met Glu Gly Gly Arg
            340


<210> SEQ ID NO 13
<211> LENGTH: 343
<212> TYPE: PRT
<213> ORGANISM: Artificial Sequence
<220> FEATURE:
<223> OTHER INFORMATION: polypeptide/enzyme

<400> SEQUENCE: 13

Met Asp Tyr Arg Lys Leu Gly Asn Ser Gly Thr Val Val Thr Ser Tyr
1               5                   10                  15

Cys Leu Gly Thr Met Thr Phe Gly Ala Glu Ala Asp Glu Ala Thr Ser
            20                  25                  30

His Leu Ile Leu Asp Asp Tyr Val Glu Ala Gly Gly Asn Phe Ile Asp
        35                  40                  45

Thr Ala Asn Val Tyr Ser Leu Gly Val Ser Glu Glu Ile Ile Gly Arg
    50                  55                  60

Trp Leu Lys Ala Arg Pro Glu Ala Ala Ser Asn Val Val Ile Ala Thr
65                  70                  75                  80

Lys Gly Arg Phe Pro Met Gly Ala Gly Pro Asn Asp Leu Gly Leu Ser
                85                  90                  95

Arg Lys His Leu Asn Arg Ala Leu Glu Asp Ser Leu Lys Arg Leu Gly
            100                 105                 110

Val Glu Gln Ile Asp Leu Tyr Gln Met His Ala Trp Asp Ala Leu Thr
        115                 120                 125

Pro Ile Glu Glu Thr Leu Arg Phe Leu Asp Asp Ala Ile Gly Ala Gly
    130                 135                 140

Lys Ile Ala Tyr Tyr Gly Phe Ser Asn Tyr Leu Gly Trp Gln Val Thr
145                 150                 155                 160

Lys Ala Val His Leu Ala Lys Ala Asn His Trp Ser Ala Pro Val Thr
                165                 170                 175

Leu Gln Pro Gln Tyr Asn Leu Leu Val Arg Asp Ile Glu His Glu Ile
            180                 185                 190

Val Pro Ala Cys Leu Asp Ala Gly Met Gly Leu Leu Pro Trp Ser Pro
        195                 200                 205
```

-continued

```
Leu Gly Gly Gly Trp Leu Ser Gly Lys Tyr Gln Arg Asp Val Met Pro
    210                 215                 220

Ser Gly Ala Thr Arg Leu Gly Glu Asn Pro Asn Arg Gly Met Glu Ala
225                 230                 235                 240

Phe Gly Pro Arg Asn Ala Gln Asp Arg Thr Trp Gln Ile Ile Asp Ala
                245                 250                 255

Val Ala Glu Ile Ala Lys Asp Arg Gly Val Ser Ala Ala Gln Val Ala
            260                 265                 270

Leu Ala Trp Val Glu Ala Arg Pro Ala Val Thr Ser Val Ile Leu Gly
        275                 280                 285

Ala Arg Thr Arg Glu Gln Leu Ala Asp Asn Leu Gly Ser Ser Lys Val
    290                 295                 300

Lys Leu Ser Ala Glu Asp Thr Asp Lys Leu Thr Arg Ala Ser Met Pro
305                 310                 315                 320

Gln Met Ser Asp Tyr Pro Tyr Gly Glu Arg Gly Val Ser Gln Arg Phe
                325                 330                 335

Arg Lys Met Glu Gly Gly Arg
            340


<210> SEQ ID NO 14
<211> LENGTH: 343
<212> TYPE: PRT
<213> ORGANISM: Artificial Sequence
<220> FEATURE:
<223> OTHER INFORMATION: polypeptide/enzyme

<400> SEQUENCE: 14

Met Glu Tyr Arg Lys Leu Gly Asn Ser Gly Ala Ile Val Thr Ser Tyr
1               5                   10                  15

Cys Leu Gly Thr Met Thr Phe Gly Ala Glu Ala Asp Glu Thr Thr Ser
            20                  25                  30

His Leu Leu Leu Asp Asp Tyr Val Glu Ala Gly Gly Asn Phe Ile Asp
        35                  40                  45

Thr Ala Asn Val Tyr Ser Leu Gly Val Ser Glu Glu Ile Ile Gly Arg
    50                  55                  60

Trp Leu Lys Ala Arg Pro Glu Ala Ala Ser Asn Val Val Leu Ala Thr
65                  70                  75                  80

Lys Gly Arg Phe Pro Met Gly Ala Gly Pro Asn Asp Leu Gly Leu Ser
                85                  90                  95

Arg Lys His Leu Asn Arg Ala Leu Glu Asp Ser Leu Lys Arg Leu Gly
            100                 105                 110

Val Glu Gln Ile Asp Leu Tyr Gln Met His Ala Trp Asp Ala Leu Thr
        115                 120                 125

Pro Ile Glu Glu Thr Leu Arg Phe Leu Asp Asp Ser Val Gly Ala Gly
    130                 135                 140

Lys Ile Ala Tyr Tyr Gly Phe Ser Asn Tyr Leu Gly Trp Gln Val Thr
145                 150                 155                 160

Lys Ala Val His Leu Ala Lys Ala Asn His Trp Ser Ala Pro Val Thr
                165                 170                 175

Leu Gln Pro Gln Tyr Asn Leu Leu Val Arg Asp Ile Glu His Glu Ile
            180                 185                 190

Val Pro Ala Cys Leu Asp Ala Gly Met Gly Leu Leu Pro Trp Ser Pro
        195                 200                 205

Leu Gly Gly Gly Trp Leu Ser Gly Lys Tyr Gln Arg Asp Val Met Pro
    210                 215                 220
```

```
Ser Gly Ala Thr Arg Leu Gly Glu Asn Pro Asn Arg Gly Met Glu Ala
225                 230                 235                 240

Phe Gly Pro Arg Asn Ala Gln Asp Arg Thr Trp Gln Ile Ile Asp Ala
                245                 250                 255

Val Ala Glu Ile Ala Lys Asp Arg Gly Val Ser Ala Ala Gln Val Ala
            260                 265                 270

Leu Ala Trp Val Glu Ala Arg Pro Ala Val Thr Ser Val Ile Leu Gly
        275                 280                 285

Ala Arg Thr Arg Glu Gln Leu Ala Asp Asn Leu Gly Ser Ser Lys Val
    290                 295                 300

Lys Leu Ser Ala Glu Asp Thr Asp Lys Leu Thr Arg Ala Ser Met Pro
305                 310                 315                 320

Gln Met Ser Asp Tyr Pro Tyr Gly Glu Arg Gly Val Ser Gln Arg Phe
                325                 330                 335

Arg Lys Met Glu Gly Gly Arg
            340


<210> SEQ ID NO 15
<211> LENGTH: 343
<212> TYPE: PRT
<213> ORGANISM: Artificial Sequence
<220> FEATURE:
<223> OTHER INFORMATION: polypeptide/enzyme

<400> SEQUENCE: 15

Met Asp Tyr Arg Lys Leu Gly Asn Ser Gly Ala Val Val Ser Ser Tyr
1               5                   10                  15

Cys Leu Gly Thr Met Thr Phe Gly Ala Glu Ala Asp Glu Ala Thr Ser
            20                  25                  30

His Leu Leu Leu Asp Asp Tyr Val Glu Ala Gly Gly Asn Phe Ile Asp
        35                  40                  45

Thr Ala Asn Val Tyr Ser Leu Gly Val Ser Glu Glu Ile Val Gly Arg
    50                  55                  60

Trp Leu Lys Ala Arg Pro Glu Ala Ala Ser Gln Val Val Leu Ala Thr
65                  70                  75                  80

Lys Gly Arg Phe Pro Met Gly Ala Gly Pro Asn Asp Ile Gly Leu Ser
                85                  90                  95

Arg Lys His Leu Asn Arg Ala Leu Glu Asp Ser Leu Arg Arg Leu Gly
            100                 105                 110

Val Glu Gln Ile Asp Leu Tyr Gln Met His Ala Trp Asp Ala Leu Thr
        115                 120                 125

Pro Ile Glu Glu Thr Leu Arg Phe Leu Asp Asp Ser Ile Gly Ala Gly
    130                 135                 140

Lys Ile Ala Tyr Tyr Gly Phe Ser Asn Tyr Leu Gly Trp Gln Leu Thr
145                 150                 155                 160

Lys Ala Val His Leu Ala Lys Leu Asn His Trp Ser Ala Pro Val Thr
                165                 170                 175

Leu Gln Pro Gln Tyr Asn Leu Leu Val Arg Asp Ile Glu His Glu Ile
            180                 185                 190

Val Pro Ala Cys Leu Asp Ala Gly Met Gly Leu Leu Pro Trp Ser Pro
        195                 200                 205

Leu Gly Gly Gly Trp Leu Ser Gly Lys Tyr Gln Arg Asp Val Met Pro
    210                 215                 220

Ser Gly Ala Thr Arg Leu Gly Glu Asn Pro Asn Arg Gly Met Glu Ser
225                 230                 235                 240
```

-continued

Phe Gly Pro Arg Asn Ala Gln Glu Arg Thr Trp Gln Ile Ile Asp Ala
245 250 255

Val Ala Glu Ile Ala Lys Asp Arg Gly Ala Ser Ala Ala Gln Val Ala
260 265 270

Leu Ala Trp Val Glu Ala Arg Pro Ala Val Thr Ser Val Ile Leu Gly
275 280 285

Ala Arg Thr Arg Glu Gln Leu Ala Asp Asn Leu Gly Ser Ser Lys Ser
290 295 300

Lys Leu Ser Ala Glu Asp Thr Asp Lys Leu Thr Arg Ile Ser Met Pro
305 310 315 320

Gln Met Ser Asp Tyr Pro Tyr Gly Glu Arg Gly Ile Ser Gln Arg Phe
325 330 335

Arg Lys Met Glu Gly Gly Arg
340

<210> SEQ ID NO 16
<211> LENGTH: 343
<212> TYPE: PRT
<213> ORGANISM: Artificial Sequence
<220> FEATURE:
<223> OTHER INFORMATION: polypeptide/enzyme

<400> SEQUENCE: 16

Met Glu Tyr Arg Lys Leu Gly Asn Ser Gly Thr Ile Val Thr Ser Tyr
1 5 10 15

Cys Leu Gly Thr Met Thr Phe Gly Ala Glu Ala Asp Glu Thr Thr Ser
20 25 30

His Leu Ile Leu Asp Asp Tyr Val Glu Ala Gly Gly Asn Phe Ile Asp
35 40 45

Thr Ala Asn Val Tyr Ser Leu Gly Val Ser Glu Glu Ile Ile Gly Arg
50 55 60

Trp Leu Lys Ala Lys Pro Glu Ala Ala Ser Asn Leu Val Ile Ala Ser
65 70 75 80

Lys Gly Arg Phe Pro Met Gly Ala Gly Pro Asn Asp Leu Gly Leu Ser
85 90 95

Arg Lys His Leu Asn Arg Ala Leu Asp Asp Ser Leu Lys Arg Leu Gly
100 105 110

Val Glu Gln Ile Asp Leu Tyr Gln Met His Ala Trp Asp Ala Leu Thr
115 120 125

Pro Ile Glu Glu Thr Leu Arg Phe Leu Asp Asp Ala Val Gly Ala Gly
130 135 140

Lys Ile Ala Tyr Tyr Gly Phe Ser Asn Tyr Leu Gly Trp Gln Val Thr
145 150 155 160

Lys Ala Val His Val Ala Lys Ala Asn His Trp Ser Ala Pro Val Thr
165 170 175

Leu Gln Pro Gln Tyr Asn Leu Leu Val Arg Asp Ile Glu His Glu Ile
180 185 190

Val Pro Ala Cys Leu Asp Ala Gly Met Gly Leu Leu Pro Trp Ser Pro
195 200 205

Leu Gly Gly Gly Trp Leu Ala Gly Lys Tyr Gln Arg Asp Val Met Pro
210 215 220

Ser Gly Ala Thr Arg Leu Gly Glu Asn Pro Asn Arg Gly Met Glu Ala
225 230 235 240

Phe Gly Pro Arg Asn Ala Gln Asp Arg Thr Trp Gln Ile Ile Asp Ala
245 250 255

Val Ala Asp Ile Ala Lys Asp Arg Gly Val Ser Ala Ala Gln Val Ala
260 265 270

Leu Ala Trp Val Glu Ala Arg Pro Ala Val Thr Ser Val Ile Leu Gly
275 280 285

Ala Arg Thr Arg Glu Gln Leu Ala Asp Asn Leu Gly Ser Ser Lys Val
290 295 300

Lys Leu Ser Ala Glu Glu Thr Asp Lys Leu Thr Arg Ile Ser Met Pro
305 310 315 320

Gln Met Ser Asp Tyr Pro Tyr Gly Glu Arg Gly Val Ser Gln Arg Phe
325 330 335

Arg Lys Met Glu Gly Gly Arg
340

<210> SEQ ID NO 17
<211> LENGTH: 343
<212> TYPE: PRT
<213> ORGANISM: Artificial Sequence
<220> FEATURE:
<223> OTHER INFORMATION: polypeptide/enzyme

<400> SEQUENCE: 17

Met Asp Tyr Arg Lys Leu Gly Asn Ser Gly Thr Ile Val Thr Ser Tyr
1 5 10 15

Cys Leu Gly Thr Met Thr Phe Gly Ala Glu Ala Asp Glu Ala Thr Ser
20 25 30

His Leu Leu Leu Asp Asp Tyr Val Glu Ala Gly Gly Asn Phe Ile Asp
35 40 45

Thr Ala Asn Val Tyr Ser Leu Gly Val Ser Glu Glu Ile Ile Gly Arg
50 55 60

Trp Leu Lys Ala Lys Pro Glu Ala Ala Ser Asn Leu Val Ile Ala Ser
65 70 75 80

Lys Gly Arg Phe Pro Met Gly Ala Gly Pro Asn Asp Leu Gly Leu Ser
85 90 95

Arg Lys His Leu Asn Arg Ala Leu Asp Asp Ser Leu Lys Arg Leu Gly
100 105 110

Val Glu Gln Ile Asp Leu Tyr Gln Met His Ala Trp Asp Ala Leu Thr
115 120 125

Pro Ile Glu Glu Thr Leu Arg Phe Leu Asp Asp Ala Val Gly Ala Gly
130 135 140

Lys Ile Ala Tyr Tyr Gly Phe Ser Asn Tyr Leu Gly Trp Gln Val Thr
145 150 155 160

Lys Ala Val His Val Ala Lys Ala Asn His Trp Ser Ala Pro Val Thr
165 170 175

Leu Gln Pro Gln Tyr Asn Leu Leu Val Arg Asp Ile Glu His Glu Ile
180 185 190

Val Pro Ala Cys Leu Asp Ala Gly Met Gly Leu Leu Pro Trp Ser Pro
195 200 205

Leu Gly Gly Gly Trp Leu Ser Gly Lys Tyr Gln Arg Asp Val Met Pro
210 215 220

Ser Gly Ala Thr Arg Leu Gly Glu Asn Pro Asn Arg Gly Met Glu Ser
225 230 235 240

Phe Gly Pro Arg Asn Ala Gln Asp Arg Thr Trp Gln Ile Ile Asp Ala
245 250 255

Val Ala Glu Ile Ala Lys Asp Arg Gly Val Ser Ala Ala Gln Val Ala
260 265 270

Leu Ala Trp Val Glu Ala Arg Pro Ala Val Thr Ser Val Ile Leu Gly
275 280 285

Ala Arg Thr Arg Glu Gln Leu Ala Asp Asn Leu Gly Ser Ser Lys Leu
290 295 300

Lys Leu Ser Ala Glu Glu Thr Asp Lys Leu Thr Arg Ile Ser Met Pro
305 310 315 320

Gln Met Ser Asp Tyr Pro Tyr Gly Glu Arg Gly Val Ser Gln Arg Phe
325 330 335

Arg Lys Met Glu Gly Gly Arg
340

<210> SEQ ID NO 18
<211> LENGTH: 343
<212> TYPE: PRT
<213> ORGANISM: Artificial Sequence
<220> FEATURE:
<223> OTHER INFORMATION: polypeptide/enzyme

<400> SEQUENCE: 18

Met Glu Tyr Arg Lys Leu Gly Asn Ser Gly Thr Ile Val Thr Ser Tyr
1 5 10 15

Cys Leu Gly Thr Met Thr Phe Gly Ala Glu Ala Asp Glu Ala Thr Ser
20 25 30

His Leu Leu Leu Asp Asp Tyr Val Glu Ala Gly Gly Asn Phe Ile Asp
35 40 45

Thr Ala Asn Val Tyr Ser Leu Gly Leu Ser Glu Gln Ile Ile Gly Arg
50 55 60

Trp Leu Lys Ala Lys Pro Glu Ala Ala Ser Gln Val Val Ile Ala Ser
65 70 75 80

Lys Gly Arg Phe Pro Met Gly Ala Gly Pro Asn Asp Leu Gly Leu Ser
85 90 95

Arg Lys His Leu Asn Arg Ala Leu Asp Asp Ser Leu Lys Arg Leu Gly
100 105 110

Val Glu Gln Ile Asp Leu Tyr Gln Met His Ala Trp Asp Ala Leu Thr
115 120 125

Pro Ile Glu Glu Thr Leu Arg Phe Leu Asp Asp Ala Val Gly Ala Gly
130 135 140

Lys Ile Ala Tyr Tyr Gly Phe Ser Asn Tyr Leu Gly Trp Gln Leu Thr
145 150 155 160

Lys Ala Val His Val Ala Lys Ala Asn His Trp Ser Ala Pro Val Thr
165 170 175

Leu Gln Pro Gln Tyr Asn Leu Leu Ala Arg Asp Ile Glu His Glu Ile
180 185 190

Val Pro Ala Cys Leu Asp Ala Gly Met Gly Leu Leu Pro Trp Ser Pro
195 200 205

Leu Gly Gly Gly Trp Leu Ala Gly Lys Tyr Gln Arg Asp Val Met Pro
210 215 220

Thr Gly Ala Thr Arg Leu Gly Glu Asn Pro Asn Arg Gly Met Glu Ala
225 230 235 240

Phe Gly Pro Arg Asn Ala Gln Glu Arg Thr Trp Gln Ile Ile Asp Ala
245 250 255

Val Ala Glu Ile Ala Lys Asp Arg Gly Ala Ser Ala Ala Gln Val Ala
260 265 270

Leu Ala Trp Val Glu Ala Arg Pro Ala Val Thr Ser Val Ile Leu Gly
275 280 285

```
Ala Arg Thr Arg Glu Gln Leu Ala Asp Asn Leu Gly Ser Val Lys Val
    290                 295                 300

Lys Leu Ser Ala Glu Glu Thr Asp Lys Leu Thr Arg Ile Ser Met Pro
305                 310                 315                 320

Gln Met Ser Asp Tyr Pro Tyr Gly Glu Arg Gly Val Ser Gln Arg Phe
                325                 330                 335

Arg Arg Met Glu Gly Gly Arg
            340
```

<210> SEQ ID NO 19
<211> LENGTH: 341
<212> TYPE: PRT
<213> ORGANISM: Artificial Sequence
<220> FEATURE:
<223> OTHER INFORMATION: polypeptide/enzyme

<400> SEQUENCE: 19

```
Met Asp Tyr Arg Lys Leu Gly Asn Ser Gly Ala Val Val Ser Asn Leu
1               5                   10                  15

Cys Leu Gly Thr Met Thr Phe Gly Asp Glu Ala Asp Glu Ala Thr Ser
            20                  25                  30

Phe Leu Leu Met Asp Gln Tyr Val Glu Ala Gly Gly Asn Phe Leu Asp
        35                  40                  45

Thr Ala Asp Val Tyr Ser Thr Gly Val Ser Glu Glu Ile Ile Gly Arg
    50                  55                  60

Trp Leu Lys Ala Lys Arg Leu Arg Asn Leu Val Ile Ala Ser Lys Gly
65                  70                  75                  80

Arg Phe Pro Met Gly Asn Gly Pro Asn His Leu Gly Leu Ser Arg Lys
                85                  90                  95

His Leu Gly Glu Ala Leu Asp Ala Ser Leu Gln Arg Leu Gly Val Glu
            100                 105                 110

Gln Ile Asp Leu Tyr Gln Met His Ala Trp Asp Ala Leu Thr Pro Leu
        115                 120                 125

Glu Glu Thr Leu Arg Phe Leu Asp Asp Ser Ile Arg Ser Gly Lys Ile
    130                 135                 140

Ala Tyr Tyr Gly Phe Ser Asn Phe Leu Gly Trp His Leu Thr Lys Ala
145                 150                 155                 160

Val Trp Met Ala Lys Leu Asn Gly Tyr Ala Ala Pro Val Thr Leu Gln
                165                 170                 175

Pro Gln Tyr Asn Leu Leu Val Arg Asp Ile Glu His Glu Val Val Pro
            180                 185                 190

Ala Cys Glu Asp Ala Gly Met Gly Leu Leu Pro Trp Ser Pro Leu Gly
        195                 200                 205

Gly Gly Trp Leu Ser Gly Lys Tyr Lys Arg Asp Gln Met Pro Glu Gly
    210                 215                 220

Ala Thr Arg Leu Gly Glu Asn Pro Lys Arg Gly Met Glu Ala Tyr Glu
225                 230                 235                 240

Gly Arg Asn Ala Gln Asp Arg Thr Trp Ser Ile Ile Gly Ala Val Glu
                245                 250                 255

Asp Ile Ala Lys Ala Gln Asp Val Thr Met Ala Gln Val Ala Leu Ala
            260                 265                 270

Trp Thr Ala Ala Arg Pro Ala Val Thr Ser Val Ile Leu Gly Ala Arg
        275                 280                 285

Thr Ala Glu Gln Leu Lys Asp Asn Leu Gly Ala Ala Asp Leu Val Leu
    290                 295                 300
```

-continued

Ser Glu Ala Asp Met Glu Arg Leu Asn Ala Val Ser Ala Pro Gln Met
305 310 315 320

Ala Asp Tyr Pro Tyr Gly Thr Gly Gly Ile Gly Gln Arg Asn Arg Lys
325 330 335

Ile Glu Gly Gly Arg
340

<210> SEQ ID NO 20
<211> LENGTH: 341
<212> TYPE: PRT
<213> ORGANISM: Artificial Sequence
<220> FEATURE:
<223> OTHER INFORMATION: polypeptide/enzyme

<400> SEQUENCE: 20

Met Asp Tyr Arg Lys Leu Gly Asn Ser Gly Ala Val Val Ser Asn Leu
1 5 10 15

Cys Leu Gly Thr Met Thr Phe Gly Asp Glu Ala Asp Glu Ala Thr Ser
20 25 30

Phe Val Leu Met Asp Gln Tyr Val Glu Ala Gly Gly Asn Phe Leu Asp
35 40 45

Thr Ala Asp Val Tyr Ser Ala Gly Leu Ser Glu Glu Ile Val Gly Arg
50 55 60

Trp Leu Lys Gly Lys Lys Leu Arg Asp Leu Val Ile Ala Thr Lys Gly
65 70 75 80

Arg Phe Pro Met Gly Asn Gly Pro Asn His Leu Gly Leu Ser Arg Lys
85 90 95

His Leu Gly Glu Ala Leu Asp Ala Ser Leu Gln Arg Leu Gly Val Glu
100 105 110

Gln Ile Asp Leu Tyr Gln Met His Ala Trp Asp Ala Leu Thr Pro Leu
115 120 125

Glu Glu Thr Leu Arg Phe Leu Asp Asp Ser Ile Arg Ser Gly Lys Ile
130 135 140

Ala Tyr Tyr Gly Phe Ser Asn Phe Leu Gly Trp His Leu Thr Lys Ala
145 150 155 160

Val Trp Met Ala Lys Leu Asn Gly Tyr Ala Ala Pro Val Thr Leu Gln
165 170 175

Pro Gln Tyr Asn Leu Leu Val Arg Asp Ile Glu His Glu Val Val Pro
180 185 190

Ala Cys Glu Asp Ala Gly Met Gly Leu Leu Pro Trp Ser Pro Leu Gly
195 200 205

Gly Gly Trp Leu Ser Gly Lys Tyr Lys Arg Asp Gln Met Pro Glu Gly
210 215 220

Ala Thr Arg Leu Gly Glu Asn Pro Lys Arg Gly Met Glu Ala Tyr Glu
225 230 235 240

Gly Arg Asn Ala Gln Asp Arg Thr Trp Ser Ile Ile Gly Ala Val Glu
245 250 255

Asp Ile Ala Lys Ala Gln Asn Val Ser Met Ala Gln Val Ala Leu Ala
260 265 270

Trp Thr Val Ala Arg Pro Ala Val Thr Ser Val Ile Leu Gly Ala Arg
275 280 285

Thr Ala Glu Gln Leu Lys Asp Asn Leu Gly Ser Val Asp Leu Val Leu
290 295 300

Ser Glu Ala Asp Met Glu Arg Leu Asn Ala Ala Ser Ala Pro Gln Met
305 310 315 320

```
Ser Asp Tyr Pro Tyr Gly Thr Gly Gly Ile Gly Gln Arg Asn Arg Lys
                325                 330                 335

Leu Glu Gly Gly Arg
            340


<210> SEQ ID NO 21
<211> LENGTH: 341
<212> TYPE: PRT
<213> ORGANISM: Artificial Sequence
<220> FEATURE:
<223> OTHER INFORMATION: polypeptide/enzyme

<400> SEQUENCE: 21

Met Asp Tyr Arg Lys Leu Gly Asn Ser Gly Ala Val Val Ser Asn Leu
1               5                   10                  15

Cys Leu Gly Thr Met Thr Phe Gly Asp Glu Ala Asp Glu Ala Thr Ser
            20                  25                  30

Phe Leu Leu Met Asp Gln Tyr Val Glu Ala Gly Gly Asn Phe Leu Asp
        35                  40                  45

Thr Ala Asp Val Tyr Ser Thr Gly Val Ser Glu Glu Ile Ile Gly Arg
    50                  55                  60

Trp Leu Lys Gly Lys Lys Leu Arg Asp Leu Val Ile Ala Thr Lys Gly
65                  70                  75                  80

Arg Phe Pro Met Gly Gln Gly Pro Asn His Leu Gly Leu Ser Arg Lys
                85                  90                  95

His Leu Gly Glu Ala Leu Asp Ala Ser Leu Gln Arg Leu Gly Val Glu
            100                 105                 110

Gln Ile Asp Leu Tyr Gln Met His Ala Trp Asp Ala Leu Thr Pro Leu
        115                 120                 125

Glu Glu Thr Leu Arg Phe Leu Asp Asp Ser Ile Arg Ser Gly Lys Ile
    130                 135                 140

Ala Tyr Tyr Gly Phe Ser Asn Phe Leu Gly Trp His Leu Thr Lys Ala
145                 150                 155                 160

Val Trp Met Ala Lys Leu Asn Gly Tyr Ala Ala Pro Val Thr Leu Gln
                165                 170                 175

Pro Gln Tyr Asn Leu Leu Val Arg Asp Ile Glu His Glu Val Val Pro
            180                 185                 190

Ala Cys Glu Asp Ala Gly Met Gly Leu Leu Pro Trp Ser Pro Leu Gly
        195                 200                 205

Gly Gly Trp Leu Ser Gly Lys Tyr Lys Arg Asp Gln Met Pro Glu Gly
    210                 215                 220

Ala Thr Arg Leu Gly Glu Asn Pro Lys Arg Gly Met Glu Ala Tyr Glu
225                 230                 235                 240

Gly Arg Asn Ala Gln Asp Arg Thr Trp Ser Ile Ile Gly Ala Val Glu
                245                 250                 255

Asp Ile Ala Lys Ala Gln Asp Val Thr Met Ala Gln Val Ala Leu Ala
            260                 265                 270

Trp Thr Ala Ala Arg Pro Ala Val Thr Ser Val Ile Leu Gly Ala Arg
        275                 280                 285

Thr Ala Glu Gln Leu Lys Asp Asn Leu Gly Ser Val Asp Leu Val Leu
    290                 295                 300

Ser Glu Ala Asp Met Glu Arg Leu Asn Ala Ala Ser Ala Pro Gln Met
305                 310                 315                 320

Ser Asp Tyr Pro Tyr Gly Thr Gly Gly Ile Gly Gln Arg Asn Arg Lys
                325                 330                 335
```

```
Leu Glu Gly Gly Arg
            340


<210> SEQ ID NO 22
<211> LENGTH: 341
<212> TYPE: PRT
<213> ORGANISM: Artificial Sequence
<220> FEATURE:
<223> OTHER INFORMATION: polypeptide/enzyme

<400> SEQUENCE: 22

Met Asp Tyr Arg Lys Leu Gly Asn Ser Gly Ala Val Val Ser Asn Leu
1               5                   10                  15

Cys Leu Gly Thr Met Thr Phe Gly Asp Glu Ala Asp Glu Ala Thr Ser
            20                  25                  30

Phe Val Leu Met Asp Gln Tyr Val Glu Ala Gly Gly Asn Phe Leu Asp
        35                  40                  45

Thr Ala Asp Val Tyr Ser Ala Gly Leu Ser Glu Glu Ile Ile Gly Arg
    50                  55                  60

Trp Leu Lys Ala Lys Arg Leu Arg Asn Leu Val Ile Ala Ser Lys Gly
65                  70                  75                  80

Arg Phe Pro Met Gly Asn Gly Pro Asn His Leu Gly Leu Ser Arg Lys
                85                  90                  95

His Leu Gly Glu Ala Leu Asp Ala Ser Leu Gln Arg Leu Gly Val Glu
            100                 105                 110

Gln Ile Asp Leu Tyr Gln Met His Ala Trp Asp Ala Leu Thr Pro Leu
        115                 120                 125

Glu Glu Thr Leu Arg Phe Leu Asp Asp Ala Ile Arg Ser Gly Lys Ile
    130                 135                 140

Ala Tyr Tyr Gly Phe Ser Asn Phe Leu Gly Trp His Ile Thr Lys Ala
145                 150                 155                 160

Val Trp Met Ala Arg Ala Gln Gly Tyr Ala Ala Pro Val Thr Leu Gln
                165                 170                 175

Pro Gln Tyr Asn Leu Leu Val Arg Asp Ile Glu His Glu Val Val Pro
            180                 185                 190

Ala Cys Glu Asp Ala Gly Met Gly Leu Leu Pro Trp Ser Pro Leu Gly
        195                 200                 205

Gly Gly Trp Leu Ser Gly Lys Tyr Lys Arg Asp Gln Met Pro Glu Gly
    210                 215                 220

Ala Thr Arg Leu Gly Glu Asn Pro Lys Arg Gly Met Glu Ala Tyr Glu
225                 230                 235                 240

Gly Arg Asn Ala Gln Asp Arg Thr Trp Ser Ile Ile Gly Ala Val Glu
                245                 250                 255

Asp Ile Ala Lys Ala Gln Asn Val Ser Met Ala Gln Val Ala Leu Ala
            260                 265                 270

Trp Thr Ala Ala Arg Pro Ala Val Thr Ser Val Ile Leu Gly Ala Arg
        275                 280                 285

Thr Ala Glu Gln Leu Lys Asp Asn Leu Gly Ser Val Asp Leu Val Leu
    290                 295                 300

Ser Glu Ala Asp Met Glu Arg Leu Asn Ala Ala Ser Ala Pro Gln Met
305                 310                 315                 320

Ser Asp Tyr Pro Tyr Gly Thr Gly Gly Ile Gly Gln Arg Asn Arg Lys
                325                 330                 335

Leu Glu Gly Gly Arg
            340
```

-continued

<210> SEQ ID NO 23
<211> LENGTH: 341
<212> TYPE: PRT
<213> ORGANISM: Artificial Sequence
<220> FEATURE:
<223> OTHER INFORMATION: polypeptide/enzyme

<400> SEQUENCE: 23

```
Met Asp Tyr Arg Lys Leu Gly Asn Ser Gly Ala Val Val Ser Asn Leu
1               5                   10                  15

Cys Leu Gly Thr Met Thr Phe Gly Asp Glu Ala Asp Glu Ala Thr Ser
            20                  25                  30

Phe Leu Leu Met Asp Gln Tyr Val Glu Ala Gly Gly Asn Phe Leu Asp
        35                  40                  45

Thr Ala Asp Val Tyr Ser Ala Gly Val Ser Glu Glu Ile Val Gly Arg
    50                  55                  60

Trp Leu Lys Ala Lys Lys Leu Arg Asn Leu Val Ile Ala Thr Lys Gly
65                  70                  75                  80

Arg Phe Pro Met Gly Asn Gly Pro Asn His Leu Gly Leu Ser Arg Lys
                85                  90                  95

His Leu Gly Glu Ala Leu Asp Ala Ser Leu Gln Arg Leu Gly Val Glu
            100                 105                 110

Gln Ile Asp Leu Tyr Gln Met His Ala Trp Asp Ala Leu Thr Pro Leu
        115                 120                 125

Glu Glu Thr Leu Arg Phe Leu Asp Asp Ala Ile Arg Ser Gly Lys Ile
    130                 135                 140

Ala Tyr Tyr Gly Phe Ser Asn Phe Leu Gly Trp His Ile Thr Lys Ala
145                 150                 155                 160

Val Trp Met Ala Lys Ala Asn Gly Tyr Ala Ala Pro Val Thr Leu Gln
                165                 170                 175

Pro Gln Tyr Asn Leu Leu Val Arg Asp Ile Glu His Glu Val Val Pro
            180                 185                 190

Ala Cys Glu Asp Ala Gly Met Gly Leu Leu Pro Trp Ser Pro Leu Gly
        195                 200                 205

Gly Gly Trp Leu Ser Gly Lys Tyr Lys Arg Asp Gln Met Pro Glu Gly
    210                 215                 220

Ala Thr Arg Leu Gly Glu Asn Pro Lys Arg Gly Met Glu Ala Tyr Glu
225                 230                 235                 240

Gly Arg Asn Ala Gln Glu Arg Thr Trp Ser Ile Ile Gly Ala Val Glu
                245                 250                 255

Asp Ile Ala Lys Ala Gln Asp Val Ser Met Ala Gln Val Ala Leu Ala
            260                 265                 270

Trp Thr Ala Ala Arg Pro Ala Val Thr Ser Val Ile Leu Gly Ala Arg
        275                 280                 285

Thr Ala Glu Gln Leu Lys Asp Asn Leu Gly Ser Ala Asp Leu Val Leu
    290                 295                 300

Ser Glu Ala Asp Met Glu Arg Leu Asn Ala Ala Ser Ala Pro Gln Met
305                 310                 315                 320

Ala Asp Tyr Pro Tyr Gly Thr Gly Gly Ile Gly Gln Arg Asn Arg Lys
                325                 330                 335

Leu Glu Gly Gly Arg
            340
```

<210> SEQ ID NO 24

<211> LENGTH: 341
<212> TYPE: PRT
<213> ORGANISM: Artificial Sequence
<220> FEATURE:
<223> OTHER INFORMATION: polypeptide/enzyme

<400> SEQUENCE: 24

```
Met Asp Tyr Arg Lys Leu Gly Asn Ser Gly Ala Val Val Ser Asn Leu
1               5                   10                  15

Cys Leu Gly Thr Met Thr Phe Gly Asp Glu Ala Asp Glu Ala Thr Ser
            20                  25                  30

Phe Val Leu Met Asp Gln Tyr Val Glu Ala Gly Gly Asn Phe Leu Asp
        35                  40                  45

Thr Ala Asp Val Tyr Ser Thr Gly Leu Ser Glu Glu Ile Ile Gly Arg
    50                  55                  60

Trp Leu Lys Gly Lys Arg Leu Arg Asp Leu Val Ile Ala Ser Lys Gly
65                  70                  75                  80

Arg Phe Pro Met Gly Gln Gly Pro Asn His Leu Gly Leu Ser Arg Lys
                85                  90                  95

His Leu Gly Glu Ala Leu Asp Ala Ser Leu Gln Arg Leu Gly Val Glu
            100                 105                 110

Gln Ile Asp Leu Tyr Gln Met His Ala Trp Asp Ala Leu Thr Pro Leu
        115                 120                 125

Glu Glu Thr Leu Arg Phe Leu Asp Asp Ser Val Arg Ser Gly Lys Ile
    130                 135                 140

Ala Tyr Tyr Gly Phe Ser Asn Phe Leu Gly Trp His Leu Thr Lys Ala
145                 150                 155                 160

Val Trp Met Ala Arg Leu Gln Gly Tyr Ala Ala Pro Val Thr Leu Gln
                165                 170                 175

Pro Gln Tyr Asn Leu Leu Val Arg Asp Ile Glu His Glu Val Val Pro
            180                 185                 190

Ala Cys Glu Asp Ala Gly Met Gly Leu Leu Pro Trp Ser Pro Leu Gly
        195                 200                 205

Gly Gly Trp Leu Ser Gly Lys Tyr Lys Arg Asp Gln Met Pro Glu Gly
    210                 215                 220

Ala Thr Arg Leu Gly Glu Asn Pro Lys Arg Gly Met Glu Ala Tyr Glu
225                 230                 235                 240

Gly Arg Asn Ala Gln Asp Arg Thr Trp Ala Ile Ile Gly Ala Val Glu
                245                 250                 255

Asp Ile Ala Lys Ala Gln Asn Val Thr Met Ala Gln Val Ala Leu Ala
            260                 265                 270

Trp Thr Val Ala Arg Pro Ala Val Thr Ser Val Ile Leu Gly Ala Arg
        275                 280                 285

Thr Ala Glu Gln Leu Lys Asp Asn Leu Gly Ala Val Asp Leu Val Leu
    290                 295                 300

Ser Glu Ala Asp Met Glu Arg Leu Asn Ala Val Ser Ala Pro Gln Met
305                 310                 315                 320

Ser Asp Tyr Pro Tyr Gly Thr Gly Gly Ile Gly Gln Arg Asn Arg Lys
                325                 330                 335

Ile Glu Gly Gly Arg
            340
```

<210> SEQ ID NO 25
<211> LENGTH: 341
<212> TYPE: PRT
<213> ORGANISM: Artificial Sequence
<220> FEATURE:
<223> OTHER INFORMATION: polypeptide/enzyme

<400> SEQUENCE: 25

Met Asp Tyr Arg Lys Leu Gly Asn Ser Gly Ala Val Val Ser Asn Leu
1               5                   10                  15

Cys Leu Gly Thr Met Thr Phe Gly Asp Glu Ala Asp Glu Ala Thr Ser
            20                  25                  30

Phe Leu Leu Met Asp Gln Tyr Val Glu Ala Gly Gly Asn Phe Leu Asp
        35                  40                  45

Thr Ala Asp Val Tyr Ser Ala Gly Leu Ser Glu Glu Ile Ile Gly Arg
    50                  55                  60

Trp Leu Lys Ala Lys Arg Leu Arg Asp Leu Val Ile Ala Thr Lys Gly
65                  70                  75                  80

Arg Phe Pro Met Gly Asn Gly Pro Asn His Leu Gly Leu Ser Arg Lys
                85                  90                  95

His Leu Gly Glu Ala Leu Asp Ala Ser Leu Gln Arg Leu Gly Val Glu
            100                 105                 110

Gln Ile Asp Leu Tyr Gln Met His Ala Trp Asp Ala Leu Thr Pro Leu
        115                 120                 125

Glu Glu Thr Leu Arg Phe Leu Asp Asp Ala Val Arg Ser Gly Lys Ile
    130                 135                 140

Ala Tyr Tyr Gly Phe Ser Asn Phe Leu Gly Trp His Leu Thr Lys Ala
145                 150                 155                 160

Val Trp Met Ala Lys Ala Gln Gly Tyr Ala Ala Pro Val Thr Leu Gln
                165                 170                 175

Pro Gln Tyr Asn Leu Leu Val Arg Asp Ile Glu His Glu Val Val Pro
            180                 185                 190

Ala Cys Glu Asp Ala Gly Met Gly Leu Leu Pro Trp Ser Pro Leu Gly
        195                 200                 205

Gly Gly Trp Leu Ser Gly Lys Tyr Lys Arg Asp Gln Met Pro Glu Gly
    210                 215                 220

Ala Thr Arg Leu Gly Glu Asn Pro Lys Arg Gly Met Glu Ala Tyr Glu
225                 230                 235                 240

Gly Arg Asn Ala Gln Asp Arg Thr Trp Ala Ile Ile Gly Ala Val Glu
                245                 250                 255

Asp Ile Ala Lys Ala Gln Asp Val Ser Met Ala Gln Val Ala Leu Ala
            260                 265                 270

Trp Thr Val Ala Arg Pro Ala Val Thr Ser Val Ile Leu Gly Ala Arg
        275                 280                 285

Thr Ala Glu Gln Leu Lys Asp Asn Leu Gly Ser Ala Asp Leu Val Leu
    290                 295                 300

Ser Glu Ala Asp Met Glu Arg Leu Asn Ala Val Ser Ala Pro Gln Met
305                 310                 315                 320

Ser Asp Tyr Pro Tyr Gly Thr Gly Gly Ile Gly Gln Arg Asn Arg Lys
                325                 330                 335

Leu Glu Gly Gly Arg
            340

<210> SEQ ID NO 26
<211> LENGTH: 341
<212> TYPE: PRT
<213> ORGANISM: Artificial Sequence
<220> FEATURE:
<223> OTHER INFORMATION: polypeptide/enzyme

<400> SEQUENCE: 26

Met Asp Tyr Arg Lys Leu Gly Asn Ser Gly Ala Val Val Ser Asn Leu
1 5 10 15

Cys Leu Gly Thr Met Thr Phe Gly Asp Glu Ala Asp Glu Ala Thr Ser
20 25 30

Phe Leu Leu Met Asp Gln Tyr Val Glu Ala Gly Gly Asn Phe Leu Asp
35 40 45

Thr Ala Asp Val Tyr Ser Thr Gly Val Ser Glu Glu Ile Val Gly Arg
50 55 60

Trp Leu Lys Gly Lys Lys Leu Arg Asp Leu Val Ile Ala Thr Lys Gly
65 70 75 80

Arg Phe Pro Met Gly Gln Gly Pro Asn His Leu Gly Leu Ser Arg Lys
85 90 95

His Leu Gly Glu Ala Leu Asp Ala Ser Leu Gln Arg Leu Gly Val Glu
100 105 110

Gln Ile Asp Leu Tyr Gln Met His Ala Trp Asp Ala Leu Thr Pro Leu
115 120 125

Glu Glu Thr Leu Arg Phe Leu Asp Asp Ala Val Arg Ser Gly Lys Ile
130 135 140

Ala Tyr Tyr Gly Phe Ser Asn Phe Leu Gly Trp His Leu Thr Lys Ala
145 150 155 160

Val Trp Met Ala Lys Leu Asn Gly Tyr Ala Ala Pro Val Thr Leu Gln
165 170 175

Pro Gln Tyr Asn Leu Leu Val Arg Asp Ile Glu His Glu Val Val Pro
180 185 190

Ala Cys Glu Asp Ala Gly Met Gly Leu Leu Pro Trp Ser Pro Leu Gly
195 200 205

Gly Gly Trp Leu Ser Gly Lys Tyr Lys Arg Asp Gln Met Pro Glu Gly
210 215 220

Ala Thr Arg Leu Gly Glu Asn Pro Lys Arg Gly Met Glu Ala Tyr Glu
225 230 235 240

Gly Arg Asn Ala Gln Glu Arg Thr Trp Ala Ile Ile Gly Ala Val Glu
245 250 255

Asp Ile Ala Lys Ala Gln Asp Val Thr Met Ala Gln Val Ala Leu Ala
260 265 270

Trp Thr Val Ala Arg Pro Ala Val Thr Ser Val Ile Leu Gly Ala Arg
275 280 285

Thr Ala Glu Gln Leu Lys Asp Asn Leu Gly Ser Val Asp Leu Val Leu
290 295 300

Ser Glu Ala Asp Met Glu Arg Leu Asn Ala Ala Ser Ala Pro Gln Met
305 310 315 320

Ala Asp Tyr Pro Tyr Gly Thr Gly Gly Ile Gly Gln Arg Asn Arg Lys
325 330 335

Ile Glu Gly Gly Arg
340

<210> SEQ ID NO 27
<211> LENGTH: 341
<212> TYPE: PRT
<213> ORGANISM: Artificial Sequence
<220> FEATURE:
<223> OTHER INFORMATION: polypeptide/enzyme

<400> SEQUENCE: 27

Met Asp Tyr Arg Lys Leu Gly Asn Ser Gly Ala Val Val Ser Asn Leu

-continued

```
1               5                   10                  15

Cys Leu Gly Thr Met Thr Phe Gly Asp Glu Ala Asp Glu Ala Thr Ser
            20                  25                  30

Phe Leu Leu Met Asp Gln Tyr Val Glu Ala Gly Gly Asn Phe Leu Asp
        35                  40                  45

Thr Ala Asp Val Tyr Ser Thr Gly Leu Ser Glu Glu Ile Ile Gly Arg
    50                  55                  60

Trp Leu Lys Ala Lys Lys Leu Arg Asp Leu Val Ile Ala Ser Lys Gly
65                  70                  75                  80

Arg Phe Pro Met Gly Asn Gly Pro Asn His Leu Gly Leu Ser Arg Lys
                85                  90                  95

His Leu Gly Glu Ala Leu Asp Ala Ser Leu Gln Arg Leu Gly Val Glu
            100                 105                 110

Gln Ile Asp Leu Tyr Gln Met His Ala Trp Asp Ala Leu Thr Pro Leu
        115                 120                 125

Glu Glu Thr Leu Arg Phe Leu Asp Asp Ser Ile Arg Ser Gly Lys Ile
    130                 135                 140

Ala Tyr Tyr Gly Phe Ser Asn Phe Leu Gly Trp His Leu Thr Lys Ala
145                 150                 155                 160

Val Trp Met Ala Arg Ala Asn Gly Tyr Ala Ala Pro Val Thr Leu Gln
                165                 170                 175

Pro Gln Tyr Asn Leu Leu Val Arg Asp Ile Glu His Glu Val Val Pro
            180                 185                 190

Ala Cys Glu Asp Ala Gly Met Gly Leu Leu Pro Trp Ser Pro Leu Gly
        195                 200                 205

Gly Gly Trp Leu Ser Gly Lys Tyr Lys Arg Asp Gln Met Pro Glu Gly
    210                 215                 220

Ala Thr Arg Leu Gly Glu Asn Pro Lys Arg Gly Met Glu Ala Tyr Glu
225                 230                 235                 240

Gly Arg Asn Ala Gln Asp Arg Thr Trp Ser Ile Ile Gly Ala Val Glu
                245                 250                 255

Asp Ile Ala Lys Ala Gln Asp Val Thr Met Ala Gln Val Ala Leu Ala
            260                 265                 270

Trp Thr Val Ala Arg Pro Ala Val Thr Ser Val Ile Leu Gly Ala Arg
        275                 280                 285

Thr Ala Glu Gln Leu Lys Asp Asn Leu Gly Ala Ala Asp Leu Val Leu
    290                 295                 300

Ser Glu Ala Asp Met Glu Arg Leu Asn Ala Val Ser Ala Pro Gln Met
305                 310                 315                 320

Ala Asp Tyr Pro Tyr Gly Thr Gly Gly Ile Gly Gln Arg Asn Arg Lys
                325                 330                 335

Ile Glu Gly Gly Arg
            340


<210> SEQ ID NO 28
<211> LENGTH: 341
<212> TYPE: PRT
<213> ORGANISM: Artificial Sequence
<220> FEATURE:
<223> OTHER INFORMATION: polypeptide/enzyme

<400> SEQUENCE: 28

Met Asp Tyr Arg Lys Leu Gly Asn Ser Gly Ala Val Val Ser Asn Leu
1               5                   10                  15

Cys Leu Gly Thr Met Thr Phe Gly Asp Glu Ala Asp Glu Ala Thr Ser
```

-continued

```
            20                  25                  30

Phe Val Leu Met Asp Gln Tyr Val Glu Ala Gly Gly Asn Phe Leu Asp
        35                  40                  45

Thr Ala Asp Val Tyr Ser Thr Gly Val Ser Glu Glu Ile Asn Gly Arg
    50                  55                  60

Trp Leu Lys Gly Lys Lys Leu Arg Asp Leu Val Ile Ala Thr Lys Gly
65                  70                  75                  80

Arg Phe Pro Met Gly Asn Gly Pro Asn His Leu Gly Leu Ser Arg Lys
                85                  90                  95

His Leu Gly Glu Ala Leu Asp Ala Ser Leu Gln Arg Leu Gly Val Glu
            100                 105                 110

Gln Ile Asp Leu Tyr Gln Met His Ala Trp Asp Ala Leu Thr Pro Leu
        115                 120                 125

Glu Glu Thr Leu Arg Phe Leu Asp Asp Ser Ile Arg Ser Gly Lys Ile
    130                 135                 140

Ala Tyr Tyr Gly Phe Ser Asn Phe Leu Gly Trp His Leu Thr Lys Ala
145                 150                 155                 160

Val Trp Met Ala Lys Leu Asn Gly Tyr Ala Ala Pro Val Thr Leu Gln
                165                 170                 175

Pro Gln Tyr Asn Leu Leu Val Arg Asp Ile Glu His Glu Val Val Pro
            180                 185                 190

Ala Cys Glu Asp Ala Gly Met Gly Leu Leu Pro Trp Ser Pro Leu Gly
        195                 200                 205

Gly Gly Trp Leu Ser Gly Lys Tyr Lys Arg Asp Gln Met Pro Glu Gly
    210                 215                 220

Ala Thr Arg Leu Gly Glu Asn Pro Lys Arg Gly Met Glu Ala Tyr Glu
225                 230                 235                 240

Gly Arg Asn Ala Gln Glu Arg Thr Trp Ala Ile Ile Gly Ala Val Glu
                245                 250                 255

Asp Ile Ala Lys Ala Gln Asp Val Thr Met Ala Gln Val Ala Leu Ala
            260                 265                 270

Trp Thr Ala Ala Arg Pro Ala Val Thr Ser Val Ile Leu Gly Ala Arg
        275                 280                 285

Thr Ala Glu Gln Leu Lys Asp Asn Leu Gly Ala Val Asp Leu Val Leu
    290                 295                 300

Ser Glu Ala Asp Met Glu Arg Leu Asn Ala Ala Ser Ala Pro Gln Met
305                 310                 315                 320

Ser Asp Tyr Pro Tyr Gly Thr Gly Gly Ile Gly Gln Arg Asn Arg Lys
                325                 330                 335

Ile Glu Gly Gly Arg
            340


<210> SEQ ID NO 29
<211> LENGTH: 343
<212> TYPE: PRT
<213> ORGANISM: Artificial Sequence
<220> FEATURE:
<223> OTHER INFORMATION: polypeptide/enzyme

<400> SEQUENCE: 29

Met Glu Tyr Arg Lys Leu Gly Asn Ser Gly Thr Val Val Thr Ser Tyr
1               5                   10                  15

Cys Leu Gly Thr Met Thr Phe Gly Gln Glu Thr Asp Glu Ala Thr Ser
            20                  25                  30

His Leu Ile Met Asp Asp Tyr Ile Lys Ala Gly Gly Asn Phe Ile Asp
```

```
        35                  40                  45

Thr Ala Asn Val Tyr Ser Ala Gly Val Ser Glu Glu Ile Val Gly Arg
    50                  55                  60

Trp Leu Lys Ala Arg Pro Ser Glu Ala Arg Gln Val Val Val Ala Thr
65                  70                  75                  80

Lys Gly Arg Phe Pro Met Gly Ala Gly Pro Asn Asp Leu Gly Leu Ser
                85                  90                  95

Arg Thr Asn Leu Asn Arg Ala Leu Asn Asp Ser Leu Arg Arg Leu Gly
            100                 105                 110

Val Glu Gln Ile Asp Leu Tyr Gln Met His Ala Trp Asp Ala Val Thr
        115                 120                 125

Pro Ile Glu Glu Thr Leu Arg Phe Leu Asp Asp Ala Val Ser Ala Gly
    130                 135                 140

Lys Ile Ala Tyr Tyr Gly Phe Ser Asn Tyr Leu Gly Trp Gln Val Thr
145                 150                 155                 160

Lys Ala Val His Val Ala Arg Ala Asn His Trp Thr Ala Pro Val Thr
                165                 170                 175

Leu Gln Pro Gln Tyr Asn Leu Leu Val Arg Asp Ile Glu His Glu Ile
            180                 185                 190

Val Pro Ala Cys Gln Asp Ala Ala Met Gly Leu Leu Pro Trp Ser Pro
        195                 200                 205

Leu Gly Gly Gly Trp Leu Ala Gly Lys Tyr Gln Arg Asp Val Met Pro
    210                 215                 220

Ser Gly Ala Thr Arg Leu Gly Glu Asn Pro Asn Arg Gly Met Glu Ser
225                 230                 235                 240

Tyr Gly Pro Arg Asn Ala Gln Glu Arg Thr Trp Gln Ile Ile Asp Met
                245                 250                 255

Val Ala Glu Ile Ala Lys Glu Arg Gly Val Ser Ala Ala Gln Val Ala
            260                 265                 270

Leu Ala Trp Val Val Ala Arg Pro Ala Val Thr Ala Val Ile Leu Gly
        275                 280                 285

Ala Arg Thr Arg Glu Gln Leu Ala Asp Asn Leu Gly Ala Val Ala Val
    290                 295                 300

Thr Leu Ser Thr Glu Glu Met Glu Arg Leu Asn Arg Val Ser Ala Pro
305                 310                 315                 320

Ala Met Ala Asp Tyr Pro Tyr Gly Glu Arg Gly Val Ser Gln Arg His
                325                 330                 335

Arg Lys Met Asp Gly Gly Arg
            340


<210> SEQ ID NO 30
<211> LENGTH: 342
<212> TYPE: PRT
<213> ORGANISM: Artificial Sequence
<220> FEATURE:
<223> OTHER INFORMATION: polypeptide/enzyme

<400> SEQUENCE: 30

Met Asp Tyr Arg Lys Leu Gly Pro Ser Gly Thr Val Val Thr Ala Tyr
1               5                   10                  15

Cys Leu Gly Thr Met Thr Gly Ala Glu Ala Asp Glu Ala Ala Ser His
            20                  25                  30

Lys Leu Leu Asp Asp Tyr Phe Ala Trp Gly Gly Asn Phe Ile Asp Thr
        35                  40                  45

Ala Asp Val Tyr Ser Ala Gly Lys Ser Glu Glu Ile Ile Gly Arg Trp
```

50 55 60

Leu Lys Ala Arg Pro Thr Glu Ala Arg Gln Ala Ile Val Ala Thr Lys
65 70 75 80

Gly Arg Phe Pro Met Gly Asn Gly Pro Asn Asp Ile Gly Leu Ser Arg
85 90 95

Arg His Leu Ser Gln Ala Leu Asp Asp Ser Leu Arg Arg Leu Gly Leu
100 105 110

Glu Gln Ile Asp Leu Tyr Gln Met His Ala Trp Asp Ala Leu Thr Pro
115 120 125

Ile Glu Glu Thr Leu Arg Phe Leu Asp Asp Ala Val Ser Ser Gly Lys
130 135 140

Ile Gly Tyr Tyr Gly Phe Ser Asn Tyr Val Gly Trp His Ile Ala Lys
145 150 155 160

Ala Ser Glu Ile Ala Lys Ala Arg Gly Tyr Thr Arg Pro Val Thr Leu
165 170 175

Gln Pro Gln Tyr Asn Leu Leu Met Arg Asp Ile Glu Leu Glu Ile Val
180 185 190

Ala Ala Cys Gln Asp Ala Gly Met Gly Leu Leu Pro Trp Ser Pro Leu
195 200 205

Gly Gly Gly Trp Leu Thr Gly Lys Tyr Lys Arg Asp Glu Met Pro Thr
210 215 220

Gly Ala Thr Arg Leu Gly Glu Asn Pro Asn Arg Gly Gly Glu Ser Tyr
225 230 235 240

Ala Pro Arg Asn Ala Gln Glu Arg Thr Trp Ala Ile Ile Gly Thr Val
245 250 255

Glu Glu Ile Ala Lys Ala Arg Gly Val Ser Met Ala Gln Val Ala Leu
260 265 270

Ala Trp Thr Ala Ala Arg Pro Ala Ile Thr Ser Val Ile Leu Gly Ala
275 280 285

Arg Thr Pro Glu Gln Leu Ala Asp Asn Leu Gly Ala Met Lys Val Glu
290 295 300

Leu Ser Gly Glu Glu Met Ala Arg Leu Asn Glu Val Ser Ala Pro Gln
305 310 315 320

Pro Leu Asp Tyr Pro Tyr Gly Lys Gly Gly Ile Asn Gln Arg His Arg
325 330 335

Lys Ile Glu Gly Gly Arg
340

<210> SEQ ID NO 31
<211> LENGTH: 8
<212> TYPE: PRT
<213> ORGANISM: Artificial Sequence
<220> FEATURE:
<223> OTHER INFORMATION: motif

<400> SEQUENCE: 31

Tyr Arg Lys Leu Gly Asn Ser Gly
1 5

<210> SEQ ID NO 32
<211> LENGTH: 7
<212> TYPE: PRT
<213> ORGANISM: Artificial Sequence
<220> FEATURE:
<223> OTHER INFORMATION: motif

<400> SEQUENCE: 32

Leu Gly Thr Met Thr Phe Gly
1 5

<210> SEQ ID NO 33
<211> LENGTH: 13
<212> TYPE: PRT
<213> ORGANISM: Artificial Sequence
<220> FEATURE:
<223> OTHER INFORMATION: motif
<220> FEATURE:
<221> NAME/KEY: MISC_FEATURE
<222> LOCATION: (6)..(6)
<223> OTHER INFORMATION: X is I or L
<220> FEATURE:
<221> NAME/KEY: MISC_FEATURE
<222> LOCATION: (10)..(10)
<223> OTHER INFORMATION: X is N or D

<400> SEQUENCE: 33

Ala Gly Gly Asn Phe Xaa Asp Thr Ala Xaa Val Tyr Ser
1 5 10

<210> SEQ ID NO 34
<211> LENGTH: 8
<212> TYPE: PRT
<213> ORGANISM: Artificial Sequence
<220> FEATURE:
<223> OTHER INFORMATION: motif

<400> SEQUENCE: 34

Glu Thr Leu Arg Phe Leu Asp Asp
1 5

<210> SEQ ID NO 35
<211> LENGTH: 10
<212> TYPE: PRT
<213> ORGANISM: Artificial Sequence
<220> FEATURE:
<223> OTHER INFORMATION: motif
<220> FEATURE:
<221> NAME/KEY: MISC_FEATURE
<222> LOCATION: (4)..(4)
<223> OTHER INFORMATION: X is A or G

<400> SEQUENCE: 35

Gly Lys Ile Xaa Tyr Tyr Gly Phe Ser Asn
1 5 10

<210> SEQ ID NO 36
<211> LENGTH: 10
<212> TYPE: PRT
<213> ORGANISM: Artificial Sequence
<220> FEATURE:
<223> OTHER INFORMATION: motif
<220> FEATURE:
<221> NAME/KEY: MISC_FEATURE
<222> LOCATION: (7)..(7)
<223> OTHER INFORMATION: X is I or V

<400> SEQUENCE: 36

Arg Asp Ile Glu His Glu Xaa Val Pro Ala
1 5 10

<210> SEQ ID NO 37
<211> LENGTH: 13
<212> TYPE: PRT
<213> ORGANISM: Artificial Sequence
<220> FEATURE:
<223> OTHER INFORMATION: motif -continued

<400> SEQUENCE: 37

Gly Leu Leu Pro Trp Ser Pro Leu Gly Gly Gly Trp Leu
1               5                   10

<210> SEQ ID NO 38
<211> LENGTH: 9
<212> TYPE: PRT
<213> ORGANISM: Artificial Sequence
<220> FEATURE:
<223> OTHER INFORMATION: motif

<400> SEQUENCE: 38

Gly Ala Thr Arg Leu Gly Glu Asn Pro
1               5

<210> SEQ ID NO 39
<211> LENGTH: 7
<212> TYPE: PRT
<213> ORGANISM: Artificial Sequence
<220> FEATURE:
<223> OTHER INFORMATION: motif

<400> SEQUENCE: 39

Ala Gln Val Ala Leu Ala Trp
1               5

<210> SEQ ID NO 40
<211> LENGTH: 12
<212> TYPE: PRT
<213> ORGANISM: Artificial Sequence
<220> FEATURE:
<223> OTHER INFORMATION: motif
<220> FEATURE:
<221> NAME/KEY: MISC_FEATURE
<222> LOCATION: (4)..(4)
<223> OTHER INFORMATION: X is T or A

<400> SEQUENCE: 40

Pro Ala Val Xaa Ser Val Ile Leu Gly Ala Arg Thr
1               5                   10

<210> SEQ ID NO 41
<211> LENGTH: 608
<212> TYPE: PRT
<213> ORGANISM: Artificial Sequence
<220> FEATURE:
<223> OTHER INFORMATION: polypeptide/enzyme

<400> SEQUENCE: 41

Met Arg Phe Glu Tyr Leu Arg Gln Asn Val Val Gly Leu Ala Leu Ser
1               5                   10                  15

Thr Ala Leu Ile Ala Ser Leu Ser Gly Pro Ala Phe Ala Gln His Asp
            20                  25                  30

Ala Asn Ala Ala Ala Glu Pro Ser Lys Ala Gly Gln Ser Ala Ile Glu
        35                  40                  45

Asn Phe Gln Pro Val Thr Ala Asp Asp Leu Ala Gly Lys Asn Pro Ala
    50                  55                  60

Asn Trp Pro Ile Leu Arg Gly Asn Tyr Gln Gly Trp Gly Tyr Ser Pro
65                  70                  75                  80

Leu Asp Gln Ile Asn Lys Asp Asn Val Gly Asp Leu Gln Leu Val Trp
                85                  90                  95

Ser Arg Thr Met Glu Pro Gly Ser Asn Glu Gly Ala Ala Ile Ala Tyr
            100                 105                 110

-continued

```
Asn Gly Val Ile Phe Leu Gly Asn Thr Asn Asp Val Ile Gln Ala Ile
        115                 120                 125

Asp Gly Lys Thr Gly Ser Leu Ile Trp Glu Tyr Arg Arg Lys Leu Pro
    130                 135                 140

Ser Ala Ser Lys Phe Ile Asn Ser Leu Gly Ala Ala Lys Arg Ser Ile
145                 150                 155                 160

Ala Leu Phe Gly Asp Lys Val Tyr Phe Val Ser Trp Asp Asn Phe Val
                165                 170                 175

Val Ala Leu Asp Ala Lys Thr Gly Lys Leu Ala Trp Glu Thr Asn Arg
            180                 185                 190

Gly Gln Gly Val Glu Glu Gly Val Ala Asn Ser Ser Gly Pro Ile Val
        195                 200                 205

Val Asp Gly Val Val Ile Ala Gly Ser Thr Cys Gln Phe Ser Gly Phe
    210                 215                 220

Gly Cys Tyr Val Thr Gly Thr Asp Ala Glu Ser Gly Glu Glu Leu Trp
225                 230                 235                 240

Arg Asn Thr Phe Ile Pro Arg Pro Gly Glu Glu Gly Asp Asp Thr Trp
                245                 250                 255

Gly Gly Ala Pro Tyr Glu Asn Arg Trp Met Thr Gly Ala Trp Gly Gln
            260                 265                 270

Ile Thr Tyr Asp Pro Glu Leu Asp Leu Val Tyr Tyr Gly Ser Thr Gly
        275                 280                 285

Ala Gly Pro Ala Ser Glu Val Gln Arg Gly Thr Glu Gly Gly Thr Leu
    290                 295                 300

Ala Gly Thr Asn Thr Arg Phe Ala Val Lys Pro Lys Thr Gly Glu Val
305                 310                 315                 320

Val Trp Lys His Gln Thr Leu Pro Arg Asp Asn Trp Asp Ser Glu Cys
                325                 330                 335

Thr Phe Glu Met Met Val Val Ser Thr Ser Val Asn Pro Asp Ala Lys
            340                 345                 350

Ala Asp Gly Met Met Ser Val Gly Ala Asn Val Pro Arg Gly Glu Thr
        355                 360                 365

Arg Lys Val Leu Thr Gly Val Pro Cys Lys Thr Gly Val Ala Trp Gln
    370                 375                 380

Phe Asp Ala Lys Thr Gly Asp Tyr Phe Trp Ser Lys Ala Thr Val Glu
385                 390                 395                 400

Gln Asn Ser Ile Ala Ser Ile Asp Asp Thr Gly Leu Val Thr Val Asn
                405                 410                 415

Glu Asp Met Ile Leu Lys Glu Pro Gly Lys Thr Tyr Asn Tyr Cys Pro
            420                 425                 430

Thr Phe Leu Gly Gly Arg Asp Trp Pro Ser Ala Gly Tyr Leu Pro Lys
        435                 440                 445

Ser Asn Leu Tyr Val Ile Pro Leu Ser Asn Ala Cys Tyr Asp Val Met
    450                 455                 460

Ala Arg Thr Thr Glu Ala Thr Pro Ala Asp Val Tyr Asn Thr Asp Ala
465                 470                 475                 480

Thr Leu Val Leu Ala Pro Gly Lys Thr Asn Met Gly Arg Val Asp Ala
                485                 490                 495

Ile Asp Leu Ala Thr Gly Glu Thr Lys Trp Ser Tyr Glu Thr Arg Ala
            500                 505                 510

Ala Leu Tyr Asp Pro Val Leu Thr Thr Gly Gly Asp Leu Val Phe Val
        515                 520                 525

Gly Gly Ile Asp Arg Asp Phe Arg Ala Leu Asp Ala Glu Ser Gly Lys
```

```
    530                 535                 540

Glu Val Trp Ser Thr Arg Leu Pro Gly Ala Val Ser Gly Tyr Thr Thr
545                 550                 555                 560

Ser Tyr Ser Ile Asp Gly Arg Gln Tyr Val Ala Val Val Ser Gly Gly
                565                 570                 575

Ser Leu Gly Gly Pro Thr Phe Gly Pro Thr Thr Pro Asp Val Asp Ser
            580                 585                 590

Ala Ser Gly Ala Asn Gly Ile Tyr Val Phe Ala Leu Pro Glu Lys Lys
        595                 600                 605


<210> SEQ ID NO 42
<211> LENGTH: 586
<212> TYPE: PRT
<213> ORGANISM: Artificial Sequence
<220> FEATURE:
<223> OTHER INFORMATION: polypeptide/enzyme

<400> SEQUENCE: 42

Met Lys Lys Arg Thr Ser Ile Leu Leu Ala Ser Val Ala Met Leu Gly
1               5                   10                  15

Met Gly Ser Thr Ala Phe Ala Gln Val Asp Ile Asn Ala Leu Pro Ala
            20                  25                  30

Val Thr Asp Ala Ile Leu Ala Asn Pro Asp Ala Gly Asp Trp Pro Ser
        35                  40                  45

Tyr Gly Arg Asp Ile Thr Asn Tyr Arg Phe Ser Pro Leu Asp Gln Val
    50                  55                  60

Asn Lys Asp Asn Val Gly Gln Leu Thr Leu Ala Trp Ala Arg Ala Leu
65                  70                  75                  80

Glu Pro Gly Asn Leu Gln Ser Ala Pro Leu Glu Phe Gly Gly Val Leu
                85                  90                  95

Phe Thr Ala Ala Pro Gly Asp Val Val Gln Ala Met Asp Ala Ala Thr
            100                 105                 110

Gly Gln Leu Ile Trp Glu Tyr Arg Arg Gln Leu Pro Asp Arg Ala Thr
        115                 120                 125

Leu Asn Ser Leu Gly Glu Asn Lys Arg Gly Ile Ala Leu Tyr Glu Asp
    130                 135                 140

Lys Ile Tyr Val Ala Thr Trp Asp Asn Phe Ile Val Ala Leu Asp Ala
145                 150                 155                 160

Lys Thr Gly Gln Val Ala Trp Glu Ser Asp Arg Gly Gly Gly Ala Asp
                165                 170                 175

Leu Ile Ser Asn Thr Thr Gly Pro Ile Val Ala Asn Gly Val Val Val
            180                 185                 190

Ala Gly Ser Thr Cys Gln Phe Ser Glu Phe Gly Cys Tyr Val Thr Gly
        195                 200                 205

His Asp Ala Ala Thr Gly Glu Glu Leu Trp Arg Asn Asn Phe Ile Pro
    210                 215                 220

Lys Lys Gly Glu Glu Gly Asp Asp Thr Trp Gly Asp Ser Thr Glu Asp
225                 230                 235                 240

Gln Arg Trp Met Thr Gly Ala Trp Gly Gln Met Thr Tyr Asp Pro Glu
                245                 250                 255

Leu Asp Leu Val Tyr Tyr Gly Ser Thr Gly Ala Gly Pro Ala Ala Glu
            260                 265                 270

Phe Gln Arg Asn Thr Val Gly Gly Thr Leu Phe Gly Ser Asn Thr Arg
        275                 280                 285

Phe Ala Val Lys Pro Lys Thr Gly Glu Ile Val Trp Arg His Gln Val
```

-continued

```
    290                 295                 300

Leu Pro Arg Asp Asn Trp Asp Gln Glu Cys Thr Tyr Glu Met Val Pro
305                 310                 315                 320

Val Asp Ile Asp Ser Ala Pro Ala Ala Asp Met Glu Gly Leu Leu Ala
                325                 330                 335

Leu Gly Thr Ala Ala Pro Gly Lys Lys Arg Val Leu Thr Gly Val Pro
            340                 345                 350

Cys Lys Thr Gly Val Met Trp Gln Phe Asp Ala Gln Thr Gly Glu Phe
        355                 360                 365

Ile Tyr Ala Arg Asp Thr Val Gln Gln Thr Leu Ile Glu Ser Val Asp
    370                 375                 380

Asn Thr Gly Leu Val Thr Val Asn Glu Ala Ala Ile Pro Thr Glu Val
385                 390                 395                 400

Asp Val Ala Thr Pro Met Cys Pro Thr Tyr Leu Gly Gly Arg Asp Trp
                405                 410                 415

Ser Pro Thr Ala Phe Asn Pro Thr Ser Lys Val Met Phe Val Pro Leu
            420                 425                 430

Thr Asn Met Cys Ala Asp Val Thr Val Leu Asp Gln Glu Pro Thr Gly
        435                 440                 445

Leu Asp Val Tyr Asn Thr Glu Leu Thr Tyr Lys Met Pro Glu Gly Val
    450                 455                 460

Thr Asp Ala Gly Arg Ile Asp Ala Ile Asn Val Glu Thr Gly Lys Thr
465                 470                 475                 480

Leu Trp Ser Trp Thr Gln Gln Thr Pro Gln Tyr Ala Ser Ile Thr Ala
                485                 490                 495

Thr Ala Gly Gly Leu Ile Phe Thr Gly Gly Ala Asp Arg Arg Phe Lys
            500                 505                 510

Ala Ile Asp Gln Glu Thr Gly Glu Leu Val Trp Ser Val Thr Leu Gly
        515                 520                 525

Ser Arg Ala Thr Gly His Pro Ile Ser Tyr Glu Val Asp Gly Arg Gln
    530                 535                 540

Tyr Ile Ala Ile Pro Ala Gly Gly Pro Gly Tyr Ala Thr Asp Leu Ile
545                 550                 555                 560

Thr Ala Ser Gly Ser Thr Val Asp Val Val Ser Gly Ser Asn Met Leu
                565                 570                 575

Tyr Val Phe Ala Leu Pro Glu Gln Lys Lys
            580                 585
```